US012653674B2

(12) United States Patent　　　(10) Patent No.:　US 12,653,674 B2
Xiao et al.　　　　　　　　　　　　(45) Date of Patent:　　Jun. 16, 2026

(54) TISSUE CLAMPING DEVICES

(71) Applicant: SHANGHAI NEWMED MEDICAL CO., LTD., Shanghai (CN)

(72) Inventors: Zhenxin Xiao, Shanghai (CN); Qifeng Yu, Shanghai (CN); Tao Qin, Shanghai (CN)

(73) Assignee: SHANGHAI NEWMED MEDICAL CO., LTD., Shanghai (CN)

( * ) Notice: Subject to any disclaimer, the term of this patent is extended or adjusted under 35 U.S.C. 154(b) by 902 days.

(21) Appl. No.: 17/935,560

(22) Filed: Sep. 26, 2022

(65) Prior Publication Data

US 2023/0013416 A1　　Jan. 19, 2023

Related U.S. Application Data

(63) Continuation of application No. PCT/CN2020/125267, filed on Oct. 30, 2020.

(30) Foreign Application Priority Data

Mar. 31, 2020　(CN) ......................... 202010243141.1
Jun. 12, 2020　(CN) ......................... 202021079571.6

(51) Int. Cl.
A61F 2/24　　　　(2006.01)

(52) U.S. Cl.
CPC ...... A61F 2/246 (2013.01); *A61F 2220/0008* (2013.01)

(58) Field of Classification Search
CPC ......................... A61F 2/246; A61F 2220/0008
See application file for complete search history.

(56) References Cited

U.S. PATENT DOCUMENTS

2004/0049207 A1* 3/2004 Goldfarb .............. A61F 2/2463
　　　　　　　　　　　　　　　　　　　　606/139
2015/0190228 A1 7/2015 Lei et al.
　　　　　　　　(Continued)

FOREIGN PATENT DOCUMENTS

CN　　106491245 A　　3/2017
CN　　110495972 A　　11/2019
　　　　　　(Continued)

OTHER PUBLICATIONS

International Search Report in PCT/CN2020/125267 mailed on Jan. 27, 2021, 7 pages.
　　　　　　　　　(Continued)

*Primary Examiner* — Suzette J Gherbi
(74) *Attorney, Agent, or Firm* — METIS IP LLC

(57)　　　　　ABSTRACT

A tissue clamping device including a clamp, a first connector, a second connector, and a clip is provided. The clamp may include a supporting unit, a first interior clamping arm, a first exterior clamping arm, a second interior clamping arm, and a second exterior clamping arm. The supporting unit may be connected to the first interior clamping arm, the first exterior clamping arm, the second interior clamping arm, and the second exterior clamping arm. The clamp may be connected to a portion between the first connector and the second connector. A relative movement of the first connector and the second connector may drive the first interior clamping arm and the second interior clamping arm to be expanded or folded relatively. The clip may include a first clip and a second clip, and the first clip and the second clip may be respectively expanded or folded.

19 Claims, 33 Drawing Sheets

(56) References Cited

U.S. PATENT DOCUMENTS

| | | | |
|---|---|---|---|
| 2017/0265994 A1 | 9/2017 | Krone | |
| 2018/0296331 A1 | 10/2018 | Dixon et al. | |
| 2018/0296333 A1 | 10/2018 | Dixon et al. | |
| 2019/0000613 A1 | 1/2019 | Delgado et al. | |
| 2019/0000623 A1 | 1/2019 | Pan et al. | |
| 2019/0060075 A1 | 2/2019 | Delgado et al. | |
| 2019/0069991 A1* | 3/2019 | Metchik | A61F 2/2466 |
| 2019/0321166 A1 | 10/2019 | Freschauf et al. | |
| 2020/0113688 A1 | 4/2020 | Mccann et al. | |
| 2020/0163757 A1* | 5/2020 | De Bonis | A61B 17/122 |
| 2020/0383782 A1* | 12/2020 | Basude | A61F 2/2439 |
| 2021/0186698 A1* | 6/2021 | Abunassar | A61F 2/2466 |
| 2021/0212816 A1* | 7/2021 | Marr | A61B 17/1227 |
| 2022/0039943 A1* | 2/2022 | Phan | A61F 2/2466 |
| 2022/0054132 A1* | 2/2022 | Ketai | A61B 17/08 |
| 2022/0142780 A1 | 5/2022 | Zhang et al. | |
| 2022/0151773 A1 | 5/2022 | Dixon et al. | |
| 2022/0226108 A1 | 7/2022 | Freschauf et al. | |
| 2022/0287841 A1* | 9/2022 | Freschauf | A61F 2/2466 |
| 2022/0313433 A1* | 10/2022 | Ma | A61F 2/246 |
| 2023/0013416 A1* | 1/2023 | Xiao | A61F 2/246 |
| 2024/0156598 A1* | 5/2024 | Oliver | A61F 2/2466 |
| 2024/0299169 A1* | 9/2024 | Oberwise | A61F 2/246 |
| 2024/0423801 A1* | 12/2024 | Yi | A61F 2/2466 |
| 2025/0120723 A1* | 4/2025 | Huang | A61F 2/246 |

FOREIGN PATENT DOCUMENTS

| | | | |
|---|---|---|---|
| CN | 111261607 A | 6/2020 |
| CN | 111265340 A | 6/2020 |
| CN | 111265341 A | 6/2020 |
| CN | 111281606 A | 6/2020 |
| CN | 111317596 A | 6/2020 |
| CN | 212547261 U | 2/2021 |
| EP | 3323353 B1 | 6/2021 |
| WO | 2006037073 A2 | 4/2006 |
| WO | 2018195215 A2 | 10/2018 |
| WO | 2021196580 A1 | 10/2021 |
| WO | 2022052506 A1 | 3/2022 |

OTHER PUBLICATIONS

Written Opinion in PCT/CN2020/125267 mailed on Jan. 27, 2021, 5 pages.

The Office Action in Russian Application No. 2022125470 mailed on Apr. 7, 2023, 24 pages.

Request for the Submission of an Opinion in Korean Application No. 10-2022-7036342 mailed on Jul. 9, 2024, 17 pages.

The Extended European Search Report in European Application No. 20928092.4 mailed on Jul. 12, 2023, 10 pages.

* cited by examiner

100

100

100

910        913    912    911            912

912        911

910                912

910

100

930     140     120     160

150     170     130     110

100

100

100

430          440          450          910

430          440          450          452

450

440

430

910

451

451

2200

430    910    440

450
440
430
910

450
440
430
910

510

511

510

511

700

700

200

300

300

600

306

100

306

400

400

450

400

450

453

454

430          470          440

910          441

TISSUE CLAMPING DEVICES

CROSS-REFERENCE TO RELATED APPLICATIONS

This application is a Continuation of International Application No. PCT/CN2020/125267, filed on Oct. 30, 2020, which claims priority to Chinese Patent Application No. 202010243141.1, filed on Mar. 31, 2020, and Chinese Patent Application No. 202021079571.6, filed on Jun. 12, 2020, the contents of each of which are hereby incorporated by reference.

TECHNICAL FIELD

The present disclosure relates to the field of medical supplies, in particular, to a tissue clamping device.

BACKGROUND

In a surgical repairing operation of body tissues, a tissue clamping device may be used to clamp and/or fix the tissues. Take a treatment of a heart disease, e.g., mitral regurgitation, as an example, the mitral valve locates between the left atrium and the left ventricle. When the left ventricle contracts, the mitral valve acts as a check valve to close an atrioventricular orifice and prevent blood from flowing back from the left ventricle into the left atrium. When the mitral valve is diseased, the mitral valve may be difficult to close when the left ventricle contracts, which results in the blood flowing back to the left atrium, a sharp increasement of the venous pressure in the left atrium and/or the lung, an increasement of a volume load of the left ventricle, and further results in pathological changes such as a left ventricular enlargement, pulmonary hypertension, etc. The disease of the mitral valve may further cause clinical manifestations such as heart failure, arrhythmia, etc., which may threaten a patient's life. In the treatment of mitral regurgitation, the tissue clamping device may be used to clamp two opposite sides of the mitral valve to render that there are two relatively small holes, instead of one relative large hole, between the valve of the mitral valve, thereby reducing an area of regurgitation and effectively preventing the mitral regurgitation. Similarly, the tissue clamping device may also be used to clamp valves of the tricuspid valve of a heart to reduce a regurgitation area.

SUMMARY

According to an aspect of the present disclosure, a tissue clamping device is provided. The tissue clamping device may include a first connector, a second connector, and a clip. The clamp may include a supporting unit, a first interior clamping arm, a first exterior clamping arm, a second interior clamping arm, and a second exterior clamping arm. A first side of the supporting unit may be connected to the first interior clamping arm and the first exterior clamping arm in sequence via a bendable connection. A second side of the supporting unit may be connected to the second interior clamping arm and the second exterior clamping arm in sequence via a bendable connection. The clamp may be integrally formed. The clamp may be connected to the first connector and the second connector and between the first connector and the second connector. A relative movement of the first connector and the second connector may drive the first interior clamping arm and the second interior clamping arm to be expanded or folded relatively. The clip may include a first clip disposed on the first interior clamping arm and a second clip disposed on the second interior clamping arm. The first clip and the second clip may be respectively expanded or folded relative to the first interior clamping arm and the second interior clamping arm, thereby clamping tissues between the first clip and the first interior clamping arm and between the second clip and the second interior clamping arm.

In some embodiments, a first end of the supporting unit may be connected to the first connector. A first end of the first exterior clamping arm and a first end of the second exterior clamping arm may be connected to the second connector, respectively.

In some embodiments, the first side of the supporting unit may be connected to the first interior clamping arm via a first bending structure. The second side of the supporting unit may be connected to the second interior clamping arm via the first bending structure. The first bending structure may include a first S rod or a first thin waist bending structure. The first interior clamping arm may be connected to the first exterior clamping arm via a second bending structure. The second interior clamping arm may be connected to the second exterior clamping arm via the second bending structure. The second bending structure may include at least one of a second S rod or a second thin waist bending structure.

In some embodiments, the first S rod or the second S rod may at least include three straight rods and two curved rods. The three straight rods may be parallel to each other and arranged in sequence. Two ends of each two adjacent straight rods of the three straight rods may be connected, and the two ends of each two adjacent straight rods of the three straight rods may be located at a same side of the first S rod or the second S rod. The two ends of each two adjacent straight rods of the three straight rods may be connected via one of the two curved rods.

In some embodiments, the supporting unit may include a grid structure. The grid structure may include a rhombus grid structure, a circular grid structure, a rectangular grid structure, a square grid structure, a triangular grid structure, or a regular polygon grid structure.

In some embodiments, the clamp may be integrally formed by cutting and performing a heating and shaping operation on a shape-memory alloy tube.

In some embodiments, the clip may include an agnail clip. The agnail clip may include a fixing unit, a clipping unit, and an agnail. A first end of the fixing unit may be connected to a first end of the clipping unit via a bending unit. The agnail may be disposed on a second end of the clipping unit.

In some embodiments, the fixing unit, the clipping unit, and the agnail may be integrally formed.

In some embodiments, the agnail may include a plurality of agnail bars. At least one of the plurality of agnail bars may be connected to the second end of the clipping unit via a third S rod, and/or the at least one of the plurality of agnail bars may include one or more through-holes.

In some embodiments, the agnail may be connected to the second end of the clipping unit via a detachable connection. The second end of the clipping unit may include a slot. The agnail may include a snap ring. The snap ring may be connected to the slot via a snapping connection.

In some embodiments, the fixing unit and the clipping unit may be integrally formed by cutting and performing a heating and shaping operation on a shape-memory alloy. After being performed the heating and shaping operation, the fixing unit and the clipping unit may form a certain angle and the bending unit may have prefabricated resilience force.

In some embodiments, each of the first interior clamping arm and the second interior clamping arm may include a through-hole which may be matched with the agnail.

In some embodiments, each of the first interior clamping arm and the second interior clamping arm may include a snap hole matched with the fixing unit of the agnail clip. The fixing unit may be embedded in the snap hole. Each of the first interior clamping arm and the second interior clamping arm may include a fixing slot. The tissue clamping device may further include a fixing ring. The fixing ring may be connected to the fixing slot via a snapping connection to restrict the fixing unit from disengaging from the snap hole.

In some embodiments, the fixing unit and the clipping unit of the agnail clip may be integrally formed with the clamp.

In some embodiments, the tissue clamping device may further include a locking mechanism. The locking mechanism may include a locking tube and a locking piece. One end of the locking tube may be fixedly connected to the second connector, and an exterior wall of the locking tube may include a locking tab. The locking piece may be fixedly connected to the supporting unit. The locking tab may restrict a relative expansion between the first interior clamping arm and the second interior clamping arm by restricting a movement of the locking piece.

In some embodiments, the locking mechanism may further include a sleeve. The sleeve may sleeve outside the locking tube and be configured to retract the locking tab. The tissue clamping device may further include a brake lever, and the brake lever may be fixedly connected to the sleeve and detachably connected to the locking tube. When the brake lever is connected to the locking tube, the sleeve may retract the locking tab. When the brake lever is disengaged from the locking tube, the sleeve may release an effect on the locking tab and the locking tab may be expanded.

In some embodiments, the locking tab may include at least two tabs. The at least two tabs may be disposed on two positions on an exterior wall of the locking tube. A distance between one of the two positions and the second connector and a distance between the other of the two positions and the second connector may be different. The at least two tabs may restrict the clamp from being expanded when the first interior clamping arm and the second interior clamping arm are expanded to different angles.

In some embodiments, the tissue clamping device may further include an elastic bracket. The elastic bracket may include a first supporting rod, a second supporting rod, a first mounting unit, and a second mounting unit. A first end of the first supporting rod and a first end of the second supporting rod may be connected to the first mounting unit. A second end of the first supporting rod and a second end of the second supporting rod may be connected to the second mounting unit. The first supporting rod, the second supporting rod, the first mounting unit, and the second mounting unit may be integrally formed. The first mounting unit and the second mounting unit of the elastic bracket may be fixedly connected to the second connector. The first supporting rod of the elastic bracket may bear against a connection of the first interior clamping arm and the first exterior clamping arm. The second supporting rod of the elastic bracket may bear against a connection of the second interior clamping arm and the second exterior clamping arm.

In some embodiments, each of the first end of the first supporting rod and the first end of the second supporting rod may be connected to the first mounting unit via a curved rod of a fourth S rod. Each of the second end of the first supporting rod and the second end of the second supporting rod may be connected to the second mounting unit via a curved rod of a fifth S rod.

In some embodiments, each of the first end of the first supporting rod and the first end of the second supporting rod may be connected to the first mounting unit via a first connecting unit. Each of the second end of the first supporting rod and the second end of the second supporting rod may be connected to the second mounting unit via a second connecting unit. Each of the first connecting unit and the second connecting unit may include one or more through-holes.

According to another aspect of the present disclosure, a clamp of a tissue clamping device is provided. The clamp of the tissue clamping device may include a supporting unit, a first interior clamping arm, a first exterior clamping arm, a second interior clamping arm, and a second exterior clamping arm. A first side of the supporting unit may be connected to the first interior clamping arm and the first exterior clamping arm in sequence via a bendable connection. A second side of the supporting unit may be connected to the second interior clamping arm and the second exterior clamping arm in sequence via a bendable connection. The clamp may be integrally formed.

In some embodiments, the first side of the supporting unit may be connected to the first interior clamping arm via a first bending structure. The second side of the supporting unit may be connected to the second interior clamping arm via the first bending structure. The first interior clamping arm may be connected to the first exterior clamping arm via a second bending structure. The second interior clamping arm may be connected to the second exterior clamping arm via the second bending structure.

In some embodiments, the first bending structure may include a first S rod or a first thin waist bending structure. The second bending structure may include a second S rod or a second thin waist bending structure.

In some embodiments, the first S rod or the second S rod may at least include three straight rods and two curved rods. The three straight rods may be arranged in sequence. Two ends of each two adjacent straight rods of the three straight rods may be connected, and the two ends of each two adjacent straight rods of the three straight rods may be located at a same side of the first S rod or the second S rod. The two ends of each two adjacent straight rods of the three straight rods may be connected via one of the two curved rods.

In some embodiments, the supporting unit may include a grid structure. The grid structure may include a rhombus grid structure, a circular grid structure, a rectangular grid structure, a square grid structure, a triangular grid structure, or a regular polygon grid structure.

In some embodiments, a cross-sectional shape of the supporting unit may be circular or elliptical. A cross-sectional area of a middle portion of the supporting unit may be larger than cross-sectional areas of two ends of the supporting unit.

In some embodiments, each of the first interior clamping arm and the second interior clamping arm may include an agnail clip which may be integrally formed.

In some embodiments, each of the first exterior clamping arm and the second exterior clamping arm may include a plurality of through-holes configured to assist a deformation of each of the first exterior clamping arm and the second exterior clamping arm during a heating and shaping operation.

In some embodiments, the clamp may be integrally formed by cutting and performing a heating and shaping operation on a shape-memory alloy tube.

According to yet another aspect of the present disclosure, a tissue clamp device is provided. The tissue clamping device may include the clamp described according to some embodiments of the present disclosure.

According to yet another aspect of the present disclosure, an agnail clip is provided. The agnail clip may include a fixing unit, a clipping unit, and an agnail. A first end of the fixing unit may be connected to a first end of the clipping unit via a bending unit. The agnail may be disposed on a second end of the clipping unit.

In some embodiments, the bending unit may include a first S rod.

In some embodiments, the first S rod may at least include three straight rods and two curved rods. The three straight rods may be arranged in sequence. Two ends of each two adjacent straight rods of the three straight rods may be connected, and the two ends of each two adjacent straight rods of the three straight rods may be located at a same side of the first S rod. The two ends of each two adjacent straight rods of the three straight rods may be connected via one of the two curved rods.

In some embodiments, the fixing unit, the clipping unit, and the agnail may be integrally formed.

In some embodiments, the agnail may include a plurality of agnail bars. At least one of the plurality of agnail bars may be connected to the second end of the clipping unit via a second S rod.

In some embodiments, the agnail may include a plurality of agnail bars. At least one of the plurality of agnail bars may include one or more through-holes.

In some embodiments, the agnail may be detachably connected to the second end of the clipping unit.

In some embodiments, the second end of the clipping unit may include a slot. The agnail may include a snap ring. The snap ring may be connected to the slot via a snapping connection.

In some embodiments, the fixing unit and the clipping unit may be integrally formed by cutting and performing a heating and shaping operation on a shape-memory alloy.

In some embodiments, after being performed the heating and shaping operation, the fixing unit and the clipping unit may form an angle, and the bending unit may have prefabricated resilience force.

According to yet another aspect, a tissue clamping device is provided. The tissue clamping device may include the agnail clip described according to some embodiments of the present disclosure.

In some embodiments, the tissue clamping device may include an interior clamping arm, and the agnail clip may be disposed on the interior clamping arm.

In some embodiments, the interior clamping arm may include a through-hole which may be matched with the agnail.

In some embodiments, the interior clamping arm may include a snap hole matched with the fixing unit of the agnail clip, and the fixing unit may be embedded in the snap hole. The interior clamping arm may further include a fixing slot. The tissue clamping device may further include a fixing ring. The fixing ring may be connected to the fixing slot via a snapping connection to restrict the fixing unit from disengaging from the snap hole.

In some embodiments, the fixing unit and the clipping unit of the agnail clip may be integrally formed with the interior clamping arm.

According to yet another aspect of the present disclosure, a tissue clamping device with a locking mechanism is provided. The tissue clamping device may include a clamp, a first connector, a second connector, and the locking mechanism. The clamp may be connected between the first connector and the second connector and between the first connector and the second connector. A relative movement of the first connector and the second connector may drive the clamp to be expanded or folded. The locking mechanism may include a locking tube. One end of the locking tube may be fixedly connected to the second connector. An exterior wall of the locking tube may include a locking tab configured to restrict the clamp from expanding.

In some embodiments, the locking mechanism may further include a locking piece fixedly connected to the clamp. The locking tab may restrict the clamp from being expanded by restricting a movement of the locking piece.

In some embodiments, the clamp may include a supporting unit, and the locking piece may be fixedly connected to the supporting unit.

In some embodiments, the locking mechanism may further include a sleeve. The sleeve may sleeve outside the locking tube and be configured to retract the locking tab.

In some embodiments, the tissue clamping device may further include a brake lever. The brake lever may be fixedly connected to the sleeve and detachably connected to the locking tube. When the brake lever is connected to the locking tube, the sleeve may retract the locking tab. When the brake lever is disengaged from the locking tube, the sleeve may release an effect on the locking tab, and the locking tab may be expanded.

In some embodiments, the brake lever may be connected to the locking tube via a threading connection.

In some embodiments, the locking tab may include at least two tabs. The at least two tabs may be symmetrically disposed on two locations on an exterior wall of the locking tube. A distance between one of the two locations and the second connector and a distance between the other of the two locations and the second connector may be same.

In some embodiments, the locking tab may include at least two tabs disposed on two locations on an exterior wall of the locking tube. A distance between one of the two locations and the second connector and a distance between the other of the two locations and the second connector may be different. The at least two tabs may restrict the clamp from expanding when the first interior clamping arm and the second interior clamping arm are expanded to different angles, relatively.

In some embodiments, the locking tube and the locking tab may be integrally formed.

In some embodiments, the locking tube and the locking tab may be integrally formed by cutting and performing a heating and shaping operation on a shape-memory alloy.

According to yet another aspect of the present disclosure, an elastic bracket of a tissue clamping device is provided. The elastic bracket of the tissue clamping device may include a first supporting rod, a second supporting rod, a first mounting unit, and a second mounting unit. A first end of the first supporting rod and a first end of the second supporting rod may be connected to the first mounting unit. A second end of the first supporting rod and a second end of the second supporting rod may be connected to the second mounting unit. The first supporting rod, the second supporting rod, the first mounting unit, and the second mounting unit may be integrally formed.

In some embodiments, a middle portion of each of the first supporting rod and the second supporting rod may include a first arc segment, a second arc segment, and a third arc segment. A convex direction of the second arc segment may be opposite to convex directions of the first arc segment and the third arc segment.

In some embodiments, a width of the first supporting rod and a width of the second supporting rod may be a positive correlation with elastic force for the tissue clamping device provided by the elastic bracket.

In some embodiments, the first end of the first supporting rod and the first end of the second supporting rod may be connected to the first mounting unit via a curved rod of a first S rod. The second end of the first supporting rod and the second end of the second supporting rod may be connected to the second mounting unit via a curved rod of a second S rod.

In some embodiments, the first S rod or the second S rod may at least include three straight rods and two curved rods. The three straight rods may be parallel to each other. Two ends of each two adjacent straight rods of the three straight rods may be connected, and the two ends of each two adjacent straight rods of the three straight rods may be located at a same side of the first S rod or the second S rod. The two ends of each two adjacent straight rods of the three straight rods may be connected via one of the two curved rods.

In some embodiments, each of the first end of the first supporting rod and the first end of the second supporting rod may be connected to the first mounting unit via a first connecting unit. Each of the second end of the first supporting rod and the second end of the second supporting rod may be connected to the second mounting unit via a second connecting unit. Each of the first connecting unit and the second connecting unit may include one or more through-holes.

In some embodiments, the elastic bracket may be integrally formed by cutting and performing a heating and shaping operation on a shape-memory alloy tube.

In some embodiments, after being performed the heating and shaping operation, the first mounting unit and the second mounting unit may be relatively folded. Each of the first supporting rod and the second supporting rod may have prefabricated resilience force.

According to yet another aspect of the present disclosure, a tissue clamping device is provided. The tissue clamping device may include the elastic bracket of the tissue clamping device described according to some embodiments of the present disclosure.

In some embodiments, the tissue clamping device may further include a clamp, a first connector, and a second connector. The clamp may include a supporting unit, a first interior clamping arm, a first exterior clamping arm, a second interior clamping arm, and a second exterior clamping arm. A first side of the supporting unit may be connected to the first interior clamping arm and the first exterior clamping arm in sequence via a bendable connection. A second side of the supporting unit may be connected to the second interior clamping arm and the second exterior clamping arm in sequence via a bendable connection. The clamp may be connected to the first connector and the second connector and between the first connector and the second connector. A relative movement of the first connector and the second connector may drive the first interior clamping arm and the second interior clamping arm to expand or fold relatively. A first mounting unit and a second mounting unit of the elastic bracket may be fixedly connected to the second connector. The first supporting rod of the elastic bracket may bear against a connection of the first interior clamping arm and the first exterior clamping arm. The second supporting rod of the elastic bracket may bear against a connection of the second interior clamping arm and the second exterior clamping arm.

According to yet another aspect of the present disclosure, an agnail clip is provided. The agnail clip may include a fixing unit, a clipping unit, a bending unit, and an agnail. A first end of the fixing unit may be connected to a first end of the clipping unit via the bending unit. The agnail may be disposed on the clipping unit. The agnail may include at least one agnail bar. A shape of the at least one agnail bar may be an arc and a concave side of the at least one agnail bar may face the first end of the fixing unit.

In some embodiments, the agnail clip may include a mounting unit which may be connected to the clipping unit. The at least one agnail bar may be disposed on the mounting unit.

In some embodiments, the mounting unit may be connected to the clipping unit via a detachable connection.

In some embodiments, the mounting unit may include a snap ring. The snap ring may be sleeved and snapped on the mounting unit.

In some embodiments, the clipping unit may include a slot. The mounting unit may include a fixing piece which may be snapped in the slot.

In some embodiments, the agnail clip may include at least two agnails. The at least two agnails may be disposing at different positions of the clipping unit.

In some embodiments, the agnail may be formed by cutting and performing a heating and shaping operation on a shape-memory alloy.

In some embodiments, the bending unit may include an S rod. The S rod may include three straight rods and two curved rods. The three straight rods may be parallel to each other and arranged in sequence. Each two adjacent straight rods of the three straight rods may be connected via one of the two curved rods.

According to yet another aspect of the present disclosure, a tissue clamping device is provided. The tissue clamping device may include the agnail clip described according to some embodiments of the present disclosure.

In some embodiments, the tissue clamping device may include an interior clamping arm. The fixing unit of the agnail clip may be connected to the interior clamping arm. The agnail may hook tissues when the interior clamping arm clamps the tissues.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

REFERENCE NUMERALS AND REPRESENTED STRUCTURES

Figure 1:
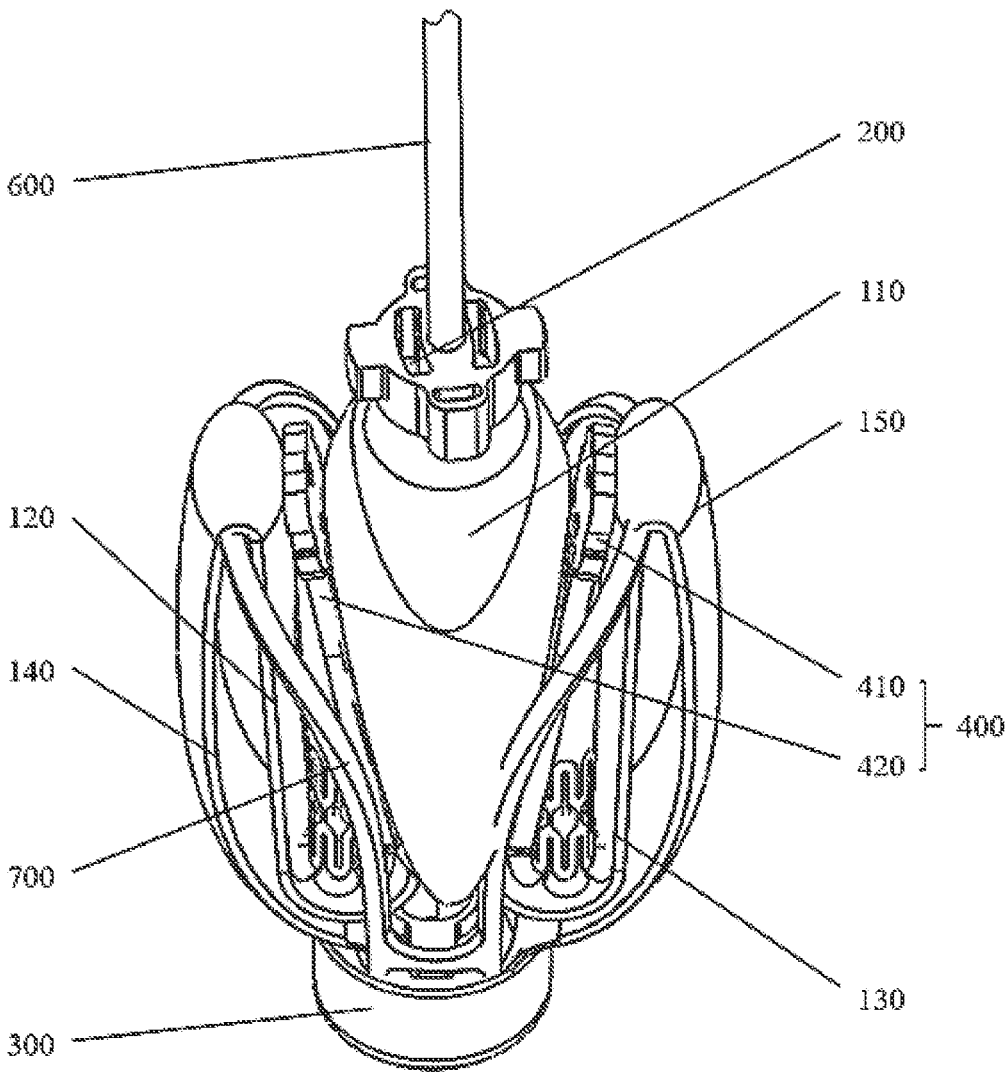
FIG. 1 is a structural schematic diagram illustrating a tissue clamping device according to some embodiments of the present disclosure.

100—clamp, 200—first connector, 300—second connector, 400—clip, 500—locking mechanism, 600—brake lever, 700—elastic bracket, 800—conveying connector, 110—supporting unit, 120—first interior clamping arm, 121—snap hole, 122—fixing slot, 125—through-hole, 130—second interior clamping arm, 140—first exterior clamping arm, 150—second exterior clamping arm, 160—first bending structure, 170—second bending structure, 202—mounting bayonet, 204—through-hole, 206—convex block, 302—connecting hole, 304—mounting hole, 306—convex block, 410—first clip, 420—second clip, 430—fixing unit, 440—clipping unit, 441—slot, 450—agnail, 451—snap ring, 452—through-hole, 453—fixing piece, 454—agnail bar, 460—fixing ring, 470—bending unit, 510—locking tube, 520—locking piece, 530—sleeve, 511—locking tab, 710—first supporting rod, 712—first arc segment, 714—second arc segment, 716—third arc segment, 720—second supporting rod, 730—first mounting unit, 740—second mounting unit, 750—first connecting unit, 760—second connecting unit, 810—main body, 820—first connecting piece, 830—second connecting piece, 840—fixing supporting rod, 910—S rod, 920—thin waist bending structure, 911—straight rod, 912—curved rod, 913—connecting rod, 930—through-hole.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure provides a tissue clamping device. An interior clamping arm of a clamp of the tissue clamping device may be relatively expanded or folded. The clamp of the tissue clamping device may be configured to clamp tissues with a clip. The tissue clamping device may be applied to various occasions, for example, the tissue clamping device may be used for clamping a tissue such as a heart valve (e.g., the mitral valve, the tricuspid valve), the vascular valve, or the like, or any combination thereof. The tissue clamping device may reach a predetermined position through various paths during a tissue clamping process, which are not limited in the present disclosure.

Figure 2:
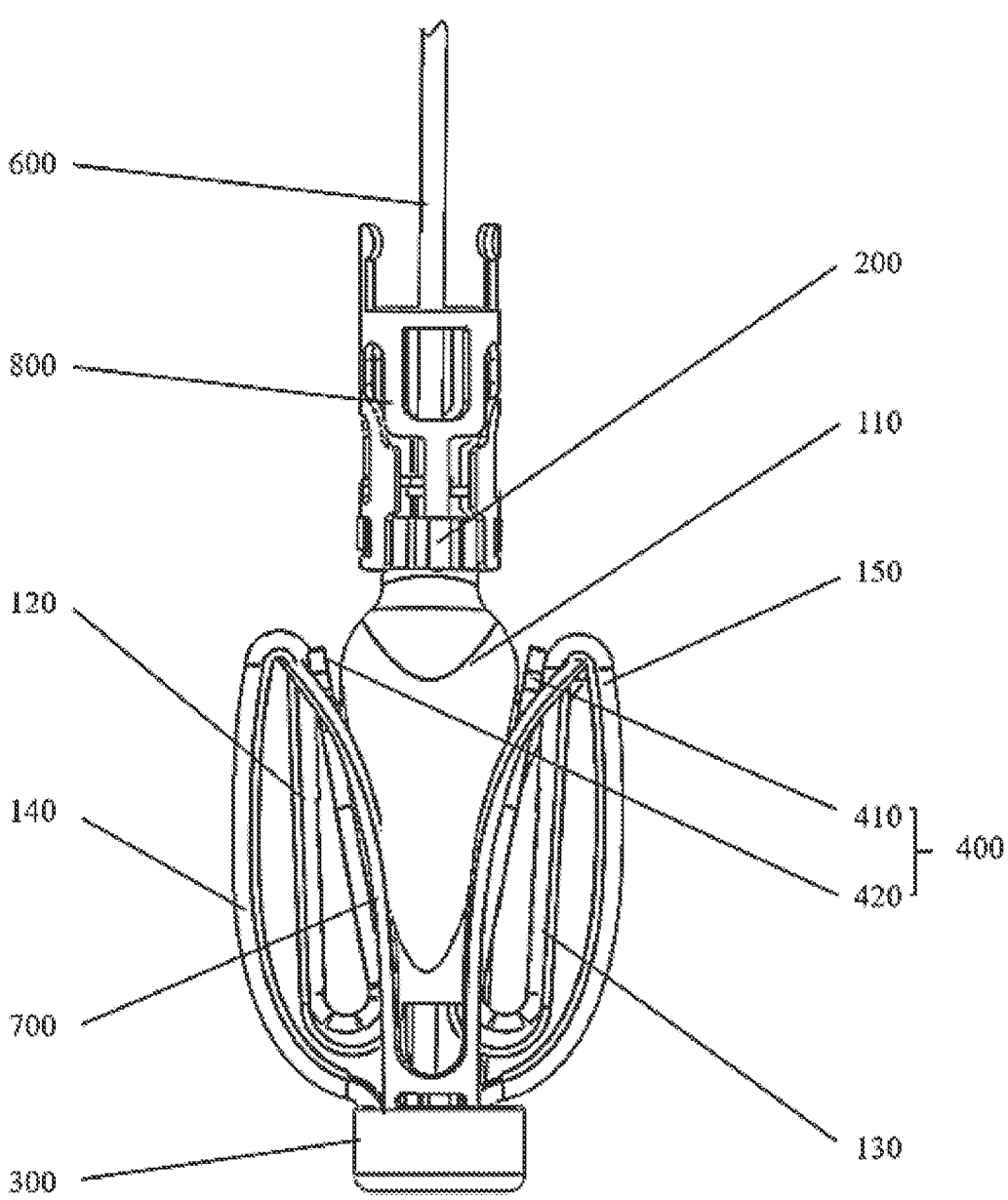
FIG. 2 is a structural schematic diagram illustrating a tissue clamping device according to some embodiments of the present disclosure.
Figure 3:
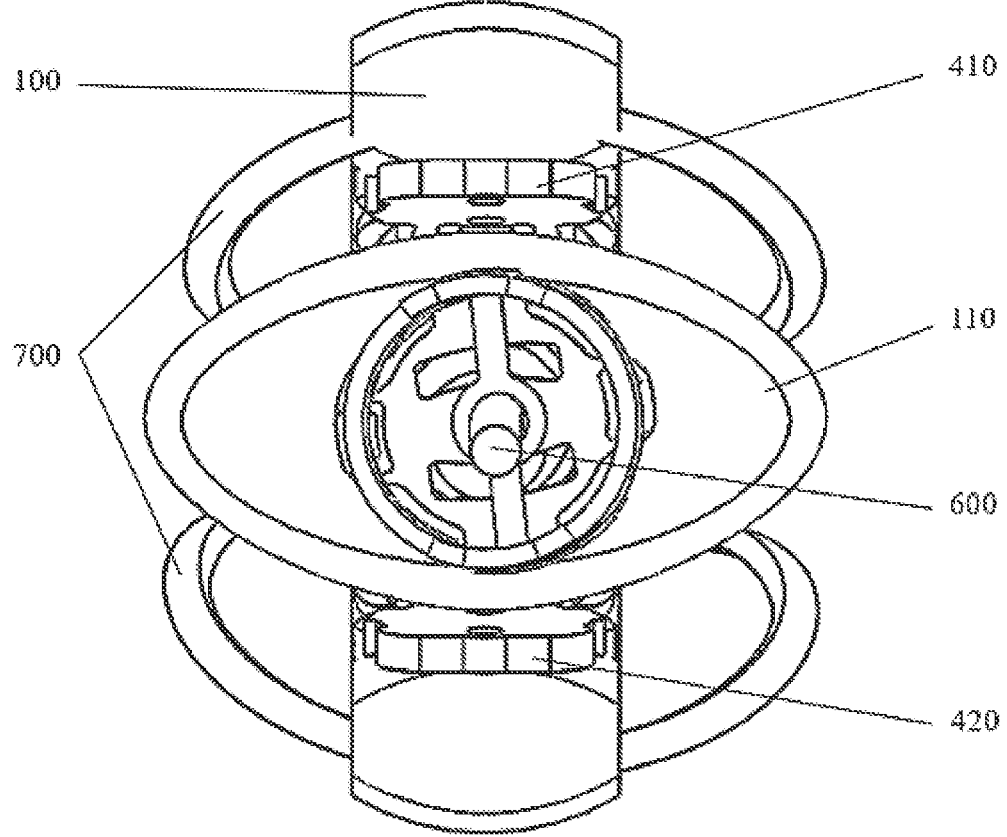
FIG. 3 is a schematic diagram illustrating a top view of a tissue clamping device according to some embodiments of the present disclosure.
Figure 4:
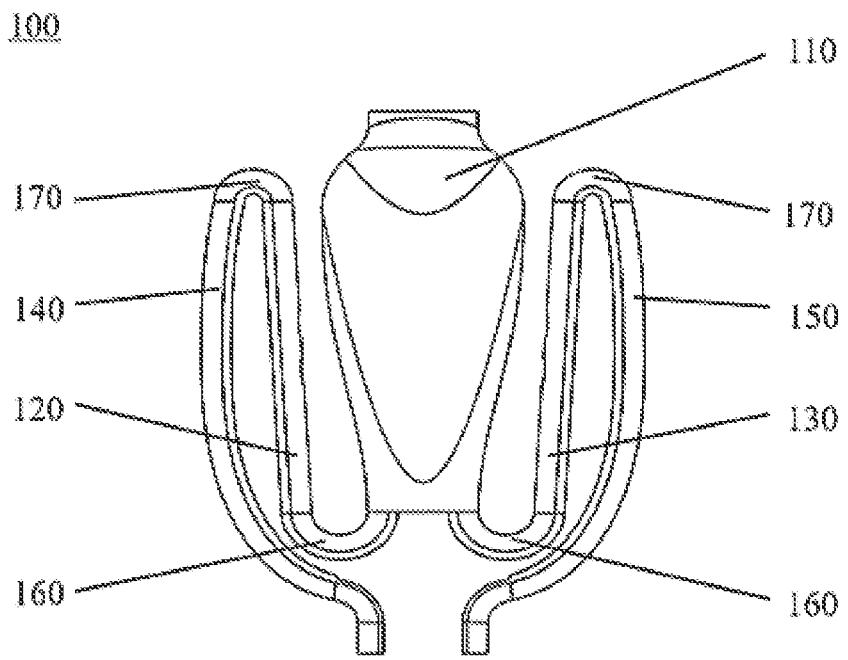
FIG. 4 is a structural schematic diagram illustrating a clamp of a tissue clamping device according to some embodiments of the present disclosure.
Figure 5:
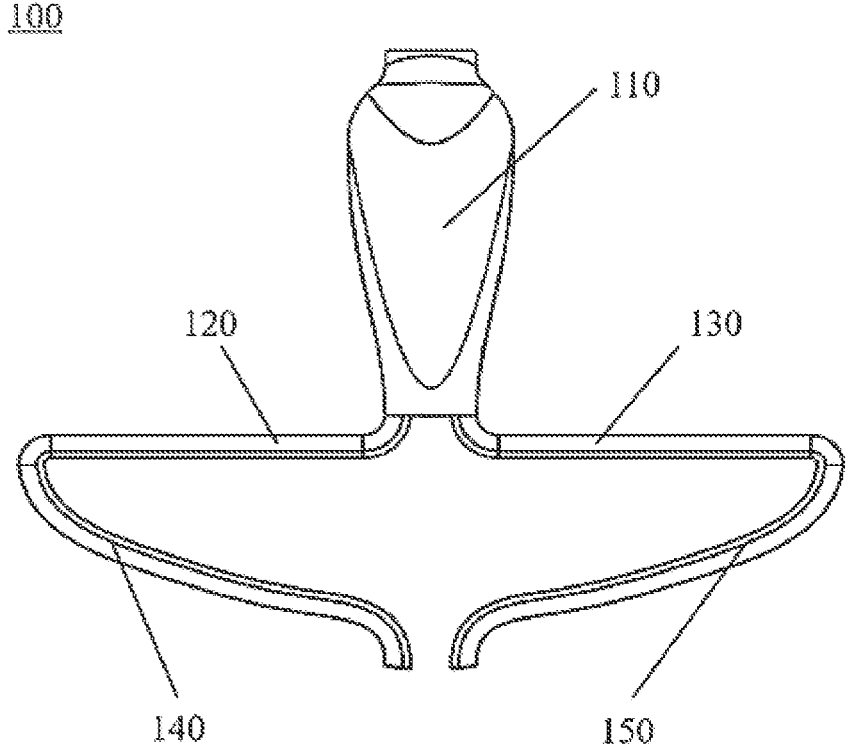
FIG. 5 is a structural schematic diagram illustrating a clamp of a tissue clamping device according to some embodiments of the present disclosure.
Figure 6:
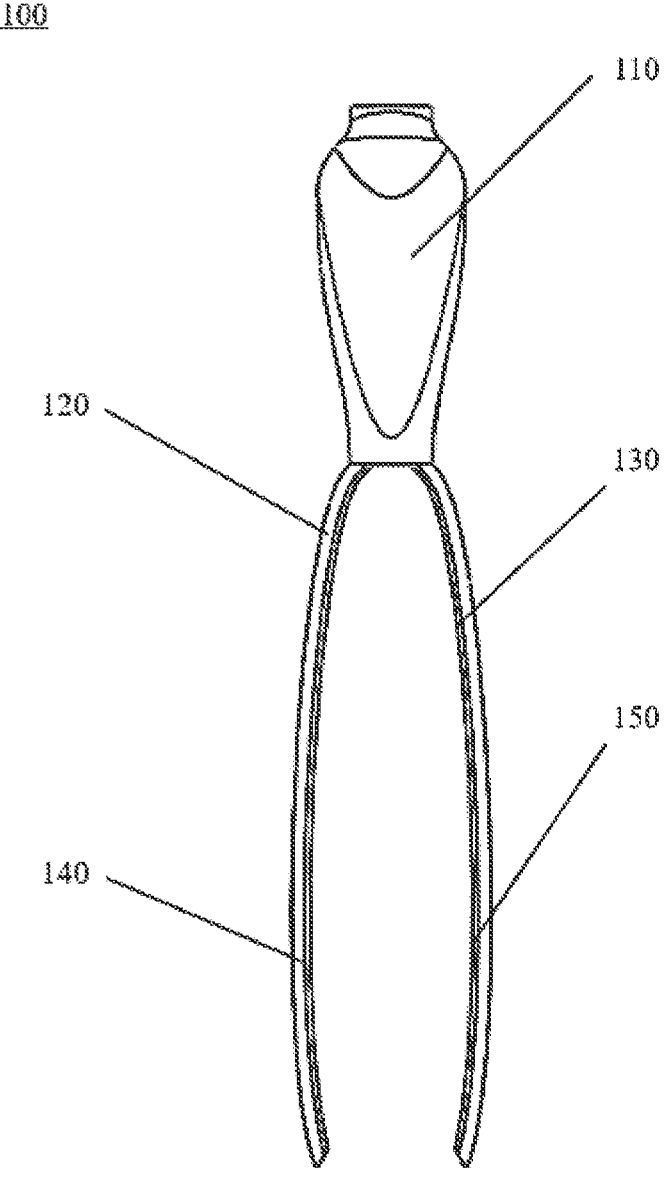
FIG. 6 is a structural schematic diagram illustrating a clamp of a tissue clamping device according to some embodiments of the present disclosure.
Figure 7:
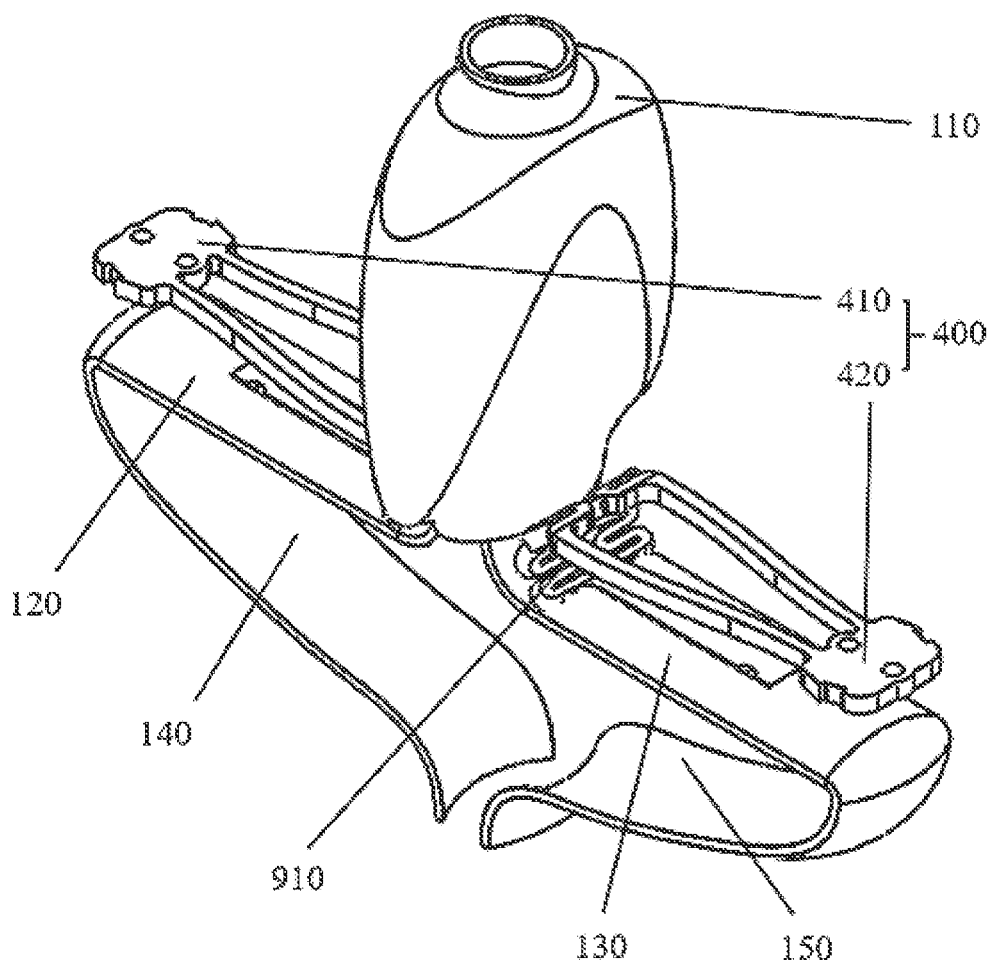
FIG. 7 is a schematic diagram illustrating a connection of a clamp and clips of a tissue clamping device according to some embodiments of the present disclosure.

FIG. 1 is a structural schematic diagram illustrating a tissue clamping device according to some embodiments of the present disclosure. FIG. 2 is a structural schematic diagram illustrating a tissue clamping device in a folded state according to some embodiments of the present disclosure. FIG. 3 is a schematic diagram illustrating a top view of a tissue clamping device according to some embodiments of the present disclosure. FIG. 4 is a structural schematic diagram illustrating a clamp of a tissue clamping device in a folded state according to some embodiments of the present disclosure. FIG. 5 is a structural schematic diagram illustrating a clamp of a tissue clamping device in an expanded state according to some embodiments of the present disclosure. FIG. 6 is a structural schematic diagram illustrating a clamp of a tissue clamping device in an expanded state according to some embodiments of the present disclosure. FIG. 7 is a schematic diagram illustrating a connection of a clamp and clips of a tissue clamping according to some embodiments of the present disclosure. A clamp of a tissue clamping device disclosed in the present disclosure will be described in detail with reference to FIGS. 1-7. It should be noted that the following embodiments are merely illustrative of the present disclosure, and not intended to limit the present disclosure.

As shown in FIGS. 1-7, a tissue clamping device may include a clamp 100, a first connector 200, a second connector 300, and a clip 400. The clamp 100 may include a supporting unit 110, a first interior clamping arm 120, a first exterior clamping arm 140, a second interior clamping arm 130, and a second exterior clamping arm 150. A first side of the supporting unit 110 may be connected to the first interior clamping arm 120 and the first exterior clamping arm 140 in sequence via a bendable connection. A second side of the supporting unit 110 may be connected to the second interior clamping arm 130 and the second exterior clamping arm 150 in sequence via a bendable connection. The bendable connection used to connect the supporting unit 110, the first interior clamping arm 120 may refer that a first connection part connecting the first interior clamping arm 120 and the supporting unit 110 may be bendable. The bendable connection used to connect the supporting unit 110 and the second interior clamping arm 130 may refer that a second connection part connecting the second interior clamping arm 130 and the supporting unit 110 may be bendable. The first interior clamping arm 120 may be bent in a direction from the first interior clamping arm 120 to the supporting unit 110, and the second interior clamping arm 130 may be bent in a direction from the second interior clamping arm 130 to the supporting unit 110, such that the first interior clamping arm 120 and the second interior clamping arm 130 may be folded relative to each other. The first interior clamping arm 120 may be bent in a direction from the supporting unit 110 to the first interior clamping arm 120, and the second interior clamping arm 130 may be bent in a direction from the supporting unit 110 to the second interior clamping arm 130, such that the first interior clamping arm 120 and the second interior clamping arm 130 may be expanded relative to each other. The first interior clamping arm 120 may be connected to the first exterior clamping arm 140 via a bendable connection. The second interior clamping arm 130 may be connected to a second exterior clamping arm 150 via a bendable connection. The bendable connection used to connect the first interior clamping arm 120 and first exterior clamping arm 140 or the bendable connection connect the second interior clamping arm 130 and second exterior clamping arm 150 may refer to that a third connection part between the first interior clamping arm 120 and the first exterior clamping arm 140 and/or a fourth connection part between the second interior clamping arm 130 and the second exterior clamping arm 150 may be bendable, and an angle between the first interior clamping arm 120 and the first exterior clamping arm 140 may be changed and/or and an angle between the second interior clamping arm 130 and the second exterior clamping arm 150 may be changed. In some embodiments, a count of interior clamping arm(s) and/or exterior clamping arm(s) may be determined according to different conditions. For example, the interior clamping arms may also include a third interior clamping arm and a fourth interior clamping arm. The exterior clamping arms may also include a third exterior clamping arm and a fourth exterior clamping arm. The supporting unit 110, the third interior clamping arm, and the third exterior clamping arm may be connected in sequence via a bendable connection. The supporting unit 110, the fourth interior clamping arm, and the fourth exterior clamping arm may be connected in sequence via a bendable connection.

In some embodiments, the clamp 100 may be integrally formed. Specifically, in a manufacturing process of the clamp 100, the clamp 100 may be produced by cutting a metal tube, for example, using a laser. In some alternative embodiments, the clamp 100 may be produced by weaving a metal wire. The clamp 100 may be connected to the first connector 200 and the second connector 300, and between the first connector 200 and second connector 300. A relative movement of the first connector 200 and the second connector 300 may drive the first interior clamping arm 120 and the second interior clamping arm 130 to be expanded or folded relatively. A relative folded state of the first interior clamping arm 120 and the second interior clamping arm 130 may be described in FIG. 4. An expanding angle between the first interior clamping arm 120 and the second interior clamping arm 130 may be various, for example, 40°, 90°, 120°, 180°, 270°, 350°, 360°, etc. As shown in FIG. 5, the expanding angle between the first interior clamping arm 120 and the second interior clamping arm 130 may be 180°. The expanding angle between the first interior clamping arm 120 and the second interior clamping arm 130 may be substantially 360° as shown in FIG. 6. In some embodiments, as shown in FIGS. 1-2, a first end of the supporting unit 110 (e.g., an upper end as shown in FIGS. 1-2) may be connected to the first connector 200, for example, via a fixed connection mode. A first end of the first exterior clamping arm 140 (e.g., a lower end shown in FIGS. 1-2) and a first end of the second exterior clamping arm 150 (e.g., a lower end as shown in FIGS. 1-2) may be respectively connected to the second connector 300, for example, via a fixed connection mode. According to such configuration mentioned above, when the second connector 300 moves relative to the first connector 200, the second connector 300 may move relative to the supporting unit 110. When the second connector 300 moves away from the supporting unit 110, a movement of the first exterior clamping arm 140 and second exterior clamping arm 150 may respectively drive the first interior clamping arm 120 and the second interior clamping arm 130 to be expended relative to each other. In some embodiments, a first end of the first exterior clamping arm 140 and a first end of the second exterior clamping arm 150 may be connected to the second connector 300 via a bendable connection mode, which may cause the first interior clamping arm 120 and the second interior clamping arm 130 to be expended relatively to form a relatively large angle.

In some embodiments, as shown in FIG. 7, the clip 400 may include a first clip 410 disposed on the first interior clamping arm 120 and a second clip 420 disposed on the second interior clamping arm 130. The first clip 410 and the second clip 420 may be expanded and folded relative to the first interior clamping arm 120 and the second interior clamping arm 130, respectively. Tissues may be clamped between the first clip 410 and the first interior clamping arm 120 and between the second clip 420 and the second interior clamping arm 130. In some embodiments, the clip 400 may be an agnail clip or other types of clips. For example, a side of the clip 400 facing an interior clamping arm (e.g., the first interior clamping arm 120 or the second interior clamping arm 130) may include barbs and/or protrusions, etc.

In some embodiments, the tissue clamping device may further include a first control mechanism which may be configured to control a movement of the second connector 300 relative to the first connector 200, thereby controlling the first interior clamping arm 120 and the second interior clamping arm 130 to be folded or expanded relative to each other. The first control mechanism may include a brake lever 600 which may pass through the supporting unit 110 and connected to the second connector 300 via a detachable connection mode (e.g., a screw connection mode). The brake lever 600 may push and pull the second connector 300 to drive the second connector 300 to be moved relative to the first connector 200. In some embodiments, the tissue clamping device may further include a second control mechanism which may be configured to drive the first clip 410 and the second clip 420 to be expanded or folded relative to the first interior clamping arm 120 and the second interior clamping arm 130, respectively. The second control mechanism may include a first pulling cable which may be connected to the first clip 410 and a second pulling cable which may be connected to the second clip 420. For example, the first pulling cable may be connected to a through-hole of an expanding and folding end of the first clip 410, and the second pulling cable may be connected to a through-hole of an expanding and folding end of the second clip 420. The first clip 410 and the second clip 420 may possess prefabricated resilience force which may be used to pull the first clip 410 and the second clip 420 to the first interior clamping arm 120 and the second interior clamping arm 130, respectively. When the first pulling cable and/or the second pulling cable are pulled, the first clip 410 and/or the second clip 420 may be expanded relative to the first interior clamping arm 120 and the second interior clamping arm 130, respectively under pulling force of the pulling cables. When the first pulling cable and/or the second pulling cable are loosened, the first clip 410 may be folded to the first interior clamping arm 120 under an action of the prefabricated resilience force, and/or the second clip 420 may be folded to the second interior clamping arm 130 under the action of the prefabricated resilience force.

In some embodiments, the first side of the supporting unit 110 may be connected to the first interior clamping arm 120 via a first bending structure 160, and the second side of the supporting unit 110 may be connected to the second interior clamping arm 130 via the first bending structure 160. The first bending structure 160 may be a first S rod (e.g., an S rod 910) or a first thin waist bending structure (e.g., a thin waist bending structure 920). The first interior clamping arm 120 may be connected to the first exterior clamping arm 140 via a second bending structure 170. The second interior clamping arm 130 may be connected to the second exterior clamping arm 150 via a second bending structure 170. The second bending structure 170 may include the S rod 910, the thin waist bending structure 920, or the like. Due to structural and/or material characteristics, the first bending structure 160 and the second bending structure 170 may be bent. A structure of the first bending structure 160 may be the same as or different from that of the second bending structure 170. For example, the first bending structure 160 may include the S rod 910, the second bending structure 170 may include the S rod 910 or the thin waist bending structure 920. The S rod 910 and the thin waist bending structure 920 may be performed a heating operation. The S rod 910 and the thin waist bending structure 920 may be deformed during/after the heating operation. A bending part of the S rod 910 and the thin waist bending structure 920 may share a stress uniformly, which may improve a bending performance of the S rod 910 and the thin waist bending structure 920, thereby extending a service life of the clamp 100.

Figure 8:
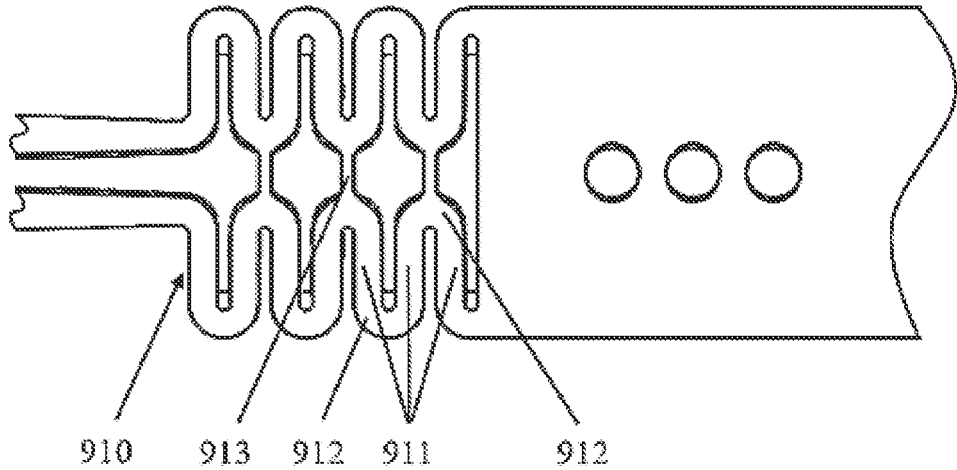
FIG. 8 is a structural schematic diagram illustrating an S rod of a clamp of a tissue clamping device according to some embodiments of the present disclosure.
Figure 9:
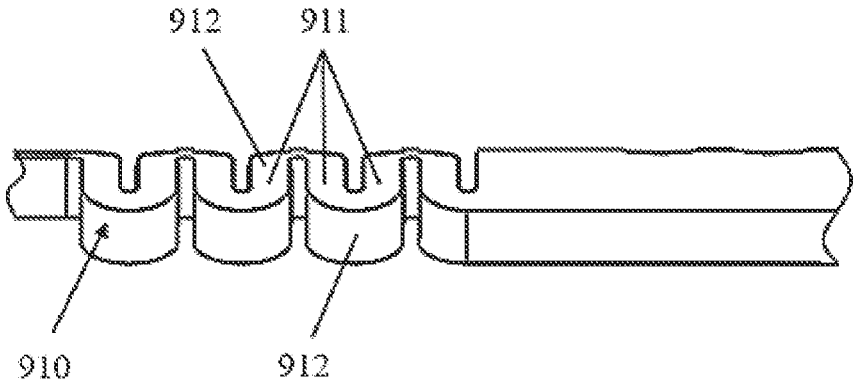
FIG. 9 is a schematic diagram illustrating a side view of an S rod of a clamp of a tissue clamping device according to some embodiments of the present disclosure.
Figure 10:
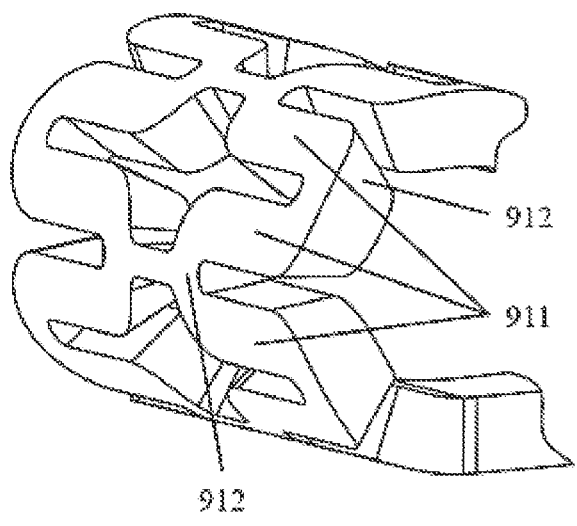
FIG. 10 is a schematic diagram illustrating an S rod of a clamp of a tissue clamping device in a bendable state according to some embodiments of the present disclosure.

FIG. 8 is a structural schematic diagram illustrating a front view of an S rod of a clamp of a tissue clamping device according to some embodiments of the present disclosure. FIG. 9 is a schematic diagram illustrating a side view of an S rod of a clamp of a tissue clamping device according to some embodiments of the present disclosure. FIG. 10 is a schematic diagram illustrating an S rod of a clamp of a tissue clamping device in a bendable state according to some embodiments of the present disclosure. As shown in FIGS. 8-10, the S rod 910 refers to a bendable rod structure which presents a shape of "S". In some embodiments, the S rod 910 may at least include three straight rods 911 and two curved rods 912. The three straight rods 911 may be parallel to each other, and the three straight rods 911 may be arranged in sequence. Two ends of each two adjacent straight rods of the three straight rods 911 may be connected, and the two ends of each two adjacent straight rods of the three straight rods 911 may be located at a same side of the S rod 910. The two ends of each two adjacent straight rods of the three straight rods 911 may be connected via one of the two curved rods 912. A row (e.g., a lower row shown in FIG. 8) of the S rod 910 shown in FIGS. 8-9 may include seven straight rods 911 and six curved rods 912. The seven straight rods 911 may be parallel to each other, and the seven straight rods 911 may be arranged in sequence. Two ends of each two adjacent straight rods of the seven straight rods 911 may be connected, and the two ends may be located at a same side of the S rod 910. The two ends of each two adjacent straight rods of the seven straight rods 911 may be connected via one of the six curved rods 912. In some embodiments, a count of the straight rod(s) 911 and/or the curved rod(s) 912 may be determined according to different conditions, which may be not limited herein. FIG. 10 illustrates a bent S rod 910. FIGS. 8-9 illustrate S rods 910 which are not bent. As shown in FIG. 10, when the S rod 910 is bent, the straight rods 911 may be parallel to each other, and the S rod 910 may be bent at each of the curved rods 912. With such configuration mentioned above, the S rod 910 may be bent relatively easily. In some embodiments, the S rod 910 may be arranged in one or more rows (e.g., 2 rows, 3 rows, etc.). As shown in FIG. 8, the S rod 910 may be arranged with an upper row and a lower row. The one or more rows of the S rod 910 may improve the stability of the S rod 910 to avoid lateral bending of the S rod 910, and twisting between straight rods 911. As shown in FIG. 8, in some embodiments, when the S rod 910 is arranged in one or more rows, the curved rods 912 disposed between two adjacent rows of S rods 910 may be connected via a connecting rod 913. The connecting rod 913 that are configured to connect two adjacent rows of the S rods 910 may effectively improve the stability of the S rod 910 when the S rod 910 is bent. In some embodiments, the S rod 910 may be produced by cutting a shape-memory alloy plate or a shape-memory alloy tube. The S rod 910 may have prefabricated resilience force after being performed a heating and shaping operation, thereby improving the bending performance, the resilience performance, and the fatigue resistance performance of the S rod 910.

Figure 11:
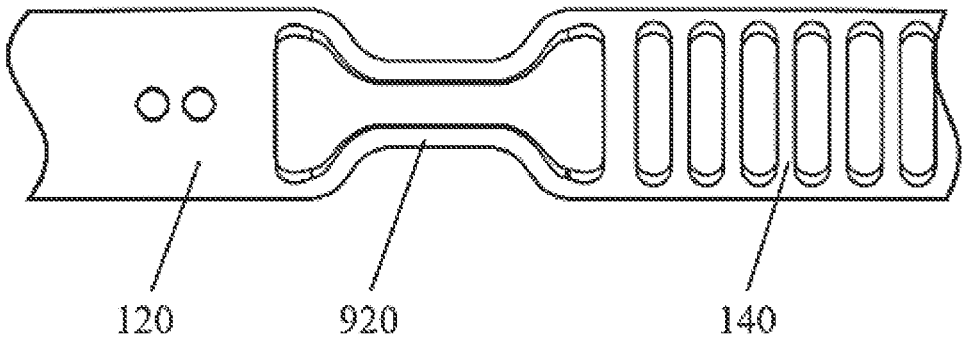
FIG. 11 is a schematic diagram illustrating a thin waist bending structure of a clamp of a tissue clamping device according to some embodiments of the present disclosure.

FIG. 11 is a schematic diagram illustrating a thin waist bending structure of a clamp of a tissue clamping device according to some embodiments of the present disclosure. As shown in FIG. 11, the first interior clamping arm 120 and the first exterior clamping arm 140 may be connected via the thin waist bending structure 920. The thin waist bending structure 920 refers to a bendable rod-like structure with a middle portion and at least two ends, and a width of the middle portion is smaller than a width of each of at least two ends of the thin waist bending structure 920, that is, the thin waist bending structure 920 may present a shape of thin waist, thereby improving the bending performance of the thin waist bending structure 920. In some embodiments, the thin waist bending structure 920 may be cut from a shape-memory alloy plate or a shape-memory alloy tube. The thin waist bending structure 920 may have prefabricated resilience force after being performed a heating and shaping operation. In some alternative embodiments, the thin waist bending structure 920 may include a bending structure (e.g., the second bending structure 170 shown in FIG. 15) with a middle portion and at least two ends, and a cross-sectional area of the middle portion may be smaller than a cross-sectional area of each of at least two ends.

Figures 12, 13:
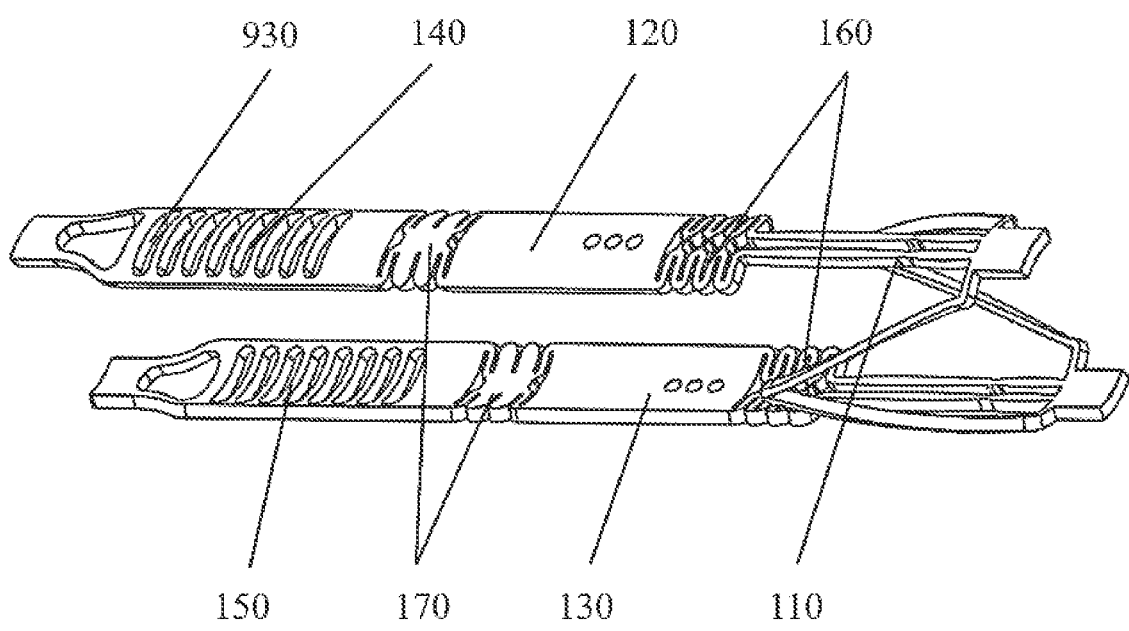
FIG. 12 is a structural schematic diagram illustrating a clamp of a tissue clamping device structure according to some embodiments of the present disclosure.
FIG. 13 is a schematic diagram illustrating a side view of a clamp of a tissue clamping device according to some embodiments of the present disclosure.
Figure 14:
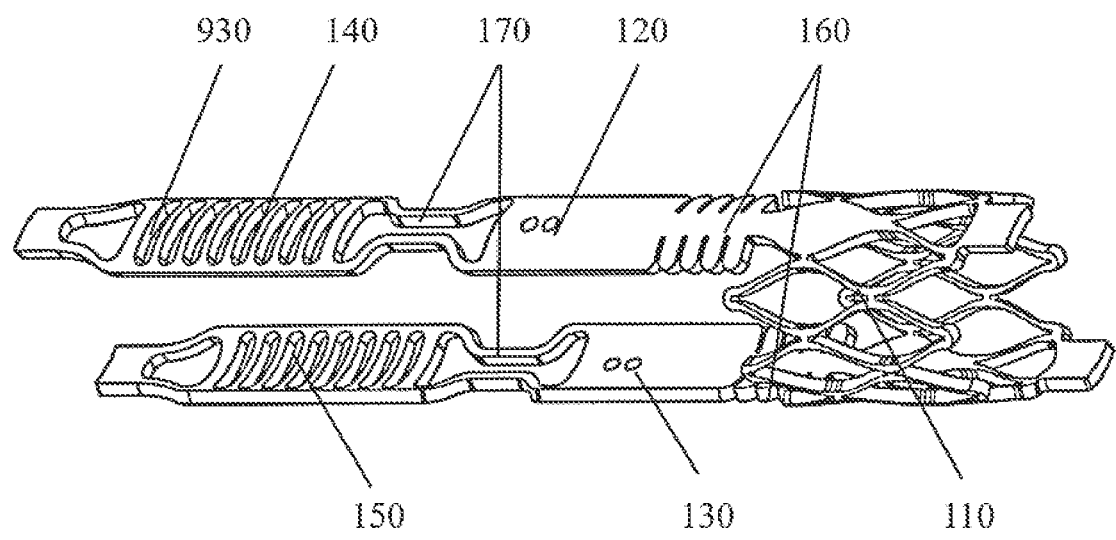
FIG. 14 is a structural schematic diagram illustrating a clamp of a tissue clamping device according to other embodiments of the present disclosure.
Figure 15:
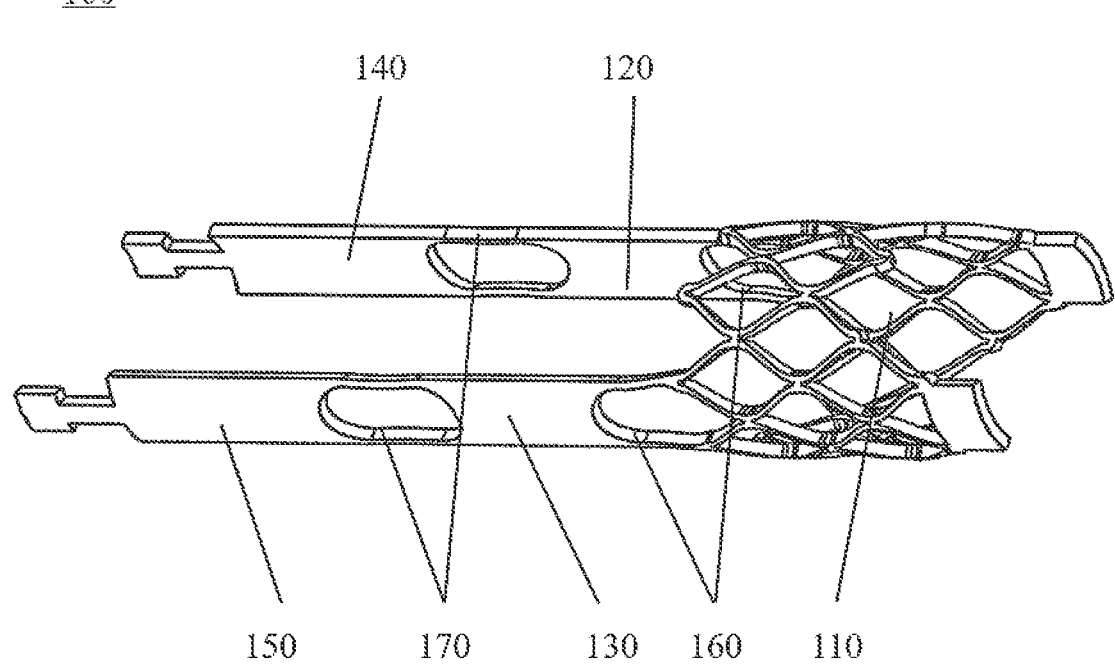
FIG. 15 is a structural schematic diagram illustrating a clamp of a tissue clamping device according to some embodiments of the present disclosure.

FIG. 12 is a structural schematic diagram illustrating a clamp of a tissue clamping device structure according to some embodiments of the present disclosure. FIG. 13 is a schematic diagram illustrating a side view of the clamp of the tissue clamping device shown in FIG. 12 according to some embodiments of the present disclosure. FIG. 14 is a structural schematic diagram illustrating a clamp of a tissue clamping device according to some embodiments of the present disclosure. FIG. 15 is a structural schematic diagram illustrating a clamp of a tissue clamping device according to some embodiments of the present disclosure. In some embodiments, as shown in FIGS. 12-15, the supporting unit 110 may include a grid structure. The grid structure may include a rhombus grid structure, a circular grid structure, a rectangular grid structure, a square grid structure, a triangular grid structure, a regular polygon grid structure, or the like, or any combination thereof. In some embodiments, the grid structure may affect a hardness of the supporting unit 110, and those skilled in the art may determine a size and/or a shape of the grid structure according to a hardness requirement of the supporting unit 110. For example, the triangular grid and/or a grid structure with a relatively small size may be used to improve the hardness of the supporting unit 110. As another example, the regular polygon grid and/or a grid structure with a relatively large size may be used to reduce the hardness of the supporting unit 110. The grid structure may improve the resilience performance of the supporting unit 110 so that the tissue clamping device can pass through a conveying tube when the tissue clamping device is conveyed. In addition, the supporting unit 110 may effectively fill a space between the first interior clamping arm 120 and the second interior clamping arm 130, which may prevent a formation of thrombus after the tissue clamping device clamps tissues.

In some embodiments, a shape of a cross-sectional of the supporting unit 110 may include a circle, an ellipse, etc. A cross-sectional area of the middle portion of the supporting unit 110 may be larger than a cross-sectional area of each of the two ends thereof. The cross section may include a plane perpendicular to the brake lever 600. For example, a shape of the supporting unit 110 may include a spherical, an ellipsoidal, etc. The supporting unit 110 may not cause damage to the tissues, and the supporting unit 110 may improve the efficiency of conveying the tissue clamping device to the tissues, and may effectively form a support for the tissue clamped by the tissue clamping device. In some embodiments, the shape of the supporting unit 110 may include a pear-like shape, a cylinder, or the like. The shape of the supporting unit 110 of the clamp 100 may be determined based on a condition of the tissues (e.g., a shape of a mating edge of the mitral leaflet) to improve a clamping performance of the clamp 100.

In some embodiments, as shown in FIGS. 12 and 14, the first exterior clamping arm 140 and the second exterior clamping arm 150 may include a plurality of through-holes 930 which may respectively affect deformations of the first exterior clamping arm 140 and the second exterior clamping arm 150 during the heating operation. In some embodiments, each of the plurality of through-holes 930 disposed on the first exterior clamping arm 140 may extend along a direction of a width of the first exterior clamping arm 140 or each of the plurality of through-holes 930 disposed on the second exterior clamping arm 150 may extend along a direction of a width of the second exterior clamping arm 150. The plurality of through-holes 930 may be arranged at intervals along a direction of a length of the first exterior clamping arm 140 and along a direction of a length of the second exterior clamping arm 150. In some alternative embodiments, the plurality of through-holes 930 may include other shapes and/or may be arranged in other manners. For example, the plurality of through-holes 930 may include square holes, round holes, polygonal holes, or the like, or any combination thereof. As another example, the plurality of through-holes 930 may be arranged in one or more rows along the directions of the width of the first exterior clamping arm 140 and/or the directions of the width of the second exterior clamping arm 150. In some embodiments, when the first interior clamping arm 120 and the second interior clamping arm 130 are folded, the first exterior clamping arm 140 and the second exterior clamping arm 150 may be bent and deformed into a circular arc shape (as shown in FIGS. 4-5) along a length direction of the first exterior clamping arm 140 and the second exterior clamping arm 150, respectively, after the heating operation, thereby effectively surrounding the supporting unit 110, the first interior clamping arm 120, and/or the second interior clamping arm 130.

In some embodiments, the clamp 100 may be integrally formed, for example, the clamp 100 may be produced by cutting and performing the heating operation on a shape-memory alloy tube. The shape-memory alloy tube may include a nickel-titanium alloy tube, a cobalt-chromium alloy tube, or the like, or any combination thereof. FIG. 13 is a schematic diagram illustrating a side view of the clamp as shown in FIG. 12. It can be seen from FIG. 13 that the clamp in FIG. 12 is integrally formed by cutting a pipe via a cutting mode, for example, a laser cutting, a water cutting, etc. Similarly, FIGS. 14-15 are schematic diagrams illustrating clamps which are integrally formed, respectively. Based on the clamp 100 shown in FIGS. 12-15, which may be integrally formed, one or more parts (e.g., the supporting unit 110, the first bending structure 160, the second bending structure 170, the first exterior clamping arm 140, the second exterior clamping arm 150, etc.) of the clamp 100 may be deformed during the heating operation of the clamp 100. For example, during the heating operation, two ends of supporting unit 110 may be folded inward, so that a cross-sectional area of a middle portion of the supporting unit 110 may be larger than a cross-sectional area of each of the two ends. As another example, the first exterior clamping arm 140 and the second exterior clamping arm 150 may be bent into an arc shape, and the first bending structure 160 and the second bending structure 170 may be bent during the heating operation. During the heating operation of the clamp 100, part(s) of the clamp 100 may be deformed using a mold. The shape-memory alloy may remember a shape (e.g., a shape shown in FIG. 4) which may be formed after a heating and shaping operation. When tissues are clamped, the clamp 100 may possess restoring force which may cause the clamp 100 to return to an original shape, thereby clamping the tissues tight. It should be noted that the clamp 100 shown in FIGS. 1-7 is merely used to illustrate an approximate shape of the clamp 100, and not intended to limit that the shape of the clamp is consistent with that shown in FIGS. 1-7. For example, the supporting unit 100 of the clamp 110 may include a grid structure based on the clamp 100 shown in FIGS. 1-7. The first bending structure 160 and the second bending structure 170 may include a first S rod (e.g., the S rod 910), a thin waist bending structure (e.g., the thin waist bending structure 920), etc.

Figure 16:
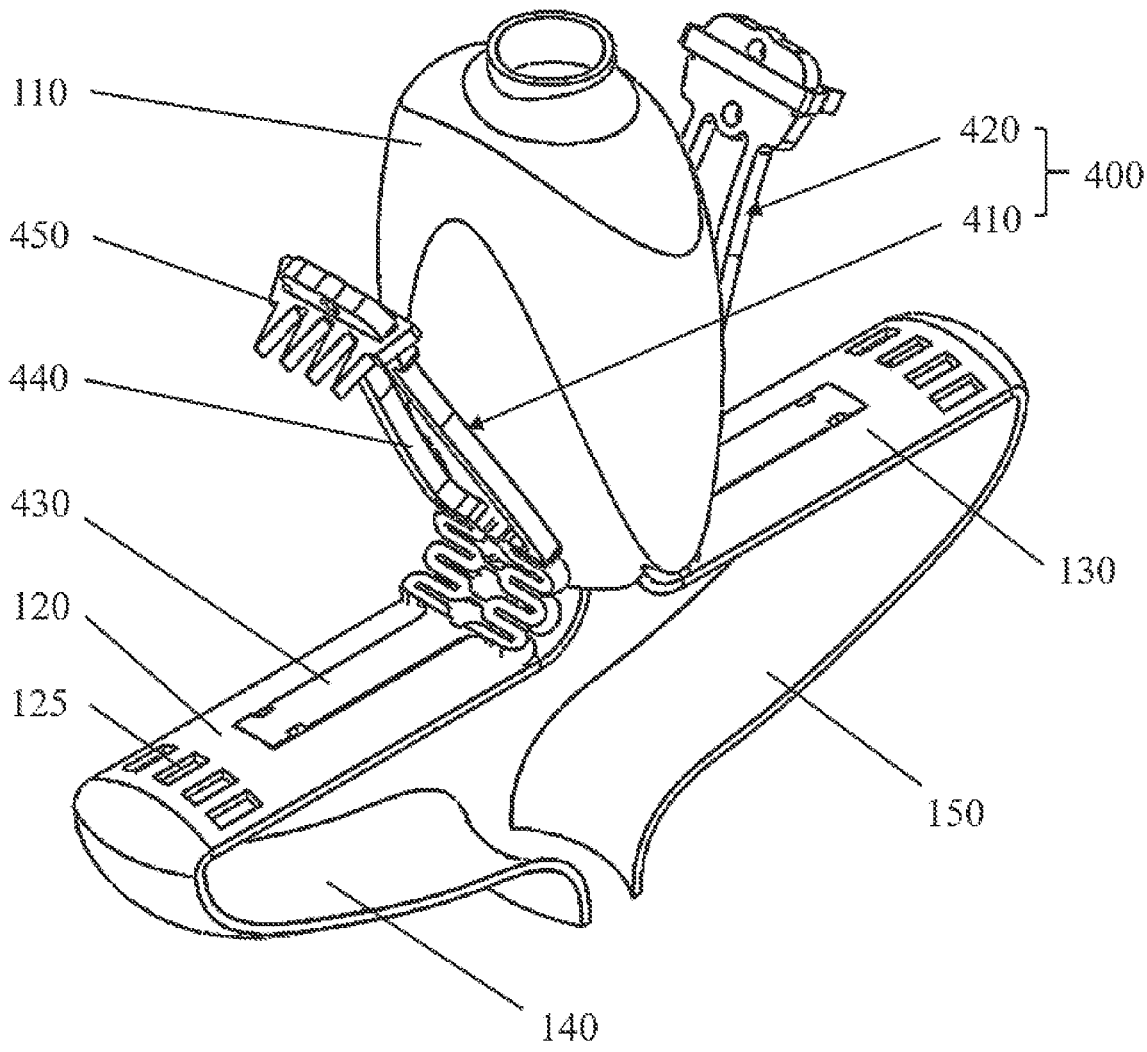
FIG. 16 is a schematic diagram illustrating a connection of a clamp and agnails of an agnail clip of a tissue clamping device according to some embodiments of the present disclosure.

In some embodiments, the clip 400 may include a first clip 410 disposed on the first interior clamping arm 120 and a second clip 420 disposed on the second interior clamping arm 130. The first clip 410 may be the same as the second clip 420. Specifically, the clip 400 may include a fixing unit 430 and a clipping unit 440. The fixing unit 430 may be connected to the clipping unit 440 through a bending unit. In some embodiments, the clip 400 may include an agnail clip. The agnail clip may include a fixing unit 430, a clipping unit 440, and an agnail 450. A first end of the clipping unit 440 may be connected to a first end of the fixing unit 430 via a bending unit. The agnail 450 may be disposed on a second end of the clipping unit 440. FIG. 16 is a schematic diagram illustrating a connection of a clamp and an agnail clip of a tissue clamping device according to some embodiments of the present disclosure. As shown in FIG. 16, the agnail 450 may be disposed on one side of the clipping unit 440 of the clip 400 (e.g., the first clip 410 or the second clip 420) of the clip 400, which may face an interior clamping arm (e.g., the first interior clamping arm 120 or the second interior clamping arm 130). The fixing unit 430 may be configured to fix the clip 400 on the interior clamping arm. The clipping unit 440 may be configured to clamp the tissues together with the interior clamping arm. A first end of the fixing unit 430 may be connected to a first end of the clipping unit 440 via a bending unit, so that the clip 400 may be expanded or folded relative to the interior clamping arm. The agnail 450 may effectively prevent tissues sliding from a space between the clip 400 and the interior clamping arm, thereby effectively improving the clamping stability of the tissue clamping device.

In some embodiments, the bending unit may be the S rod 910 (as shown in FIG. 19 and FIGS. 22-24). The S rod 910 may be deformed after being performed the heating operation. A bending part of the S rod 910 may share a stress uniformly, and which may be not easily broken after multiple times of bending. In addition, the S rod 910 may improve bending smoothly of the clip 400 and avoiding breaking the clip 400 when the clip 400 is bent. In some embodiments, the S rod 910 may at least include three straight rods 911 and two curved rods 912. The three straight rods 911 may be parallel to each other and arranged in sequence. Two ends of each two adjacent straight rods of the three straight rods 911 may be connected, and the two ends of each two adjacent straight rods of the three straight rods 911 may be located at a same side of the S rod 910. The two ends of each two adjacent straight rods of the three straight rods 911 may be connected via one of the two curved rods 912. More descriptions regarding the S rod 910 may be found elsewhere in the present disclosure. See, e.g., FIGS. 8-10, and the relevant descriptions thereof.

Figure 17:
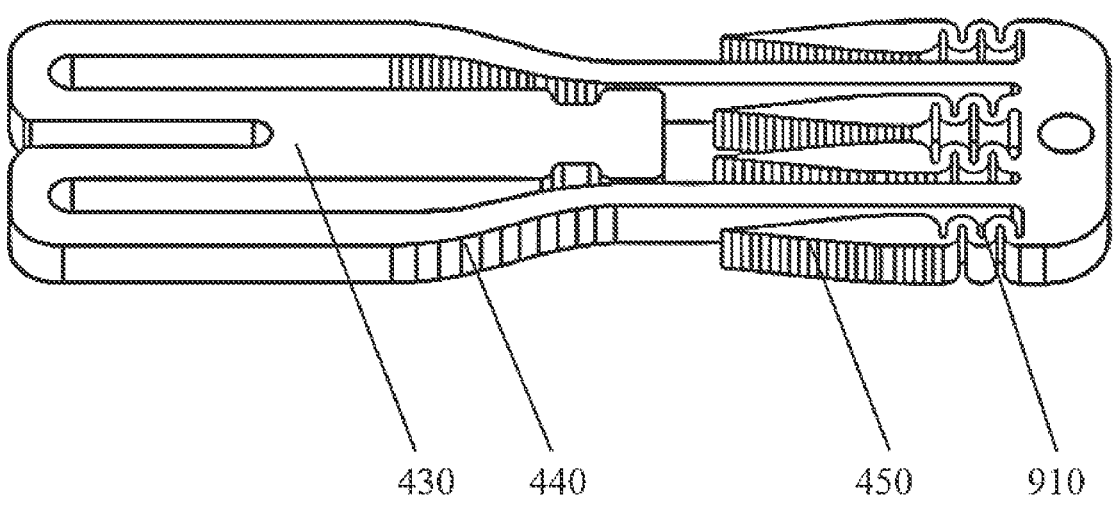
FIG. 17 is a structural schematic diagram illustrating an integrally formed agnail clip of a tissue clamping device according to some embodiments of the present disclosure.
Figure 18:
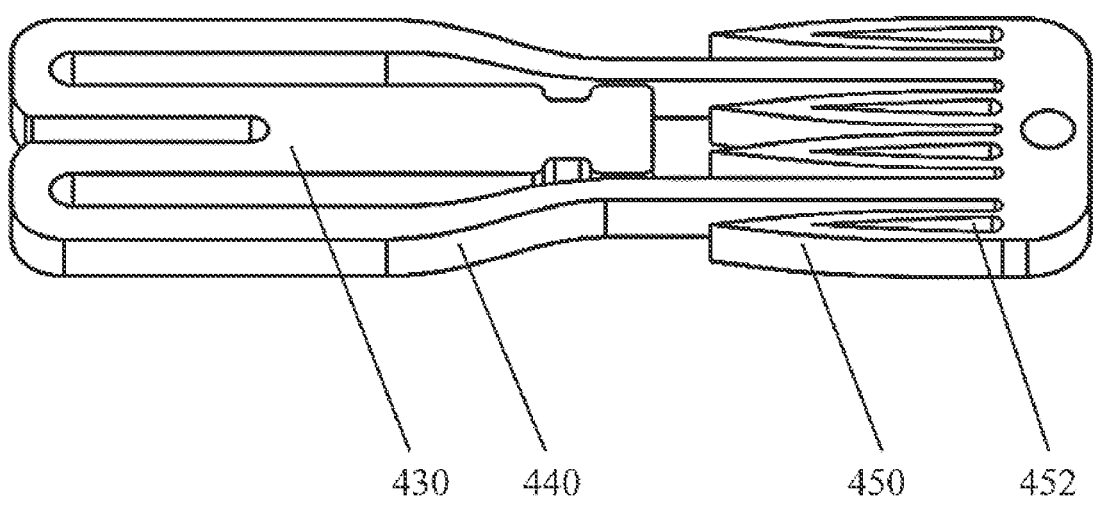
FIG. 18 is a schematic diagram illustrating an integrally formed agnail clip of a tissue clamping device according to other embodiments of the present disclosure.

In some embodiments, the fixing unit 430, the clipping unit 440, and the agnail 450 may be integrally formed. Specifically, the fixing unit 430, the clipping unit 440, and the agnail 450 may be integrally formed by cutting a plate or a tube (e.g., via a laser). The integral formation of the fixing unit 430, the clipping unit 440, and the agnail 450 may improve the stability of the agnail clip and reliability of connection(s) connecting component(s) of the fixing unit 430, the clipping unit 440, and the agnail 450, and reduce manufacture cost of components of a tissue clamping device. In some embodiments, the agnail 450 may include a plurality of agnail bars (e.g., three agnail bars, four agnail bars, five agnail bars, seven agnail bars, ten agnail bars, etc.). The plurality of agnail bars may be arranged in one or more rows. An exterior wall of an agnail bar may include a flat surface, a circular arc surface, etc. FIG. 17 is a structural schematic diagram illustrating an integrally formed agnail clip of a tissue clamping device according to some embodiments of the present disclosure. In some embodiments, at least one agnail bar may be connected to the second end of clipping unit 440 via an S rod 910. Preferably, as shown in FIG. 17, all of the agnail bars may be connected to the second end of the clipping unit 440 via the S rod 910. The S rod 910 may facilitate the bending of each of the agnail bars during the heating operation. For example, an agnail bar may be bent to 90° from the clipping unit 440. FIG. 18 is a schematic diagram illustrating an integrally formed agnail clip of a tissue clamping device according to other embodiments of the present disclosure. In some embodiments, as shown in FIG. 18, at least one agnail bar (e.g., all of the agnail bars) may include a through-hole 452. In some embodiments, the through-hole 452 may penetrate an agnail bar along a direction of a thickness of the agnail bar. Each of the agnail bars may include one or more through-holes. A shape of the through-hole(s) may include a thorn, a square, a circle, a triangle, etc. Preferably, each of the agnail bars may include a through-hole 452, and a shape of the through-hole 452 may be similar to a shape of the agnail bar. In a manufacturing process of the agnail clip, the through-hole(s) in the agnail chip may facilitate bend and formation of the at least one agnail bar during a heating operation. In some alternative embodiments, the through-hole(s) on each of the agnail bars may penetrate the agnail bar in other directions (e.g., a direction of a width of the agnail bar).

Figure 19:
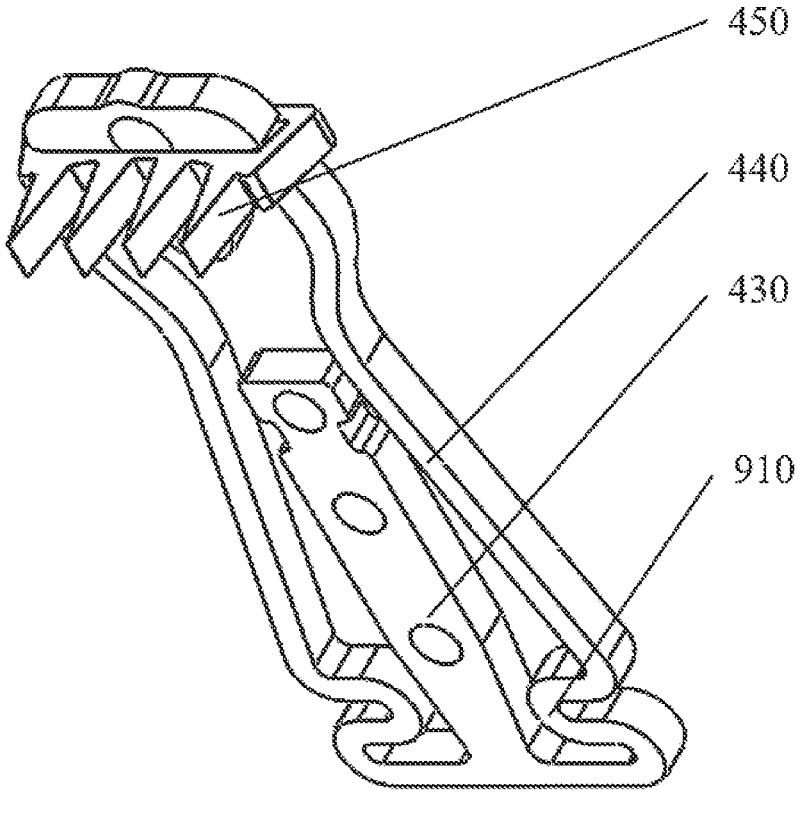
FIG. 19 is a structural schematic diagram illustrating a detachable connection of an agnail clip and a clamping unit of a tissue clamping device according to some embodiments of the present disclosure.
Figure 20:
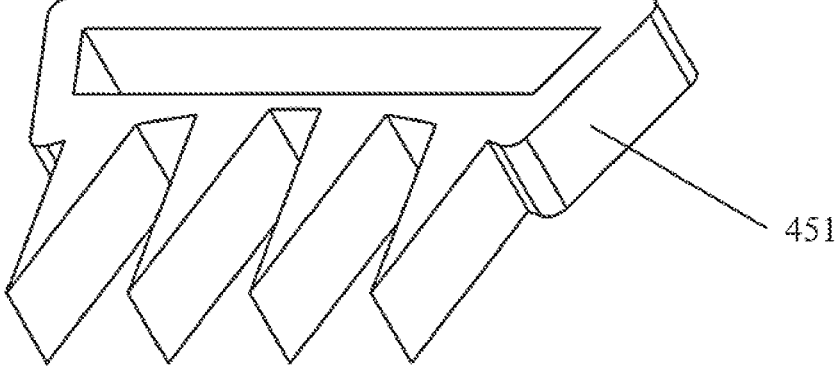
FIG. 20 is a structural schematic diagram illustrating agnails of an agnail clip of a tissue clamping device according to some embodiments of the present disclosure.
Figure 21:
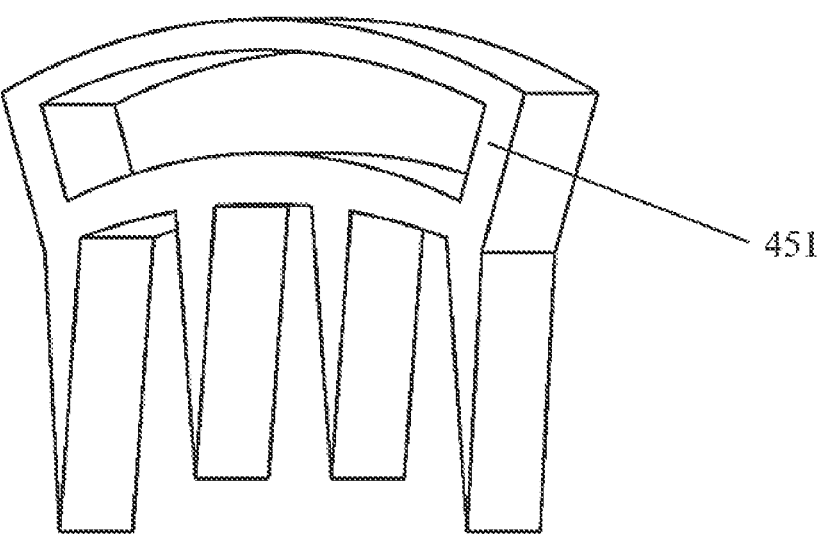
FIG. 21 is a structural schematic diagram illustrating agnails of an agnail clip of a tissue clamping device according to other embodiments of the present disclosure.

In some embodiments, the agnail 450 may be detachably connected to the second end of the clipping unit 440. Those skilled in the art may determine whether to dispose the agnail 450 on the clipping unit 440 according to an actual need, or determine which type of the agnail 450 is disposed on the clipping unit 440. FIG. 19 is a structural schematic diagram illustrating a detachable connection of agnails of an agnail clip and a clipping unit of a tissue clamping device according to some embodiments of the present disclosure. FIG. 20 is a schematic diagram illustrating agnails of an agnail clip of a tissue clamping device according to some embodiments of the present disclosure. FIG. 21 is a structural schematic diagram illustrating agnails of an agnail clip of a tissue clamping device according to some embodiments of the present disclosure. As shown in FIGS. 19-21, the second end of the clipping unit 440 may include a slot. The agnail 450 may include a snap ring 451, and the snap ring 451 may be connected to the slot, which may cause the agnail 450 to be easily and firmly disposed on the clipping unit 440. In addition, the agnail 450 may be detachably connected to the clipping unit 440, which may avoid that agnail bar(s) is difficult to be bent during the heating operation. In some embodiments, the snap ring 451 may be made of an elastic material or a super-elastic metal (e.g., a nickel-titanium alloy), thereby sleeving the snap ring 451 on the slot. In some embodiments, as shown in FIGS. 20-21, each of two opposite sides of the snap ring 451 may include a straight line, an arc, etc., which may match with the clipping unit 440 (e.g., a clipping unit cut from a plate, a clipping unit cut from a pipe, etc.). In some embodiments, a count, a shape, and an arrangement of the agnail bar(s) on the agnail 450 may be adjusted according to an actual condition (e.g., characteristics of clamped tissues, etc.).

Figure 22:
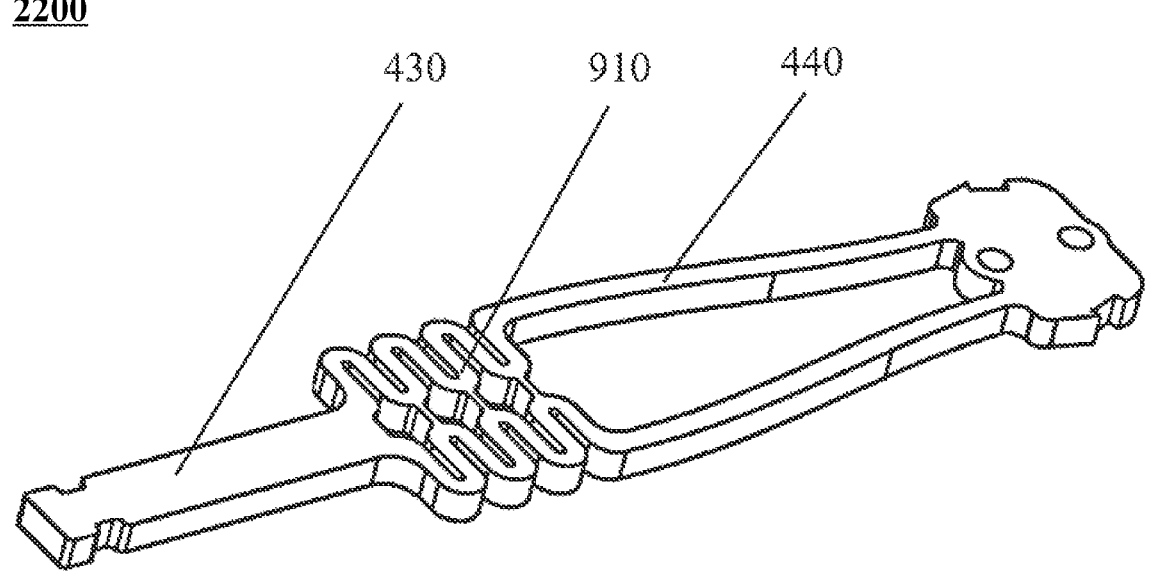
FIG. 22 is a schematic diagram illustrating a cutting shape of an agnail clip of a tissue clamping device according to some embodiments of the present disclosure.
Figure 23:
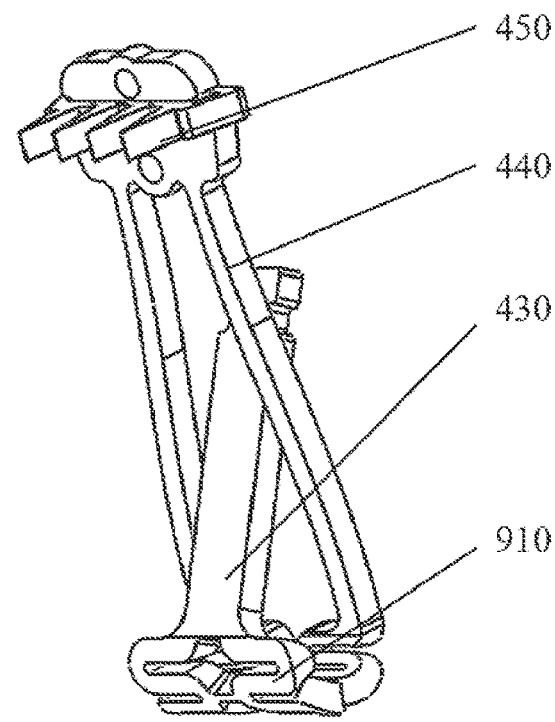
FIG. 23 is a structural schematic diagram illustrating an agnail clip of a tissue clamping device according to some embodiments of the present disclosure.
Figure 24:
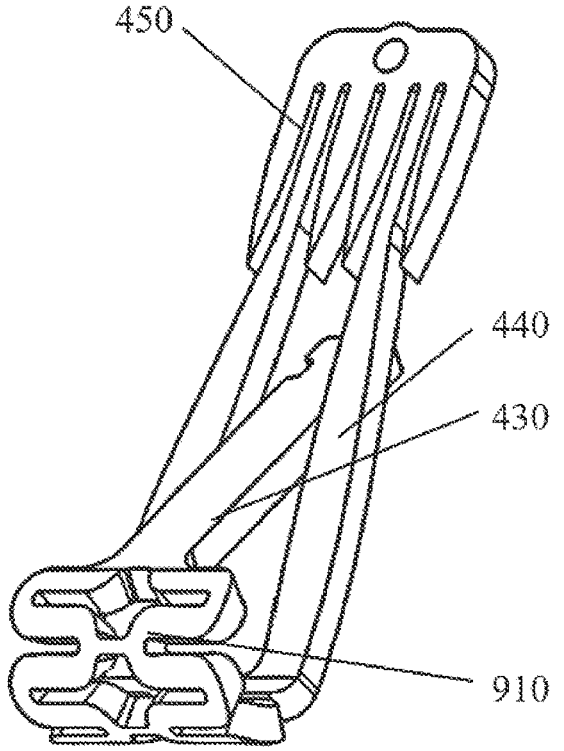
FIG. 24 is a structural schematic diagram illustrating an agnail clip of a tissue clamping device according to other embodiments of the present disclosure.

In some embodiments, the fixing unit 430 and/or the clipping unit 440 may be integrally formed by cutting and performing a treating and shaping operation on a shape-memory alloy. The shape-memory alloy may include a nickel-titanium alloy, a cobalt-chromium alloy, or the like, or any combination thereof. FIG. 22 is a schematic diagram illustrating a cutting shape of an agnail clip of a tissue clamping device according to some embodiments of the present disclosure. FIG. 23 is a structural schematic diagram illustrating an agnail clip of a tissue clamping device according to some embodiments of the present disclosure. FIG. 24 is a structural schematic diagram illustrating an agnail clip of a tissue clamping device according to other embodiments of the present disclosure. As shown in FIG. 22, an agnail clip 2200 may be integrally cut and formed from a shape-memory alloy plat. As shown in FIG. 23 and FIG. 24, a fixing unit 430 and a clipping unit 440 of the agnail clip 2200 which may be performed a heating and shaping operation may form a certain angle. In this case, a bending unit may have prefabricated resilience force, which may improve clamping force of the agnail clip 2200 and an interior clamping arm (e.g., the first interior clamping arm 120, the second interior clamping arm 130, etc.) to tissues. It should be noted that when the fixing unit 430 and the clipping unit 440 form the certain angle, the fixing unit 430 and the clipping unit 440 may be not parallel. Preferably, after being performed the heating and shaping operation, the fixing unit 430 may be bent into an interior hole of the clipping unit 440 (as shown in FIG. 23 and FIG. 24), that is, a turning angle of the fixing unit 430 relative to the clipping unit 440 during the heating and shaping operation may be greater than 180°. In some embodiments, those skilled in the art may determine the angle between the fixing unit 430 and the clipping unit 440 according to actual factors such as needed clamping force, a size of the tissue clamping device, or the like, or any combination thereof. For example, when the fixing unit 430 is bent into the interior hole of the clipping unit 440, the angle between the fixing unit 430 and the clipping unit 440 may be determined as 15°, 20°, 30°, etc.

Figure 47:
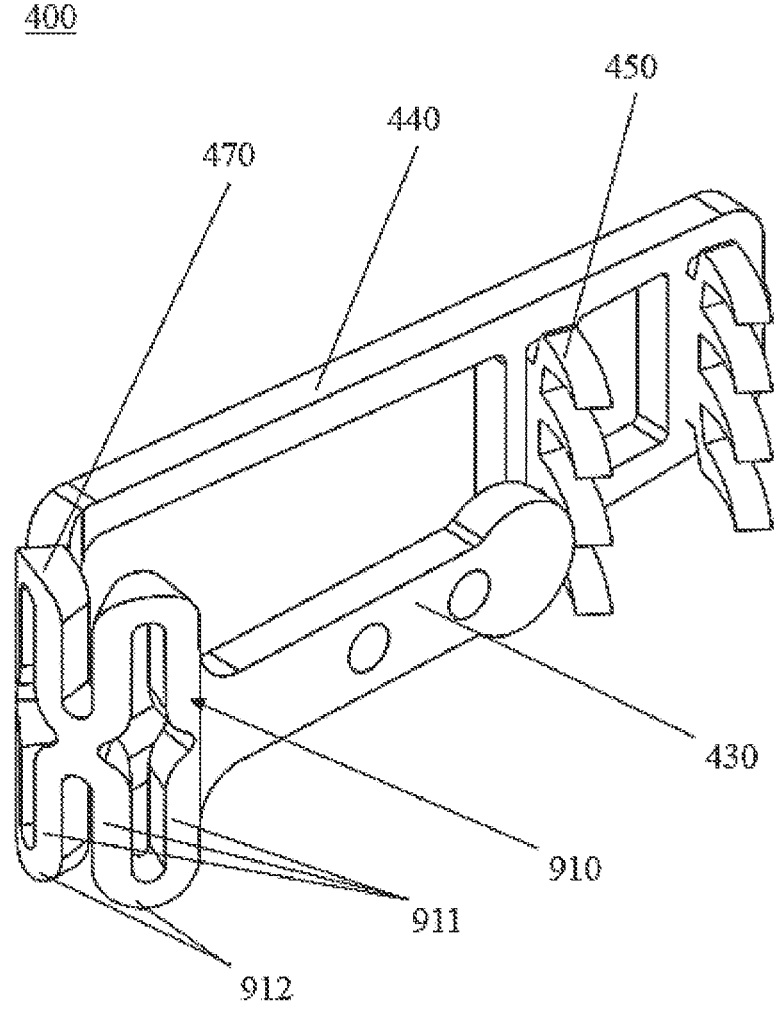
FIG. 47 is a schematic diagram illustrating a stereostructure of an agnail clip according to some embodiments of the present disclosure.
Figure 48:
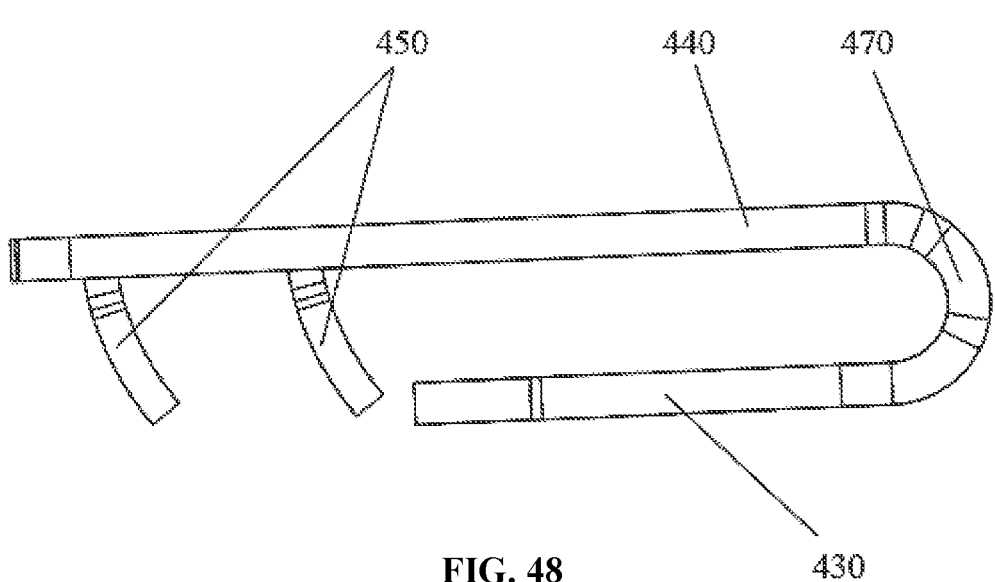
FIG. 48 is a schematic diagram illustrating a side view of an agnail clip according to some embodiments of the present disclosure.
Figure 49:
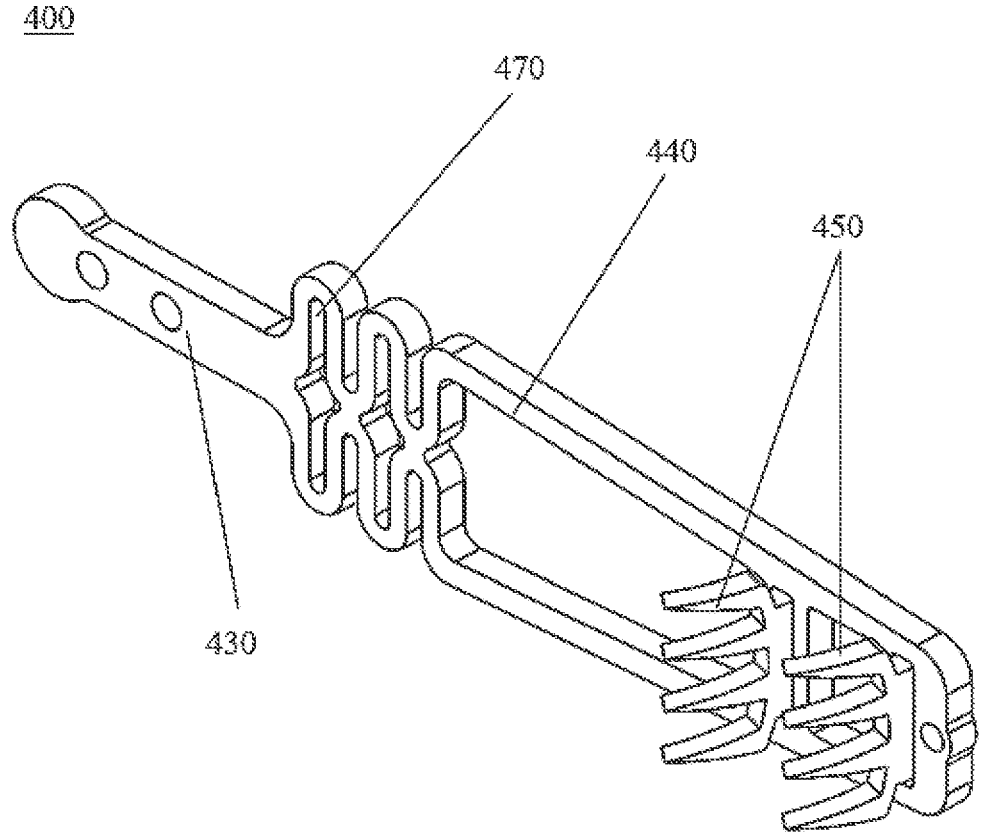
FIG. 49 is a structural schematic diagram illustrating an agnail clip disposed at a bending unit in an unbendable state according to some embodiments of the present disclosure.

FIG. 47 is a schematic diagram illustrating a stereostructure of an agnail clip according to some embodiments of the present disclosure. FIG. 48 is a schematic diagram illustrating a side view of an agnail clip according to some embodiments of the present disclosure. FIG. 49 is a structural schematic diagram illustrating an agnail clip disposed at a bending unit in an unbendable state according to some embodiments of the present disclosure. As shown in FIGS. 47-49, an agnail clip 400 may include a fixing unit 430, a clipping unit 440, and an agnail 450. A first end of the fixing unit 430 may be connected to a first end of the clipping unit 440 via a bending unit 470. The agnail 450 may be disposed on the clipping unit 440. The agnail 450 may include one or more agnail bars 454. A count of the agnail bars 454 may be one, two, five, eight, etc. The agnail bar(s) 454 may be arranged in one or more arrows. A shape of the agnail bar(s) 454 may include an arc. A concave side of the agnail bar(s) 454 may face the first end of the fixing unit 440, that is, a convex side of the agnail bar(s) 454 may face a second end of the clipping unit 440. The agnail clip 400 together with an interior clamping arm may be used to clamp tissues between the agnail clip 400 and the interior clamping arm. The fixing unit 430 may be configured to fix the agnail clip 400 on the interior clamping arm. FIG. 47 illustrates that the bending unit 470 is in an unbendable state. FIG. 49 illustrates that the bending unit 470 is in a bendable state. As shown in FIG. 47 and FIG. 49, the bending unit 470 may be bent so that the clipping unit 440 may be opened or closed relative to the interior clamping arm to clip the tissues when the clipping unit 440 is disposed on the agnail clip 400.

The agnail bars 454 of the arc shape may facilitate the agnail clip 400 inserting into or clipping the tissues and clamping the tissues tightly. In some embodiments, a radian of the agnail bars 454 may be 0°~30° (e.g., 5°, 10°, 15°, 25°, 30°, etc.)

Figure 50:
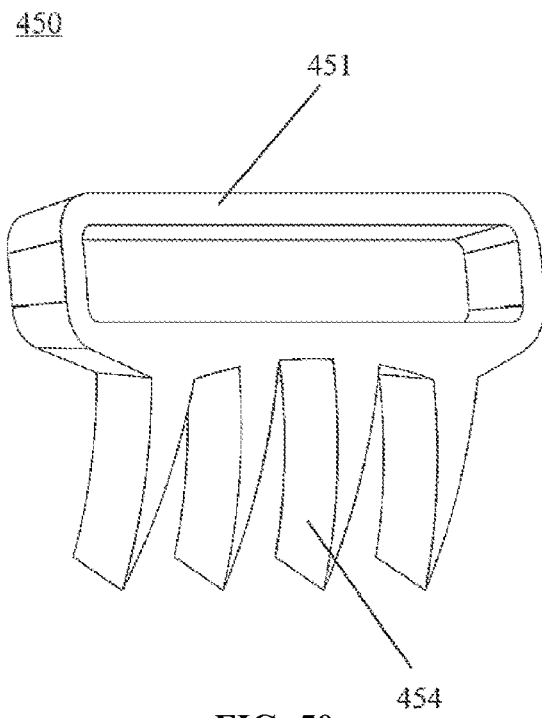
FIG. 50 is a structural schematic diagram illustrating agnails of an agnail clip according to some embodiments of the present disclosure.
Figure 52:
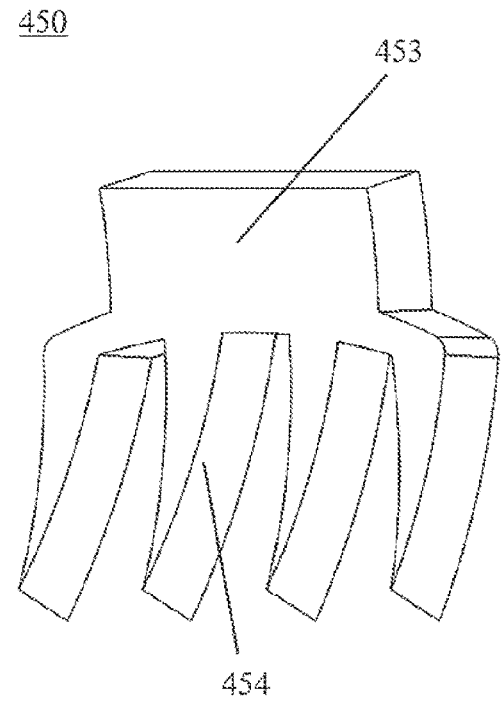
FIG. 52 is a structural schematic diagram illustrating agnails of an agnail clip according to some embodiments of the present disclosure.

FIG. 50 is a structural schematic diagram illustrating agnails of an agnail clip according to some embodiments of the present disclosure. FIG. 52 is a structural schematic diagram illustrating agnails of another agnail clip according to some embodiments of the present disclosure. As shown in FIG. 50 and FIG. 52, an agnail 450 may include a mounting unit which may be connected to the clipping unit 440. The agnail bars 454 may be disposed on the mounting unit. A shape of the agnail 450 may include a curved shape. The agnail 450 with the curved shape may be integrally formed, thereby facilitating the manufacture of the agnail 450, reducing the press concentration at a connection of the mounting unit and the agnail bars 454, and avoiding the breakage of the connection of the mounting unit and the agnail bars 454. In some embodiments, a shape of the mounting agnail 450 may be various. For example, the shape of the mounting unit may not be a curved shape, and a shape of the agnail bars 454 may be the curved shape. As another example, the shape of the mounting unit may include a cube, a rectangle, an annulus, etc.

In some embodiments, the mounting unit may be connected to the clipping unit 440 via a detachable connection, thereby facilitating detaching and/or replacing the agnail 450. The agnail clip 400 may be used to clip various tissues, and a position of the agnail 450 may be adjusted and/or changed for different patients. In some embodiments, the fixing unit 430, the clipping unit 440, and the agnail 450 may be integrally formed. Specifically, the fixing unit 430, the clipping unit 440, and the agnail 450 may be integrally formed by cutting a plate or a tube, for example, using a laser. The integrally formed fixing unit 430, the clipping unit 440, and the agnail 450 may improve the stability of the agnail clip 400, the reliability of connection(s) between components of the agnail clip 400, and facilitate the manufacture of the agnail clip 400.

In some embodiments, the agnail clip 400 may include at least two agnails 450, thereby improving the clipping force of the agnail clip 400 and prevent the clipped tissues from falling off when the agnail clip 400 clips the tissues. The at least two agnails 450 may be disposed at different positions of the clipping unit 440. For example, the at least two agnails 450 may be disposed on a first end, a second end, or a middle portion of the clipping unit 440. Those skilled in the art may determine a count of the agnail 450 according to characteristics of the tissues clipped by the agnail clip 400. For example, for tissues which may be relatively difficult to be clipped, the count of the agnail 450 may be increased. Alternatively, those skilled in the art may determine the position of the agnail 450 according to a position of the agnail clip 400 relative to the clipped tissues.

Figure 51:
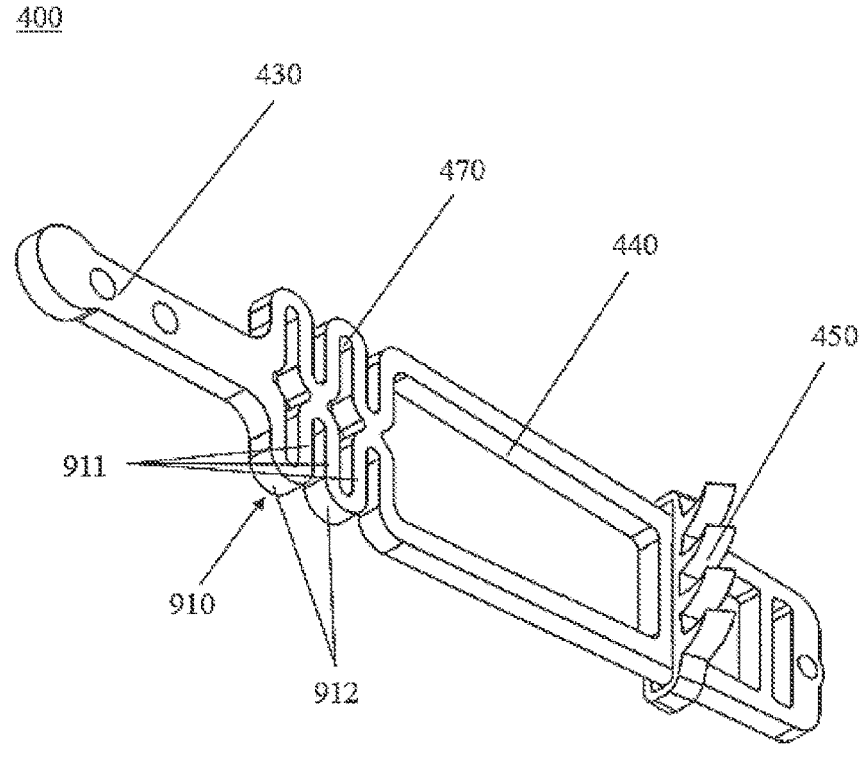
FIG. 51 is a structural schematic diagram illustrating agnails of an agnail clip according to some embodiments of the present disclosure.

In some embodiments, when the mounting unit is connected to the clipping unit 440 via a detachable connection, the mounting unit may include a snap ring 451. FIG. 51 is a structural schematic diagram illustrating agnails of the agnail clip shown in FIG. 50. As shown in FIG. 51, the snap ring 451 may be sleeved and snapped on the clipping unit 440. In some embodiments, the snap ring 451 may be made of an elastic material or a super-elastic metal (e.g., a nickel-titanium alloy), which may facilitate the snap ring 451 to be sleeved on the clipping unit 440. In some embodiments, after the snap ring 451 is sleeved on the clipping unit 440, the snap ring 451 may be fixedly connected to the clipping unit 440 via a bonding connection, a welding connection, etc., to improve the stability of the connection of the agnail 450 and the clipping unit 440. In order to sleeve the snap ring 451 on the clipping unit 440, a width of the clipping unit 440 may be increased from a second end of the clipping unit 440 to a first end of the clipping unit 440. When the agnail clip 400 includes at least two agnails 450, a size of an inner ring of the snap ring 451 may be determined based on the position of the at least two snap rings 451, thereby improving the stability of the agnail 450 on the clipping unit 440. Merely by way of example, a size of an inner ring of the snap ring 451 of the agnail 450 disposed on the second end of the clipping unit 440 may be relatively small, and a size of an inner ring of the snap ring 451 of the agnail 450 disposed on the first end of the clipping unit 440 may be relatively large.

Figure 53:
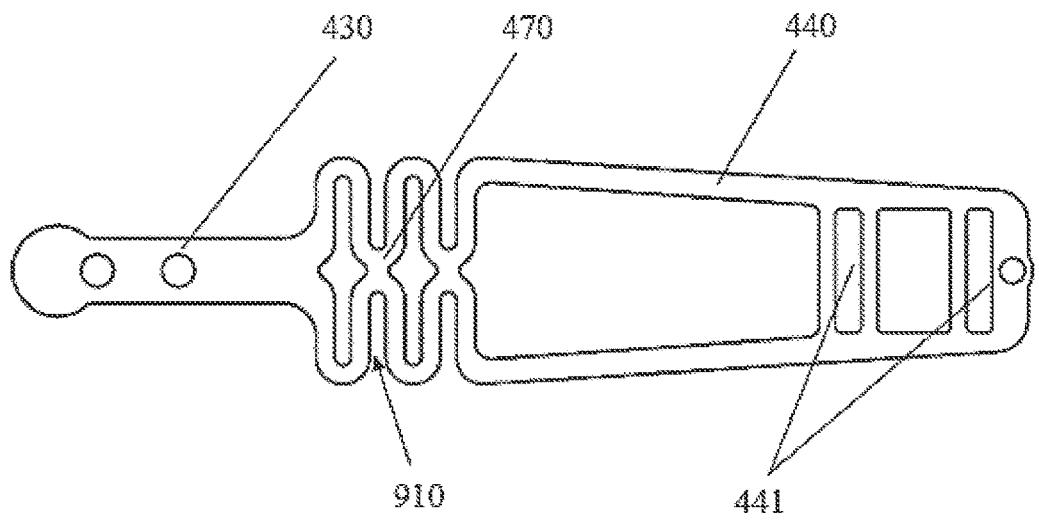
FIG. 53 is a structural schematic diagram illustrating a fixing unit, a bending unit, and a clipping unit of an agnail clip according to some embodiments of the present disclosure.

FIG. 53 is a structural schematic diagram illustrating a fixing unit, a bending unit, and a clipping unit of an agnail clip according to some embodiments of the present disclosure. When a mounting unit is connected to the clipping unit 440 via a detachable connection, the clipping unit 440 may include a slot 441 as shown in FIG. 53. As shown in FIGS. 47-49 and FIGS. 52-53, the mounting unit may include a fixing piece 453 which may be snapped in the slot 441. In some embodiments, after the fixing piece 453 is snapped in the slot 441, the fixing piece 453 may be fixed in the slot 441 via a bonding connection, a welding connection, etc., thereby improving the stability of the connection of the agnail 450 and the clipping unit 440. When the agnail clip 400 includes at least two agnails 450, a count of the slot 441 may be determined based on the count of the at least two agnails 450. Those skilled in the art may determine a position of the slot 441 based on the position of the agnails 450.

In some embodiments, the agnail 450 may be formed by cutting a shape-memory alloy (e.g., using a laser) and performing a heating and shaping operation on the shape-memory alloy. For example, the agnail 450 may be formed by cutting a shape-memory alloy pipe via a laser cutting, a water cutting, etc. The shape-memory alloy may include a nickel-titanium alloy, a cobalt-chromium alloy, or the like, or any combination thereof. In some embodiments, the fixing unit 430, the bending unit 470, and the clipping unit 440 may be integrally formed by cutting and/or performing a heating and shaping operation on a shape-memory alloy. In some embodiments, the bending unit 470 may include an S rod. More descriptions regarding the S rod may be found elsewhere in the present disclosure.

One or more beneficial effects may be realized according to the agnail clip described in the present disclosure. (1) The agnail clip may include an agnail with a curved shape, which may facilitate clipping tissues, and prevent the tissues falling off from between the agnail clip and an interior clamping arm, thereby improving the clamping stability of a tissue clamping device; (2) The agnail clip may have a relatively simple structure, which may be easily produced; (3) Agnail(s) of the agnail clip may be relatively easily detached and replaced. The agnail clip may be used to clip various tissues, and a position of the agnail(s) may be adjusted and/or determined for different patients; (4) A bending unit of the agnail clip may be deformed when the bending unit is performed a heating operation, thereby avoiding that the agnail clip is broken when the bending unit is bent. It should be noted that different embodiments may have different beneficial effects. In different embodiments, the beneficial effects may include any of the beneficial effects mentioned above or any other beneficial effects that may be realized.

In some embodiments, the tissue clamping device may include the agnail bars 454 with a curved shape and the clip 400 as described according to some embodiments of the present disclosure, thereby improving the clipping efficiency and stability of the tissue clamping device.

In some embodiments, the tissue clamping device may include interior clamping arms, and the fixing unit 430 of the agnail clip 400 may be connected to the interior clamping arms. When the interior clamping arms clip the tissues, the agnail 450 of the agnail clip 400 may hook the tissue. The agnail clip 400 with the curved agnail 450 may clip the tissues (e.g., the leaflet of the mitral valve, the vascular valve, etc.) to prevent the tissues from falling off between the agnail clip 400 and the interior clamping arms, thereby improving the clipping stability of the tissue clamping device. The agnail clip 400 and/or the tissue clamping device with the agnail clip 400 may be used for various occasions, for example, clipping tissues such as a heart valve (e.g., the mitral valve, the tricuspid valve, etc.), the vascular valve, etc., reaching at a predetermined position via various paths, which is not limited herein. In some embodiments, as shown in FIG. 16, an interior clamping arm (e.g., the first interior clamping arm 120, the second interior clamping arm 130, etc.) may include a through-hole 125 matched with the agnail 450. In some embodiments, a count of the through-hole 125 may be equal to a count of the agnail bar(s), for example, the count of the through-hole 125 and the count of the agnail bar(s) may be four. In some embodiments, the count of through-hole 125 may not be equal to the count of the agnail bar(s). For example, the through-hole may include a hole extending along a width direction of an interior clamping arm. The hole may accommodate all of the agnail bars. By disposing the through-hole 125 on the interior clamping arm, when an agnail clip is folded, the agnail 450 may be inserted into the through-hole 125 of the interior clamping arm, thereby improving clamping convenience, clamping efficiency, and stability of the agnail clip.

Figure 25:
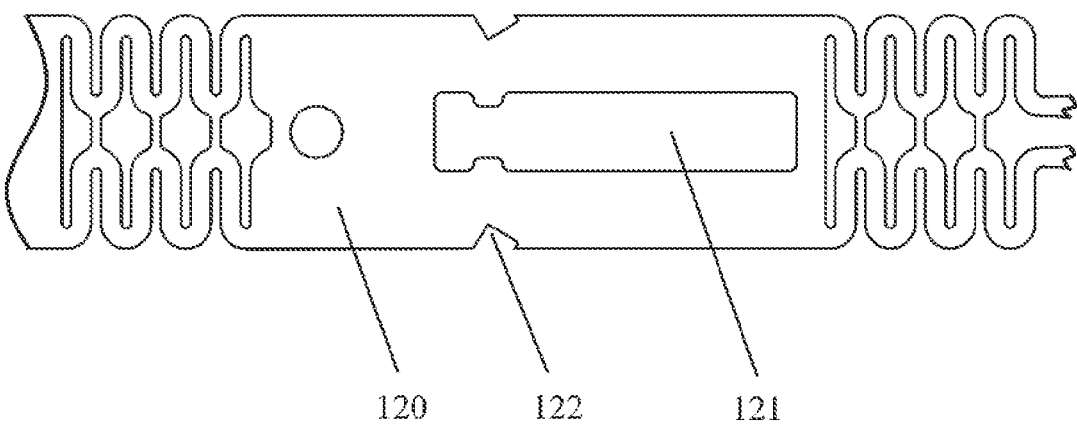
FIG. 25 is a structural schematic diagram illustrating an interior clamping arm of a tissue clamping device according to some embodiments of the present disclosure.
Figure 26:
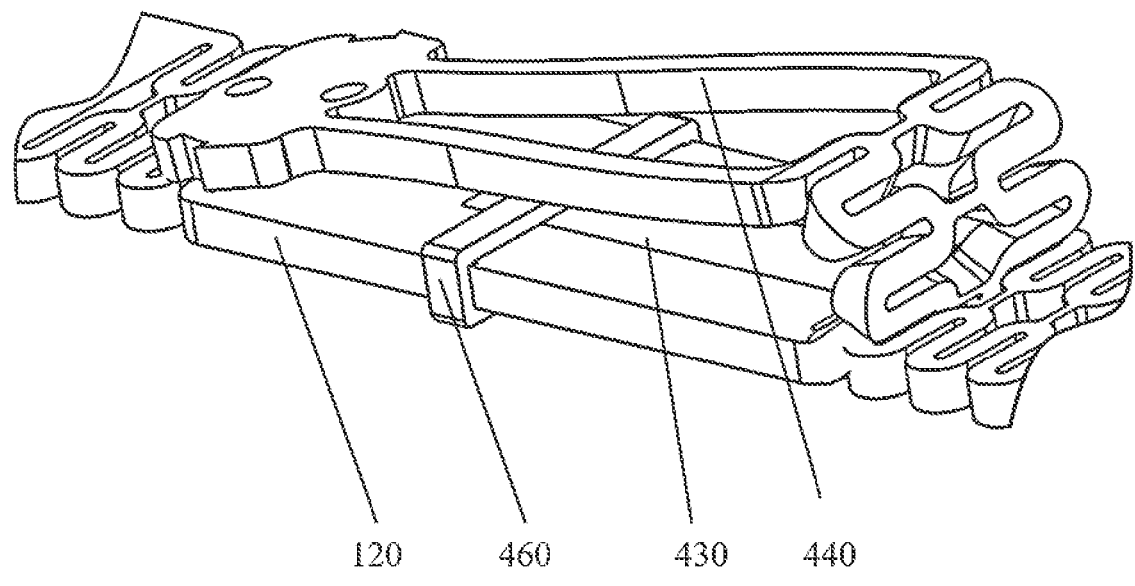
FIG. 26 is a schematic diagram illustrating a connection of an agnail clip, an interior clamping arm, and a fixing ring of a tissue clamping device according to some embodiments of the present disclosure.

FIG. 25 is a structural schematic diagram illustrating an interior clamping arm of a tissue clamping device according to some embodiments of the present disclosure. FIG. 26 is a schematic diagram illustrating a connection of an agnail clip, an interior clamping arm, and a fixing ring of a tissue clamping device according to some embodiments of the present disclosure. In some embodiments, as shown in FIG. 25 and FIG. 26, the interior clamping arm (e.g., the first interior clamping arm 120 or the second interior clamping arm 130, taking the first interior clamping arm 120 as an example) may include a snap hole 121 which may be matched a fixing unit 430 of the agnail clip. The fixing unit 430 may be embedded in the snap hole 121. Specifically, a shape of the snap hole 121 may be consistent with a shape of the fixing unit 430. In some embodiments, the first interior clamping arm 120 and the second interior clamping arm 130 may further include a fixing slot 122. The tissue clamping device may also include a fixing ring 460 connected to the fixing slot 122 to prevent the fixing unit 430 from disengaging from the snap hole 121. Specifically, the fixing slot 122 may be symmetrically disposed on both sides of the interior clamping arm in a width direction of the interior clamping arm as shown in FIG. 25. In an installation process, when the clamp 100 is integrally formed, the fixing ring 460 may be sleeved on the first interior clamping arm 120 and the second interior clamping arm 130 through the first exterior clamping arm 140 and the second exterior clamping arm 150, respectively. The fixing ring 460 may be made of an elastic material or a super-elastic alloy (e.g., nickel-titanium alloy). A cooperation of the snap hole 121 and the fixing unit 430 and a cooperation of the fixing slot 122 and the fixing ring 460 may improve installation convenience and stability of the agnail clip. In some alternative embodiments, after the fixing unit 430 is embedded in the snap hole 121, the fixing unit 430 may be directly fixed in the snap hole 121 via a bonding connection, a welding connection (e.g., a laser welding connection). For example, a gap between the fixing unit 430 and the snap hole 121 may be glued or welded. In some embodiments, the agnail clip may be connected to the interior clamping arm via a bonding connection, a welding connection, a riveting connection, a screwing connection, a snapping connection, or the like, or any combination thereof.

Figure 27:
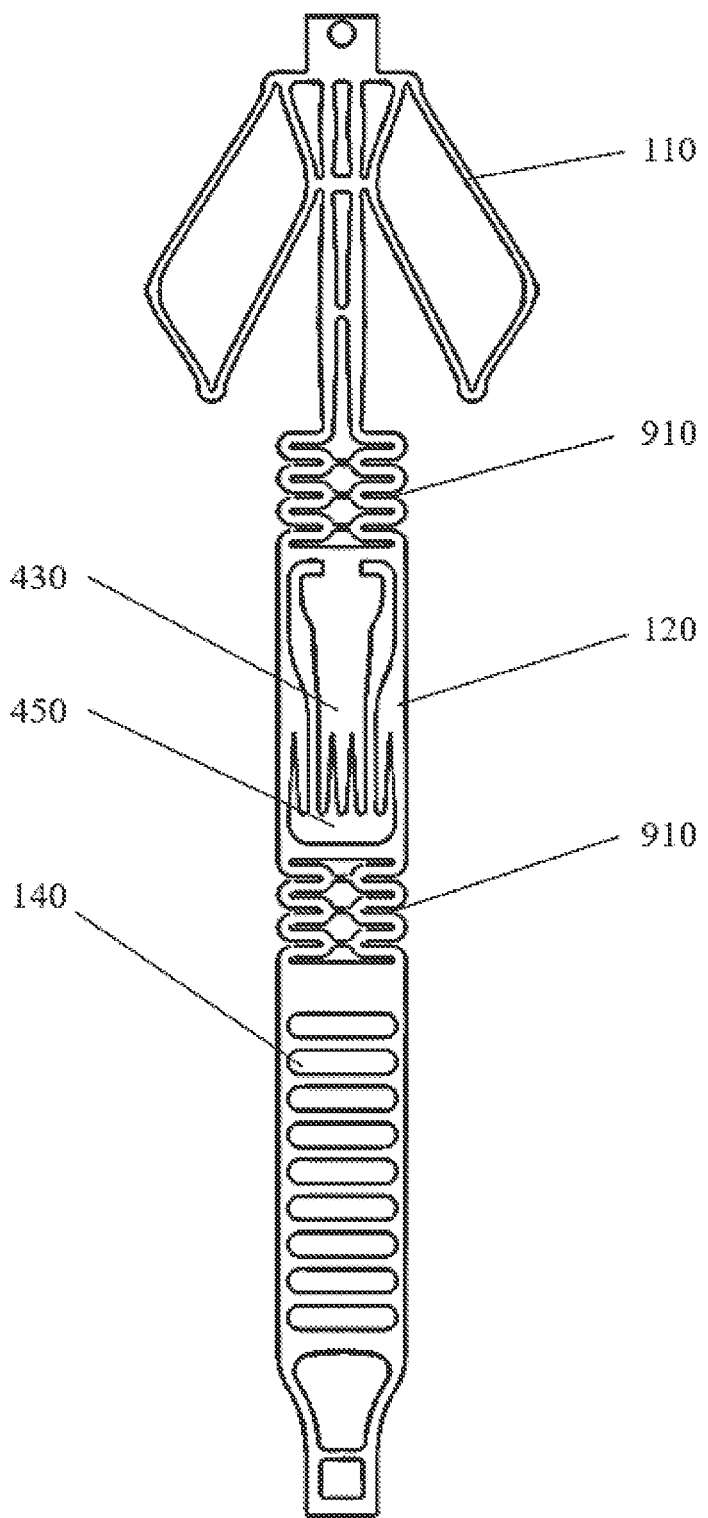
FIG. 27 is a structural schematic diagram illustrating an integrally formed agnail clip and a clamp of a tissue clamping device according to some embodiments of the present disclosure.

In some embodiments, the fixing unit 430 and the clipping unit 440 of the agnail clip may be integrally formed with the clamp 100. FIG. 27 is a structural schematic diagram illustrating an integrally formed agnail clip and a clamp of a tissue clamping device according to some embodiments of the present disclosure. As shown in FIG. 27, the fixing unit 430, the clipping unit 440, and the agnail 450 of the agnail clip may be integrally formed with the clamp 100. Specifically, when the clamp 100 is cut, shapes of the clamp 440 and the agnail 450 of the agnail clip may be cut on an interior clamping arm (e.g., the first interior clamping arm 120, the second interior clamping arm 130, etc.) of the clamp 100, and a first end of the cut clipping unit 440 may be connected to the interior clamping arm. In this case, an end of the agnail clip 430 may be connected to the interior clamping arm. In some embodiments, after the clipping unit 440 and the agnail 450 are cut integrally, the agnail 450 may be bent by being performed a heating operation. In some alternative embodiments, the clipping unit 440 may be cut on the interior clamping arm, and an agnail bar may be disposed on a second end of the cut clipping unit 440. The integral formation of all or a portion of the agnail clip and the interior clamping arm may improve the reliability of a connection of the agnail clip and the interior clamping arm, improve clamping stability of the tissue clamping device, simplify an assembly of the tissue clamping device, and improve the production efficiency of the tissue clamping device.

Figure 28:
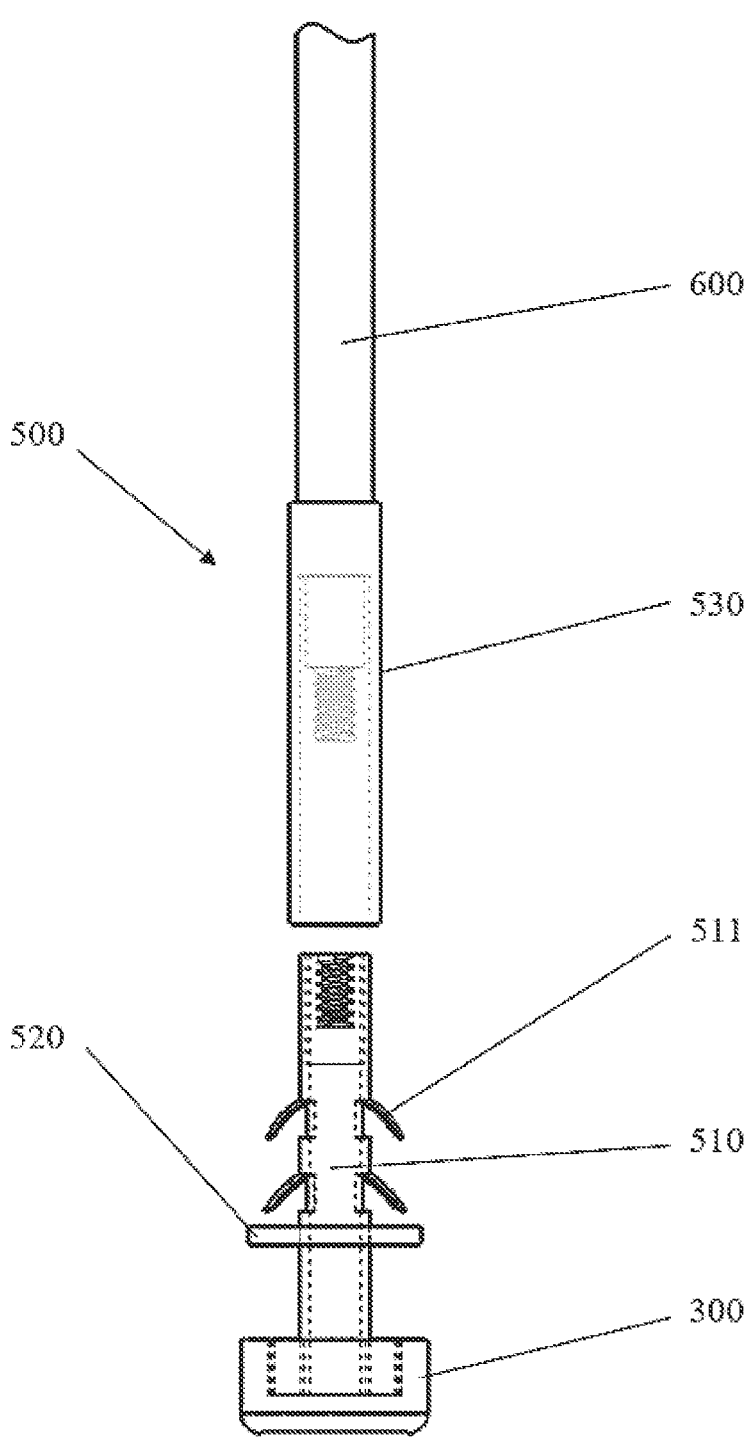
FIG. 28 is a structural schematic diagram illustrating a locking mechanism of a tissue clamping device according to some embodiments of the present disclosure.
Figure 29:
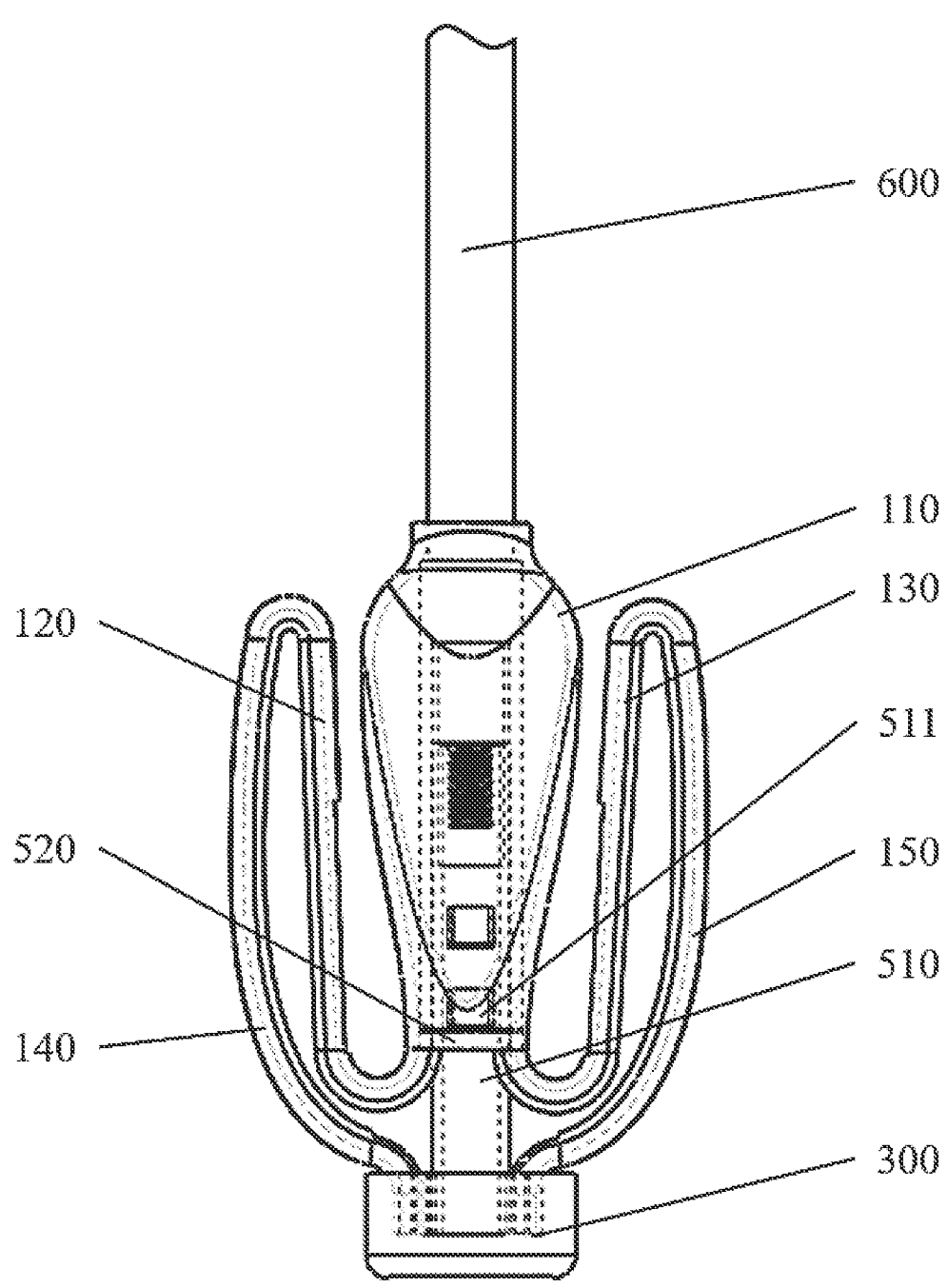
FIG. 29 is a structural schematic diagram illustrating a tissue clamping device including a locking mechanism according to some embodiments of the present disclosure.
Figure 30:
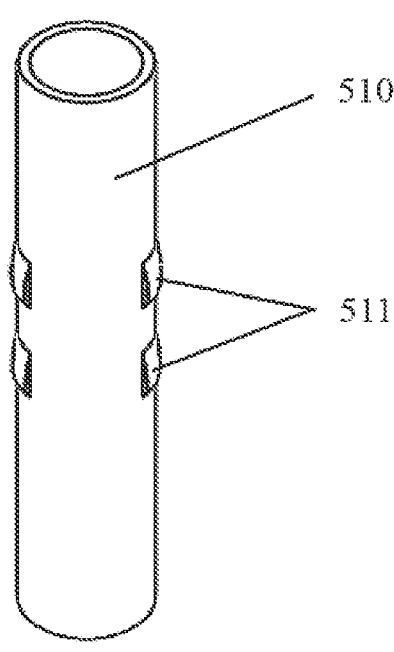
FIG. 30 is a structural schematic diagram illustrating a locking tube with folded locking tabs of a locking mechanism of a tissue clamping device according to some embodiments of the present disclosure.
Figure 31:
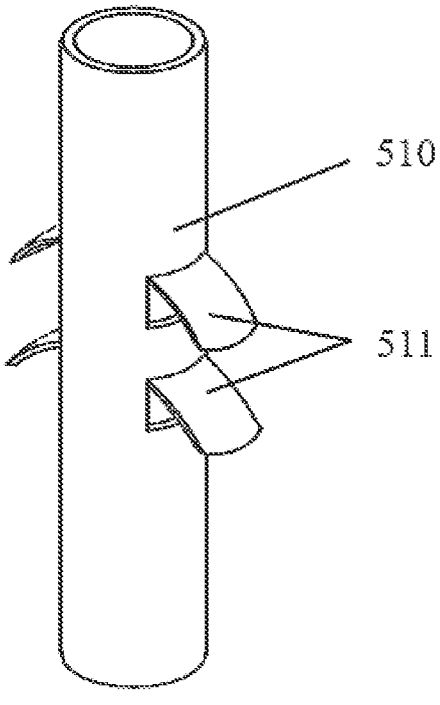
FIG. 31 is a structural schematic diagram illustrating a locking tube with expanded locking tabs of a locking mechanism of a tissue clamping device according to some embodiments of the present disclosure.

In some embodiments, the tissue clamping device may include a locking mechanism 500. FIG. 28 is a structural schematic diagram illustrating a locking mechanism of a tissue clamping device according to some embodiments of the present disclosure. FIG. 29 is a structural schematic diagram illustrating a tissue clamping device including a locking mechanism according to some embodiments of the present disclosure. As shown in FIG. 28 and FIG. 29, the locking mechanism 500 may include a locking tube 510 and a locking piece 520. One end (a lower end shown in FIG. 28 and FIG. 29) of the locking tube 510 may be fixedly connected to a second connector 300. An exterior wall of the locking tube 510 may be provided with a locking tab 511, and the locking tab 511 may be configured to restrict a clamp from being expanded. FIG. 30 is a structural schematic diagram illustrating a locking tub with folded locking tabs of a locking mechanism of a tissue clamping device according to some embodiments of the present disclosure. FIG. 31 is a structural schematic diagram illustrating a locking tube with expanded locking tabs of a locking mechanism of a tissue clamping device according to some embodiments of the present disclosure. As shown in FIG. 30 and FIG. 31, the locking tab 511 may be switched between a folded state and an expanded state. When the locking tab 511 is in the expanded state, an opening of the locking tab 511 may face the second connector 300. When there is no external pressure, the locking tab 511 may be in the expanded state by default. In some embodiments, the locking piece 520 may be fixedly connected to a supporting unit 110 of a clamp. For example, the locking piece 520 may be fixed in an interior cavity of the supporting unit 110 via a gluing connection, a welding (e.g., a laser welding) connection, or the like, or any combination thereof. The locking tab 511 may restrict the clamp from being expanded, that is, the first interior clamping arm 120 and the second interior clamping arm 130 may be relatively expanded, by restricting a movement of the locking piece 520. As shown in FIG. 28, when the locking piece 520 moves away from the second connector 300, the expanded locking tab 511 may resist the locking piece 520 to restrict the movement of the locking piece 520. In some alternative embodiments, the locking tab 511 may directly restrict an expansion of a clamp by restricting a movement of a part (e.g., the supporting unit 110) of the clamp. For example, the locking tab 511 in the expanded state may be directly resisted on the supporting unit 110.

In some embodiments, the locking mechanism 500 may cooperate with a first control mechanism which may be configured to control the first interior clamping arm 120 and the second interior clamping arm 130 to be expanded or folded, thereby restricting a relative expansion between the first interior clamping arm 120 and the second interior clamping arm 130. Specifically, a second end (e.g., an upper end as shown in FIG. 28) of the locking tube 510 may be detachably connected to a brake lever 600, and the brake lever 600 may control a movement of a second connector 300 relative to the first connector 200 through the locking tube 510. The locking tab 511 may restrict a relative movement of the locking piece 520 (or the supporting unit 110) and the locking tube 510 (or the second connector 300), thereby restricting the first interior clamping arm 120 and the second interior clamping arm 130 from being expanded relatively. The locking mechanism 500 may improve the clamping stability of the tissue clamping device after the tissue clamping device clamping the tissues, thereby effectively preventing the tissue clamping device from being expanded when the tissue clamping device is impacted by a blood flow. It should be understood that the locking tab 511 may be configured to restrict the relative expansion of the first interior clamping arm 120 and the second interior clamping arm 130, whereas the locking tab 511 may not restrict the folding of the first interior clamping arm 120 and the second interior clamping arm 130.

Figure 32:
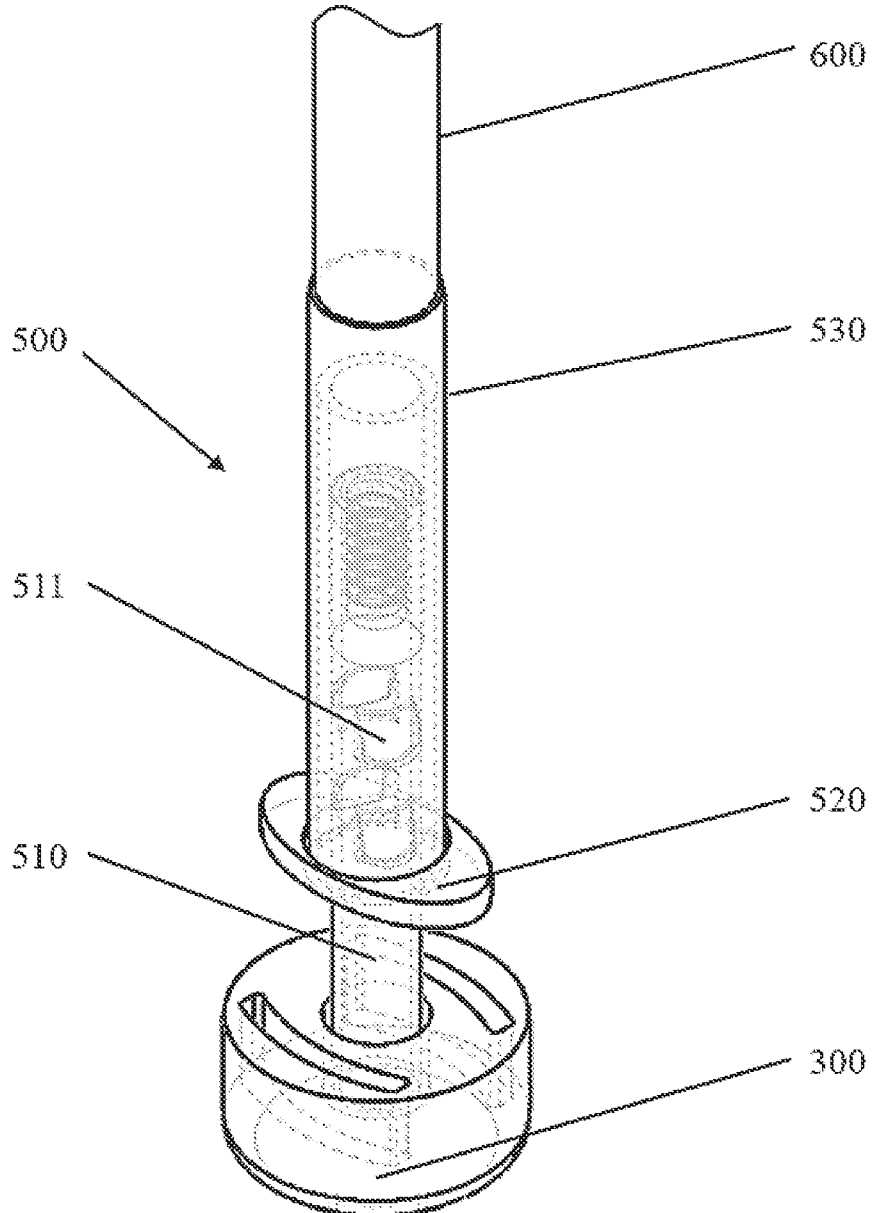
FIG. 32 is a structural schematic diagram illustrating an unlocked locking mechanism of a tissue clamping device according to some embodiments of the present disclosure.
Figure 33:
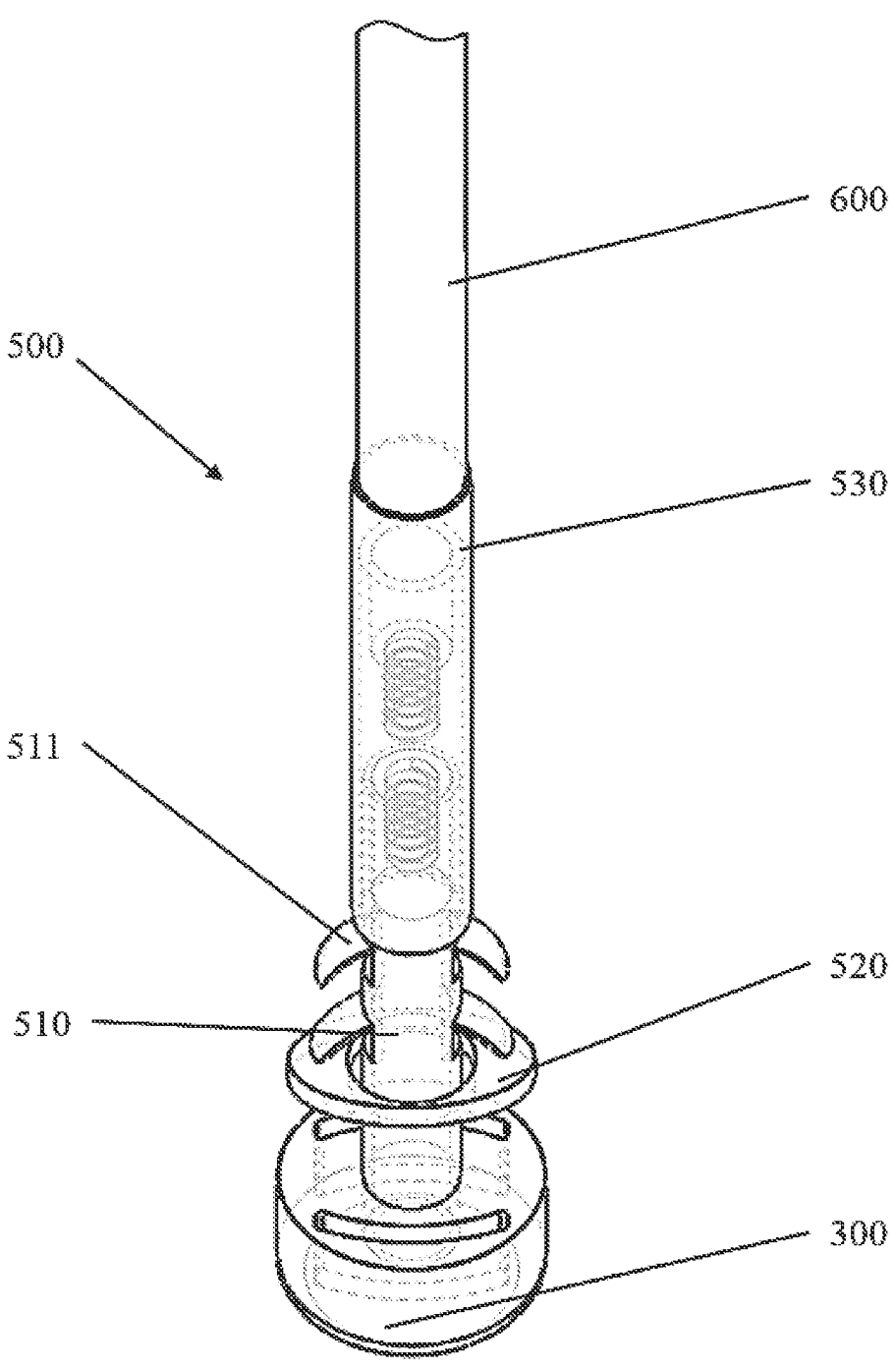
FIG. 33 is a structural schematic diagram illustrating a locked locking mechanism of a tissue clamping device according to some embodiments of the present disclosure.

In some embodiments, the locking mechanism 500 may further include a sleeve 530 which may be configured to be sleeved outside the locking tube 510 and retract the locking tab 511. Specifically, when the locking tab 511 is within the sleeve 530, the locking tab 511 may be forced to retract, and when the locking tab 511 is exposed outside the sleeve 530, the locking tab 511 may be automatically expanded. In some embodiments, a brake lever 600 of a tissue clamping device may be fixedly connected to the sleeve 530 e.g., via a welding connection, a bonding connection, a threading connection, etc. The brake lever 600 may be detachably connected to the locking tube 510, for example, via a threading connection. When the brake lever 600 is connected to the locking tube 510, the sleeve 530 may retract the locking tab 511. When the brake lever 600 is disengaged from the locking tube 510, the sleeve 530 may release the locking tab 511, and the locking tab 511 may be expanded. As shown in FIG. 32 and FIG. 33, FIG. 32 illustrates that a locking mechanism 500 is not locked and the locking tab 511 is folded. FIG. 33 illustrates that the locking mechanism 500 is locked and the locking tab 511 is expanded. In some embodiments, a diameter of an interior hole of the locking piece 520 may be larger than an exterior diameter of the sleeve 530, and the expanded locking tab 511 may not pass the interior hole of the locking piece 520. When the brake lever 600 is connected to the locking tube 510, the sleeve 530 may hold the locking tube 511 disposed on the locking tab 510. The locking piece 520 may slide freely on the locking tube 510 and the sleeve 530, and a tissue clamping device may clamp the tissues. After the tissue clamping device clamps the tissues, the brake lever 600 and the sleeve 530 may be removed. In this case, the sleeve 530 may release an effect on the locking tab 511, and the locking tab 511 disposed in the sleeve 511 may be exposed outside the sleeve 530 and may be expanded. The locking tab 511 may restrict a movement of the locking piece 520 to restrict the clamp from being expanded.

In some embodiments, the brake lever 600 may be connected to the locking tube 510 via a threading connection. For example, an end of the brake lever 600 connected to the locking tube 510 may be provided with external threads, and the locking tube 510 may be provided with internal threads corresponding to the external threads. The sleeve 530 may be sleeved outside the brake lever 600 and cover the external thread of the brake lever 600, such that the brake lever 600 and the locking tube 510 may be easily disengaged. In some embodiments, the brake lever 600 may be connected to the locking tube 510 via a detachable connection (e.g., a snapping connection).

In some embodiments, the locking tabs 511 may include at least two tabs disposed on two locations of an exterior wall of the locking tab 510, and a distance between one of the two locations and the second connector 300 and a distance between the other of the two locations and the second connector 300 may be the same (or substantially the same). It should be noted that a count of locking tabs 511 may include 2, 3, 4, etc. Two or four locking tabs 511 may be disposed on the exterior wall of the locking tube 510 in an axially symmetrical (or centrally symmetrical) manner. Three locking tabs 511 may be disposed on an exterior wall of the locking tube 510 in a centrally symmetrical manner, for example, an angle between each two adjacent locking tabs may be 120 degrees. The at least two locking tabs 511 which may be disposed symmetrically and configured to restrict a movement of the locking piece 520, thereby evenly dispersing a stress on the locking piece 520, improving the stability of the locking mechanism 500, and improving a service life of the locking mechanism 500.

In some embodiments, the locking tabs 511 may include at least two tabs symmetrically disposed on two locations of the exterior wall of the locking tab 510, and a distance between one of the two locations and the second connector and a distance between the other of the two locations and the second connector are different. The at least two locking tabs 511 may be configured to restrict the clamp 100 from being expanded when the clamp expands and/or folds to different angles (e.g., the first interior clamping arm 120 and the second interior clamping arm 130 may be expanded to different angles, relatively). It should be understood that when the first interior clamping arm 120 and the second interior clamping arm 130 are expanded to different angles, relatively, distances between the locking piece 520 and the second connector 300 may be different, and the locking tabs 511 may be configured to abut against the locking piece 520 to restrict the locking piece 520 (e.g., the supporting unit 110) from moving relative to the supporting unit 300. In an actual operation, due to different pathological conditions and physiological structures of different patients or clamped tissues, the expanding and folding angles of the clamp 100 when a tissue clamping device clamps and folds a tissue may be different. The tissue clamping device with the locking mechanism 500 may be applied for different patients or tissues.

In some embodiments, the locking tube 510 and the locking tab 511 may be integrally formed. For example, the locking tube 510 with the locking tab 511 may be cut from a tube, e.g., using a laser. In some embodiments, the locking tube 510 and the locking tab 511 may be integrally formed by cutting and performing a heat treating and shaping operation on a shape-memory alloy. The shape-memory alloy may include a nickel-titanium alloy, a cobalt-chromium alloy, or the like, or any combination thereof. After the locking tube 510 with locking tab 511 is cut from the shape-memory alloy, a connection of the locking tab 511 and the locking tube 510 may be performed the heating and shaping operation to expend the locking tab 511 outward. After being performed the heating and shaping operation, the connection of the locking tab 511 and the locking tube 510 may have prefabricated resilience force which may cause the locking tab 511 to be automatically expanded when the locking tab 511 exposes outside the sleeve 530. In some alternative embodiments, the locking tube 510 and the locking tab 511 may be different parts and connected to each other. For example, the locking tab 511 may include an elastic sheet, which may be fixedly connected to the locking tube 510 via a bonding connection, a welding (e.g., laser welding) connection, or the like, or any combination thereof.

In some embodiments, a tissue clamping device may include an elastic bracket 700. FIGS. 34-37 are structural schematic diagrams illustrating an elastic bracket of a tissue clamping device according to some embodiments of the present disclosure. As shown in FIGS. 34-37, the elastic bracket 700 may include a first supporting rod 710, a second supporting rod 720, a first mounting unit 730, and a second mounting unit 740. A first end of the first supporting rod 710 and a first end of the second supporting rod 720 may be connected to the first mounting unit 730. A second end of the first supporting rod 710 and a second end of the second supporting rod 720 may be connected to the second mounting unit 740. In some embodiments, the elastic bracket 700 may be integrally formed. That is, the first supporting rod 710, the second supporting rod 720, the first mounting unit 730, and the second mounting unit 740 may be integrally formed, thereby improving the stability, the reliability of connections between components of the elastic bracket 700 and reduce the cost of production of the elastic bracket 700. The first mounting unit 730 and the second mounting unit 740 of the elastic bracket 700 may be fixedly connected to the second connector 300. That is, both ends of the first supporting rod 710 and the second supporting rod 720 may be fixed to the second connector 300. The first supporting rod 710 of the elastic bracket 700 may bear against a connection of the first interior clamping arm 120 and the first exterior clamping arm 140. The second supporting rod 720 of the elastic bracket 700 may bear against a connection of the second interior clamping arm 130 and the second exterior clamping arm 150. For example, as shown in FIG. 1, the first supporting rod 710 (not shown in FIG. 1) may be internally bear against between the first interior clamping arm 120 and the first exterior clamping arm 140, and the second supporting rod 720 (not shown in FIG. 1) may be internally bear against between the second interior clamping arm 130 and the second exterior clamping arm 150. In some embodiments, when the first supporting rod 710 or the second supporting rod 720 bears against between an interior clamping arm and an exterior clamping arm, the first supporting rod 710 or the second supporting rod 720 may be fixedly connected to a connection of the interior clamping arm and the exterior clamping arm, for example, via a bonding connection, a laser welding connection, a winding wire connection, or the like, or any combination thereof. In some alternative embodiments, the first supporting rod 710 may bear outside the first exterior clamping arm 140 and the second supporting rod 720 may bear outside the second exterior clamping arm 150. For example, a middle portion of the first supporting rod 710 may be fixedly connected to outside of the first exterior clamping arm (e.g., via a bonding connection, a laser welding connection, a winding wire connection, etc.), and the second supporting rod 720 may be fixedly connected to outside of the second exterior clamping arm 150. The elastic bracket 700 may increase an area of a tissue clamping device for clamping tissues, thereby improving the stability of the tissue clamping device. The elastic bracket 700 may improve a clamping performance of the tissue clamping device, and elastic force of the elastic bracket 700 may improve the clamping force of first interior clamping arm 120 and the second interior clamping arm 130 on the tissues when the first interior clamping arm 120 and the second interior clamping arm 130 are folded. In addition, the elastic force provided by the elastic bracket 700 may be adjusted according to different clamping requirements for different tissues or different patients (e.g., a width of the first supporting rod 710 and/or the second supporting rod 720 may be adjusted). The tissue clamping device with the elastic bracket 700 may be used for different tissues or patients.

Figure 34:
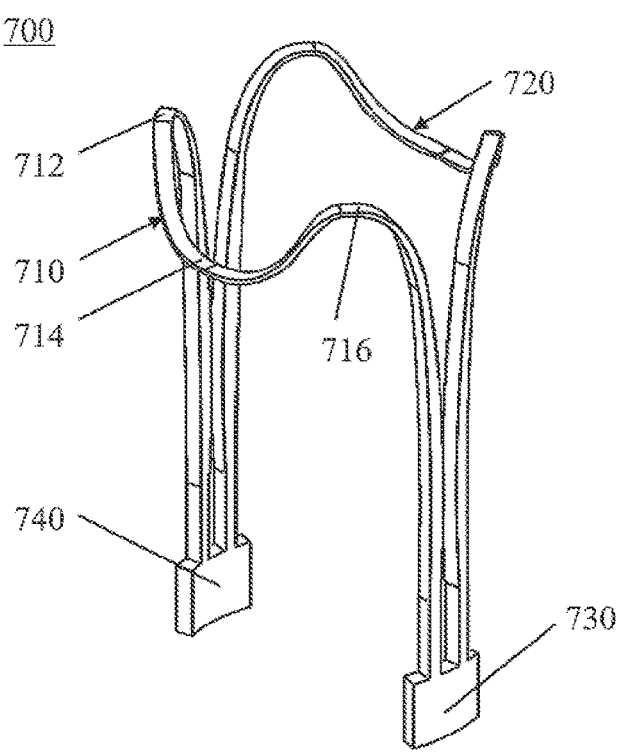
FIG. 34 is a structural schematic diagram illustrating an elastic bracket of a tissue clamping device according to some embodiments of the present disclosure.

As shown in FIG. 34, a middle portion of each of the first supporting rod 710 and the second supporting rod 720 may include a first arc segment 712, a second arc segment 714, and a third arc segment 716, which may be successively connected. A convex direction of the second arc segment 714 may be opposite to the convex directions of the first arc segment 712 and the third arc segment 716. The second arc segment 714 may be convex toward the second connector 300, and the first arc segment 712 and the third arc segment 716 may be convex toward a direction away from the second connector 300. When the elastic bracket 700 and the clamp 100 are assembled, the second arc segment 714 of the first supporting rod 710 and the second supporting rod 720 may be disposed between the first interior clamping arm 120 and the first exterior clamping arm 140, and between the second interior clamping arm 130 and the second exterior clamping arm 150, respectively. With the configuration mentioned above, the first supporting rod 710 and the second supporting rod 720 may surround the supporting unit 110 and cover tissues.

Figure 35:
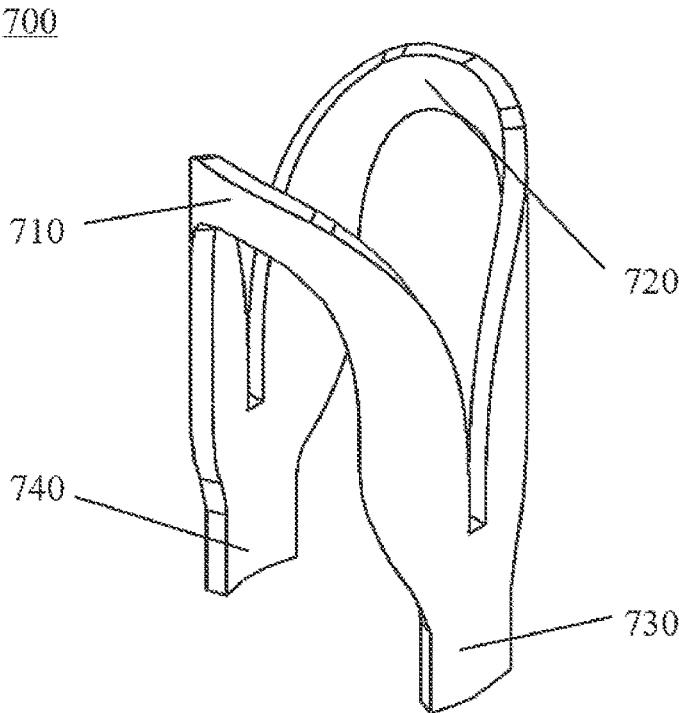
FIG. 35 is a structural schematic diagram illustrating an elastic bracket of a tissue clamping device according to some embodiments of the present disclosure.

In some embodiments, as shown in FIG. 35, each of the first supporting rod 710 and the second supporting rod 720 may have a certain width. For example, the width of each of the first supporting rod 710 and the second supporting rod 720 may be greater than a width threshold. The width threshold may be 2 times, 3 times, 4 times, etc., of a thickness of a supporting rod (e.g., the first supporting rod 710, the second supporting rod 720, etc.). In some embodiments, the width of each of the first supporting rod 710 and/or the second supporting rod 720 may be a positive correlation with elastic force for a tissue clamping device provided by the elastic bracket 700. It should be understood that within a certain range of the width, the wider the width of each of the first supporting rod 710 and the second supporting rod 720, the greater the elastic force for the tissue clamping device provided by the elastic bracket 700, accordingly the greater the clamping force of the tissue clamping device against tissues may be. In some embodiments, the width of the elastic bracket 700 may be determined according to the clamping requirements of different tissues or different patients. In some embodiments, a width of each segment of each of the first supporting rod 710 and the second supporting rod 720 may be different, thereby further adjusting the elastic force for the tissue clamping device provided by the elastic bracket 700.

Figure 36:
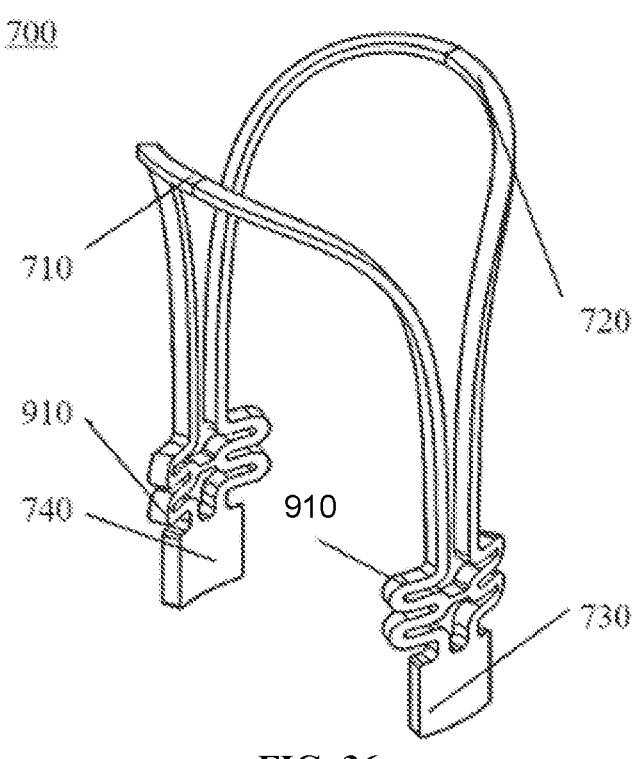
FIG. 36 is a structural schematic diagram illustrating an elastic bracket of a tissue clamping device according to some embodiments of the present disclosure.

In some embodiments, as shown in FIG. 36, each of a first end of the first supporting rod 710 and a first end of the second supporting rod 720 may be connected to the first mounting unit 730 via a curved rod of an S rod 910. Each of a second end of the first supporting rod 710 and a second end of the second pole 720 may be connected to the second mounting unit 740 via a curved rod of another S rod 910. Each of the S rods 910 may at least include three straight rods 911 and two curved rods 912. The three straight rods 911 may be parallel to each other, and arranged in sequence. Two ends of each two adjacent straight rods of the three straight rods 911 may be connected, and the two ends of each two adjacent straight rods of the three straight rods 911 may be located at a same side of the S rod 910. The two ends of each two adjacent straight rods of the three straight rods 911 may be connected via one of the two curved rods 912. More descriptions regarding the S rods 910 may be found elsewhere in the present disclosure. See, e.g., FIGS. 8-10 and the relevant descriptions thereof. The S rods 910 disposed at a mounting unit of the first supporting rod 710 and the second supporting rod 720 may improve a shape change performance of the elastic bracket 700 (e.g., the first end of the first supporting rod 710, the second supporting rod 720, etc.) when the elastic bracket 700 is performed a heating and shaping operation.

Figure 37:
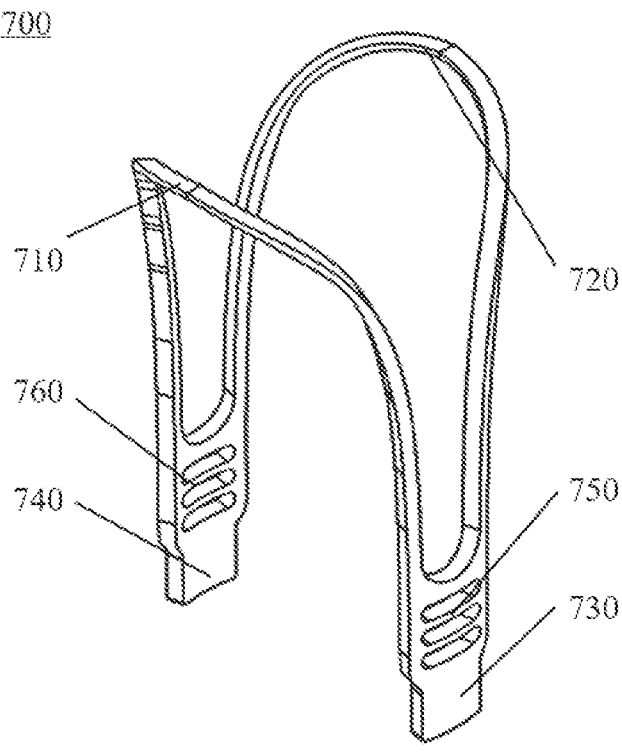
FIG. 37 is a structural schematic diagram illustrating an elastic bracket of a tissue clamping device according to some embodiments of the present disclosure.

In some embodiments, as shown in FIG. 37, the first end of the first supporting rod 710 and the first end of the second supporting rod 720 may be connected to the first mounting unit 730 via a first connecting unit 750. The second end of the first supporting rod 710 and the second end of the second supporting rod 720 may be connected to the second mounting unit 740 via a second connecting unit 760. The first connecting unit 750 and/or the second connecting unit 760 may include one or more through-holes. A count of the through-hole(s) may be determined based on actual conditions. A shape of the through-hole(s) may include but is not limited to a strip, a square, a circle, a rectangle, etc. The through-hole(s) disposed on the first connecting unit 750 and/or the second connecting unit 760 may improve the shape change performance of the elastic bracket 700 (e.g., the first end of the first supporting rod 710, the second supporting rod 720, etc.) when the elastic bracket 700 is performed the heating and shaping operation.

Figure 38:
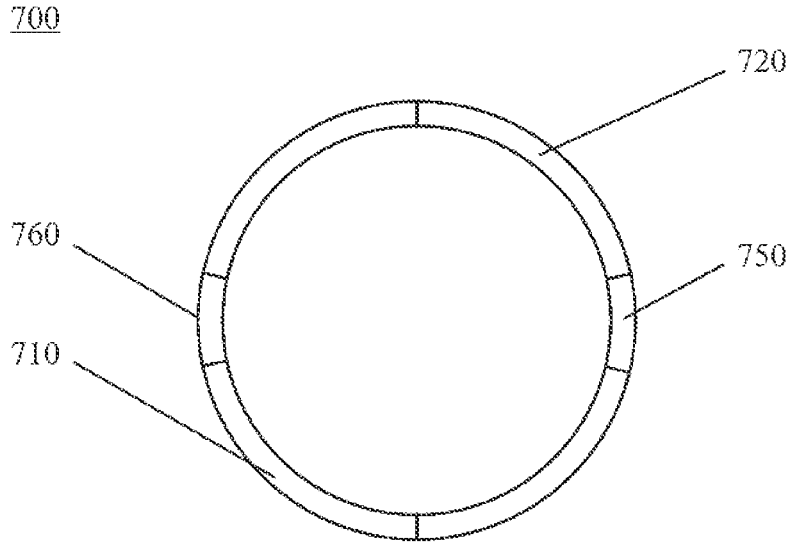
FIG. 38 is a schematic diagram illustrating a top view of the elastic bracket in FIG. 37 according to some embodiments of the present disclosure.
Figure 39:
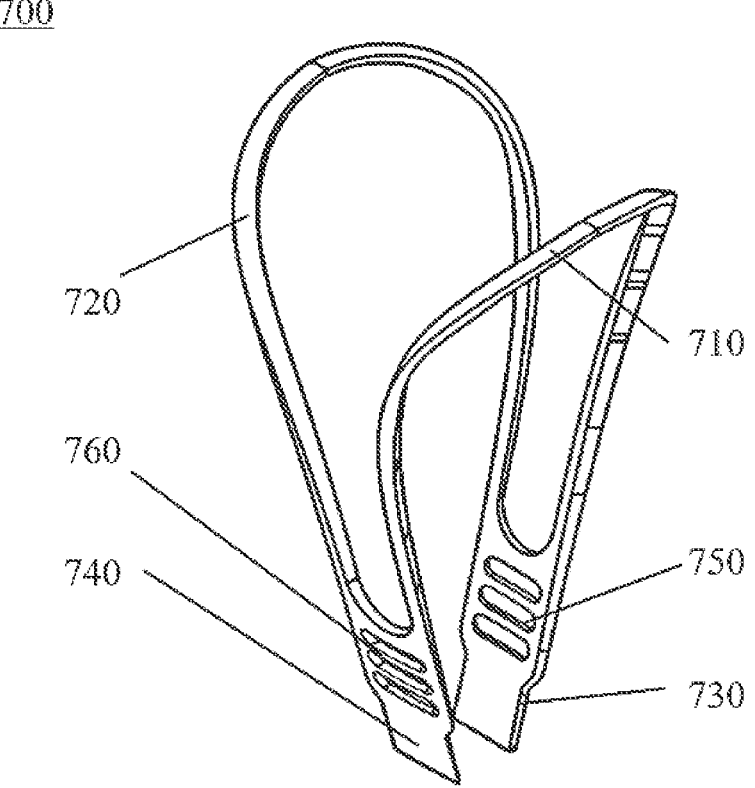
FIG. 39 is a structural schematic diagram illustrating the elastic bracket in FIG. 37 after being performed a heating operation according to some embodiments of the present disclosure.

In some embodiments, the elastic bracket 700 may be integrally formed by cutting and/or performing the heating and shaping operation on a shape-memory alloy. The shape-memory alloy may include a nickel-titanium alloy, a cobalt-chromium alloy, or the like, or any combination thereof. Preferably, a material of the elastic bracket 700 may include a super-elastic metal (e.g., a nickel-titanium alloy). FIG. 38 is a schematic diagram illustrating a top view of the elastic bracket 700 shown in FIG. 37 according to some embodiments of the present disclosure. As shown in FIG. 38, the elastic bracket 700 shown in FIG. 37 may be cut from the shape-memory alloy. Similarly, the elastic bracket 700 shown in FIGS. 34-36 may also be produced by cutting a shape-memory alloy. After the elastic bracket 700 is cut from the shape-memory alloy, the elastic bracket 700 may be further performed a heating operation. FIG. 39 is a structural schematic diagram illustrating the elastic bracket in FIG. 37 after being performed the heating operation according to some embodiments of the present disclosure. As shown in FIG. 39, after being performed the heating operation, the first mounting unit 730 and the second mounting unit 740 may be folded relative to each other, and the elastic bracket 700 may be disposed on the second connector 300. In addition, after being performed the heating operation, each of the first supporting rod 710 and the second supporting rod 720 may have prefabricated resilience force. After the elastic bracket 700 is disposed on the second connector 300 and assembled with the clamp 100, when the first interior clamping arm 120 and the second interior clamping arm 130 clamp tissues and are folded, the prefabricating resilience force of the first supporting rod 710 and the second supporting rod 720 may cause the first interior clamping arm 120 and the second interior clamping arm 130 to further clamp the tissues, thereby improving the stability of the tissue clamping device.

Figure 40:
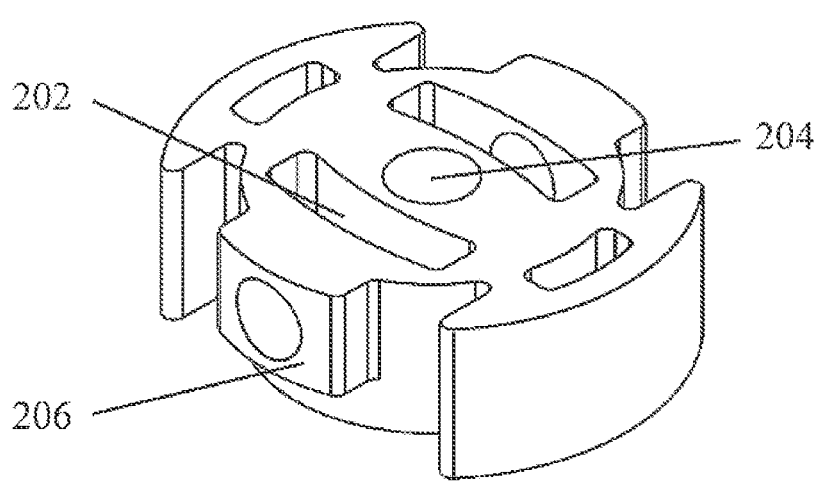
FIG. 40 is a structural schematic diagram illustrating a first connector of a tissue clamping device according to some embodiments of the present disclosure.
Figure 41:
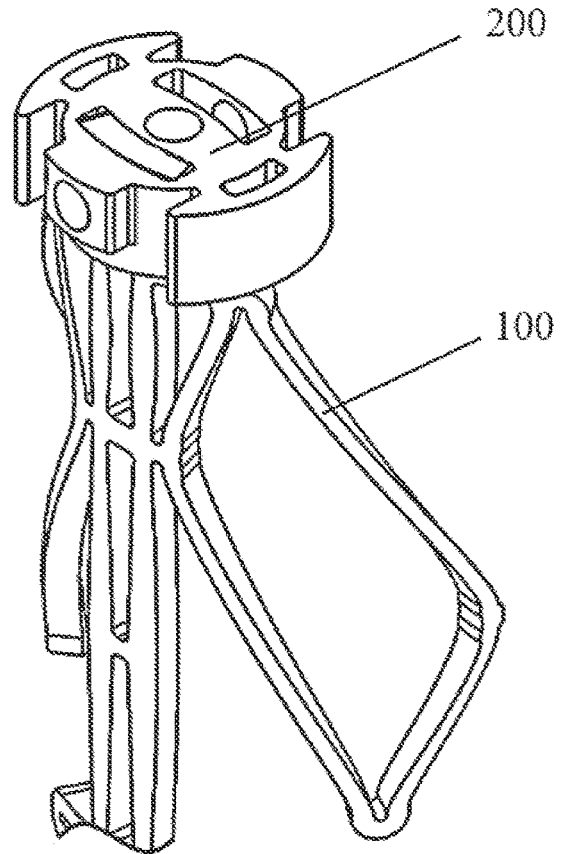
FIG. 41 is a schematic diagram illustrating a connection of a first connector and a clamp of a tissue clamping device according to some embodiments of the present disclosure.

FIG. 40 is a structural schematic diagram illustrating a first connector of a tissue clamping device according to some embodiments of the present disclosure. FIG. 41 is a schematic diagram illustrating a connection of a first connector and a clamp of a tissue clamping device according to some embodiments of the present disclosure. As shown in FIGS. 40-41, a first connector 200 may include a mounting bayonet 202, and one end of the clamp 110 (e.g., an upper end as shown in FIG. 41) of the supporting unit 100 may be inserted and fixed into the mounting bayonet 202. In addition, the first connector 200 may include a through-hole 204 through which a brake lever 600 may pass. A side wall of the first connector 200 may include a convex block 206 to which a conveying connector 800 may be connected. In some embodiments, after one end of the supporting unit 110 is inserted into the mounting bayonet 202, the supporting unit 110 may be fixedly connected to the first connector 200 via a pin. In some alternative embodiments, after the one end of the supporting unit 110 is inserted into the mounting bayonet 202, the supporting unit 110 may be fixedly connected to the first connector 200 via a bonding connection, a welding connection, or the like, or any combination thereof.

Figure 42:
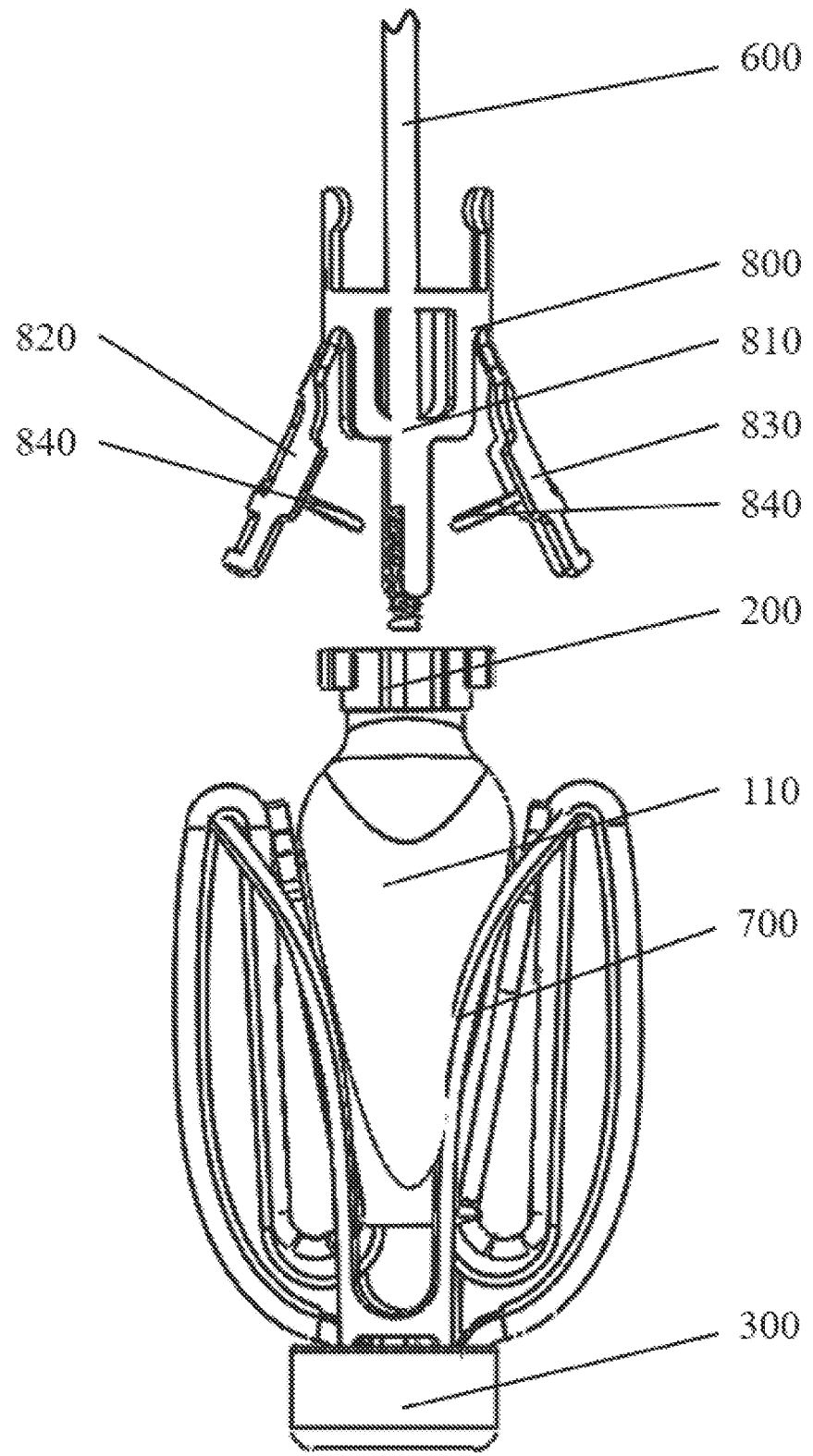
FIG. 42 is a schematic diagram illustrating a connection of a clamp and a conveying assembly of a tissue clamping device according to some embodiments of the present disclosure.

FIG. 42 is a schematic diagram illustrating a connection of a clamp and a conveying assembly of a tissue clamping device according to some embodiments of the present disclosure. As shown in FIG. 2 and FIG. 42, the first connector 200 may be connected to a conveying connector 800 of the conveying assembly to convey the tissue clamping device to a predetermined position by the conveying assembly. After a tissue clamping device clamps tissues, the conveying connector 800 of the conveying assembly may be disengaged from the tissue clamping device, the conveying assembly may be withdrawn, and the tissue clamping device may remain in a body of a patient.

As shown in FIG. 42, the conveying connector 800 may include a main body 810, a first connecting piece 820, and a second connecting piece 830. A connection of the first connecting piece 820 and the main body 810 and/or a connection of the second connecting piece 830 and the main body 810 may have prefabricated resilience force which may cause the first connecting piece 820 and the second connecting piece 830 to be automatically expanded in a natural state. A fixing supporting rod 840 may be disposed on a middle portion of the first connecting piece 820 and a middle portion of the second connecting piece 830. The fixing supporting rod 840 may be perpendicular to the first connecting pieces 820 and the second connecting piece 830. One end of the fixing supporting rod 840, which may be floated, may include a through-hole through which the brake lever 600 may pass. As shown in FIG. 2 and FIG. 42, when the conveying connector 800 is connected to the first connector 200 of the tissue clamping device, the first connecting piece 820 and the second connecting piece 830 may be relatively folded, and the first connecting piece 820 and the second connecting piece 830 may be connected to the convex block 206 of the first connector 200, respectively, e.g., via a snapping connection. In this case, the brake lever 600 may pass through the through-hole on the fixed supporting rod 840 connected to the first connecting piece 820 and the second connecting piece 830. The brake lever 600 may restrict the first connecting piece 820 and the second connecting piece 830 from being expanded. When the conveying assembly is disengaged from the tissue clamping device, the brake lever 600 may be disconnected with the tissue clamping device, the brake lever 600 may be pulled back, and the brake lever 600 may be disengaged from the through-hole on the fixing supporting rod 840, accordingly the first connecting piece 820 and the second connecting piece 830 may be automatically expanded and disengaged from the convex block 206. In some embodiments, the conveying connector 800 may be integrally formed by cutting and performing a heating and shaping operation on a shape-memory alloy. Specifically, during the heating operation, the first connecting piece 820 and the second connecting piece 830 of the conveying connector 800 may be bent relative to the main body 810, and the connection of the first connecting piece 820 and the main body 810 and/or the connection of the second connecting piece 830 and the main body 810 may have prefabricated resilience force. In addition, the fixing supporting rod 840 may be bent to be perpendicular to the first connecting piece 820 or the second connecting piece 830 during the heating operation.

Figure 43:
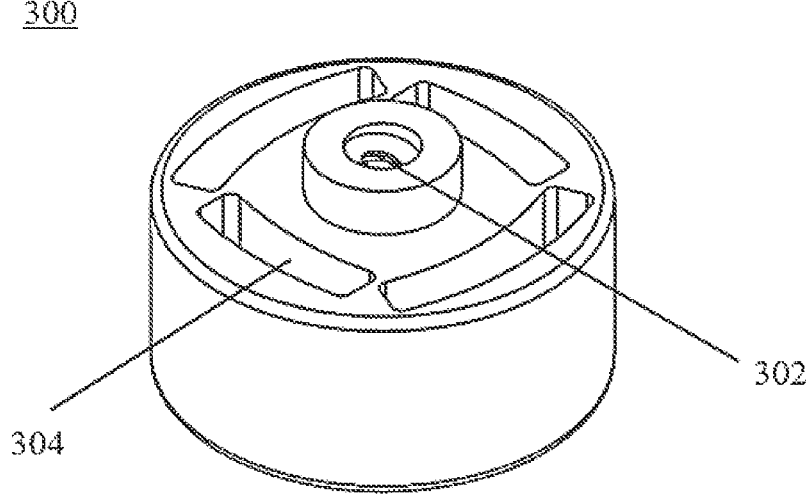
FIG. 43 is a structural schematic diagram illustrating a second connector of a tissue clamping device according to some embodiments of the present disclosure.
Figure 44:
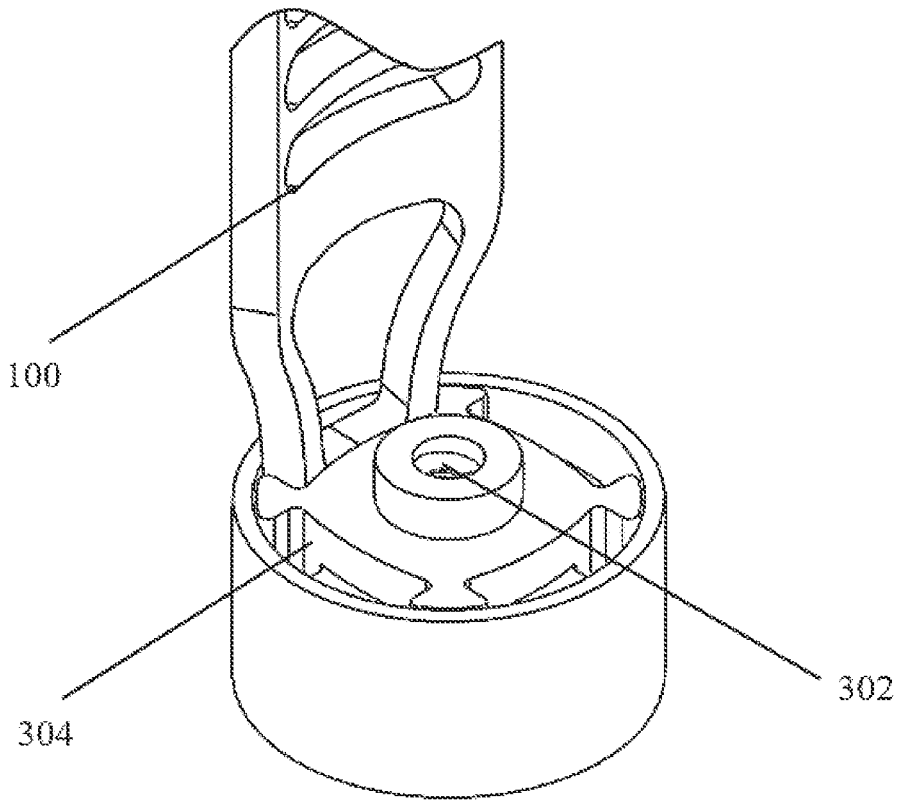
FIG. 44 is a schematic diagram illustrating a connection of a clamp and a second connector according to some embodiments of the present disclosure.
Figure 45:
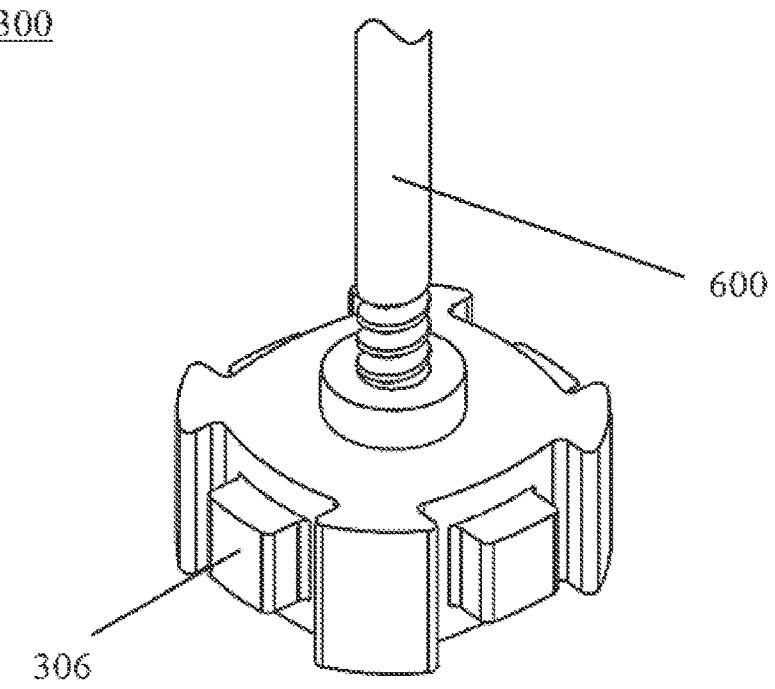
FIG. 45 is a structural schematic diagram illustrating a second connector of a tissue clamping device according to some embodiments of the present disclosure.
Figure 46:
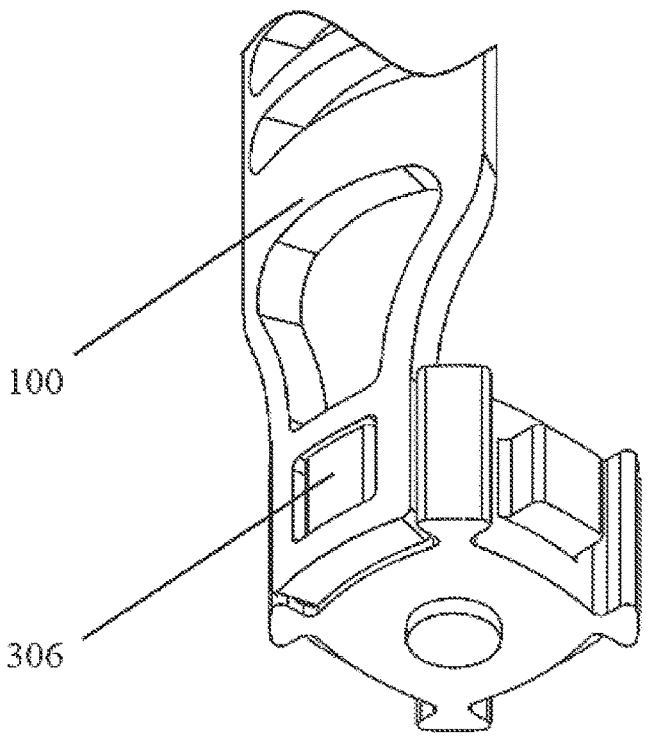
FIG. 46 is a schematic diagram illustrating a connection of a clamp and a second connector according to some embodiments of the present disclosure.

FIG. 43 is a structural schematic diagram illustrating a second connector of a tissue clamping device according to some embodiments of the present disclosure. FIG. 44 is a schematic diagram illustrating a connection of a clamp and a second connector according to some embodiments of the present disclosure. FIG. 45 is a structural schematic diagram illustrating a second connector of a tissue clamping device according to some embodiments of the present disclosure. FIG. 46 is a schematic diagram illustrating a connection of a clamp and a second connector according to some embodiments of the present disclosure. As shown in FIGS. 43-46, a center of a second connector 300 may include a connection hole 302 (e.g., a thread hole), which may be detachably connected to a brake lever 600. In some embodiments, as shown in FIGS. 43-44, one or more mounting holes 304 may be disposed around the connection hole 302, and the one or more mounting holes 304 may be configured to dispose a first exterior clamping arm 140, a second exterior clamping arm 150, a first mounting unit 730, and a second mounting unit 740 of an elastic bracket 700. As shown in FIG. 44, a first end of the first exterior clamping arm 140 (e.g., a lower end as shown in FIG. 44) may be inserted into one of the mounting holes 304 of the second connector 300 and fixedly connected to the second connector 300. In addition, a first end of the second exterior clamping arm 150 may be inserted into one of the mounting holes 304 of the second connector 300 and fixedly connected to the second connector 300. For example, the first end of the first exterior clamping arm 140 and/or the first end of the second exterior clamping arm 150 may be fixedly connected to the second connector 300 via a bonding connection, a welding connection, a snapping connection, etc., at an internal or bottom end (e.g., a lower end shown in FIG. 44) of the mounting hole 304. In some embodiments, as shown in FIGS. 45-46, a side wall of the second connector 300 may include a convex block 306 configured to dispose the first exterior clamping arm 140, the second exterior clamping arm 150, the first mounting unit 730, and the second mounting unit 740 of the elastic bracket 700. As shown in FIG. 46, the first end of the first exterior clamping arm 140 (e.g., a lower end as shown in FIG. 44) may be connected to one of the convex blocks 306 of the second connector 300 via a snapping connection and may be fixedly connected to the second connector 300. The connection of the first end of the first exterior clamping arm 140 and the second connector 300 may include a bonding connection, a welding connection, or the like, or any combination thereof. In some embodiments, when the four convex blocks 306 on the side wall of the second connector 300 are respectively connected to the first exterior clamping arm 140, the second exterior clamping arm 150, and the first mounting unit 730 and the second mounting unit 740 of the elastic bracket 700 via a snapping connection, a fixing sleeve may be sleeved outside the second connector 300, thereby effectively preventing each of the components mentioned above from disengaging from the convex blocks 306. The fixing sleeve may be fixedly connected to the second connector 300 via a welding connection, a bonding connection, etc. In some alternative embodiments, when a tissue clamping device includes the locking mechanism 500, a center of the second connector 300 may include a connection hole which may be fixedly connected to a locking tube (e.g., the locking tube 510 and/or the locking tube 520).

In some embodiments, the tissue clamping device may be controlled by a control handle, and the control handle may be connected to the tissue clamping device via the conveying assembly. Specifically, the control handle may include a brake lever control mechanism and/or a clip control mechanism. The brake lever control mechanism may be configured to control an expansion and a rotation of the brake lever 600. The clip control mechanism may be configured to control the first clip 410 and the second clip 420 to be expanded and/or folded relative to the first interior clamping arm 120 and the second interior clamping arm 130, respectively.

In some embodiments, a method for using a tissue clamping device in the present disclosure may include the following operations:

(1) A tissue clamping device may be conveyed to a predetermined position via a conveying assembly;

(2) A second connector 300 may be controlled to move relative to a first connector 200 by a brake lever 600, and a first interior clamping arm 120 and a second interior clamping arm 130 may be relatively expanded to an angle;

(3) A first clip 410 and a second clip 420 may be controlled to be expanded or folded relative to the first interior clamping arm 120 and the second interior clamping arm 130, respectively, for example, through a first pulling cable and a second pulling cable, and tissues may be clamped between the first clip 410 and the first interior clamping arm 120 and/or between the second clip 420 and the second interior clamping arm 130;

(4) The second connector 300 may be controlled to move relative to the first connector 200, and the first interior clamping arm 120 and the second interior clamping arm 130 may be relatively folded;

(5) The brake lever 600 and the conveying assembly may be controlled to be disengaged from the tissue clamping device. When the tissue clamping device includes a locking mechanism 500, a locking tube 511 on a locking tab 510 may be expanded outward to restrict a relative expansion between the first interior clamping arm 120 and the second interior clamping arm 130.

For example, during treatment of the mitral regurgitation, when the mitral valve is clamped using the tissue clamping device, the tissue clamping device may be conveyed to the mitral valve through the left atrium. The second connector 300 may be controlled to move relative to the first connector 200 through the brake lever 600, and the first interior clamping arm 120 and the second interior clamping arm 130 of the clamp 100 may be expended to an angle (e.g., 120°, 150°, 180°, etc.). The first clip 410 and the second clip 420 may be controlled to be expanded relative to the first interior clamping arm 120 and the second interior clamping arm 130, respectively. A position of the tissue clamping device may be further adjusted, the first interior clamping arm 120 and the second interior clamping arm 130 may be located at a side of the left ventricular, and the first interior clamping arm 120 and the second interior clamping arm 130 may clamp the mitral valve. Subsequently, the first clip 410 and the second clip 420 may be controlled to be folded relative to the first interior clamping arm 120 and the second interior clamping arm 130, respectively, and the mitral valve may be snapped between the first interior clamping arm 120 and the first clip 410 and/or between the second interior clamping arm 130 and the second clip 420. The first interior clamping arm 120 and the second interior clamping arm 130 of the clamp 100 may be controlled to be folded by the brake lever 600, and operation of the tissue clamping device clamping the mitral valve may be completed. Two opposite sides of the mitral valve clamped by the tissue clamping device to render that there are two relatively small holes, instead of one relative large hole, between the valve of the mitral valve. The brake lever 600 and the conveying assembly may be controlled to be disengaged from the tissue clamping device, and the brake lever 600 and the conveying assembly may be removed from the body of a patient. In addition, when a tissue clamping device includes the locking mechanism 500, when the brake lever 600 is disengaged from the locking tube 510, the locking tab 511 of the locking mechanism 500 may be automatically expanded to restrict the first interior clamping arm 120 and the second interior clamping arm 130 of the clamp 100 from expanding, thereby avoiding a detachment of the tissue clamping device from the mitral valve due to an impact of blood flow.

According to the tissue clamping device disclosed in the present disclosure, one or more beneficial effects may be realized. The one or more beneficial effects include: (1) one or more components of the tissue clamping device may be integrally formed, thereby improving the stability of the tissue clamping device and reducing the manufacture cost of the tissue clamping device; (2) one or more bending structures may be disposed between components of the tissue clamping device (e.g., a bending structure disposed between the interior clamping arm and a supporting unit, a bending structure disposed between the interior clamping arm and an exterior clamping arm), which may improve the bending performance of the interior clamping arm of the tissue clamping device and improve clamping efficiency of the tissue clamping device; (3) the bending structure(s) may improve deformation performance when the components of the tissue clamping device are performed a heating operation; (4) one or more agnail clips may be disposed on the tissue clamping device, which may prevent the tissues from coming out between the agnail clip(s) and the interior clamping arm, thereby improving clamping stability of the tissue clamping device; (5) a locking mechanism may be disposed on the tissue clamping device, which may restrict the interior clamping arm from being expanded after the tissue clamping device clamping the tissues, thereby improving the stability of the tissue clamping device; (6) an elastic bracket may be disposed on the tissue clamping device, which may improve the clamping performance of the tissue clamping device on the tissues, protect the tissues, and improve clamping stability of the tissue clamping device. It should be noted that different embodiments may have different beneficial effects. In different embodiments, the beneficial effects may include any of the beneficial effects mentioned above or any other beneficial effects that may be realized.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., $\pm 1\%$, $\pm 5\%$, $\pm 10\%$, or $\pm 20\%$) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value."

We claim:

1. A tissue clamping device, comprising a clamp, a first connector, a second connector, a clip, and an elastic bracket, wherein the clamp includes a supporting unit, a first interior clamping arm, a first exterior clamping arm, a second interior clamping arm, and a second exterior clamping arm, wherein a first side of the supporting unit is connected to the first interior clamping arm and the first exterior clamping arm in sequence via a bendable connection, a second side of the supporting unit is connected to the second interior clamping arm and the second exterior clamping arm in sequence via a bendable connection, and the clamp is integrally formed: the clamp is connected to the first connector and the second connector and between the first connector and the second connector, and a relative movement of the first connector and the second connector drives the first interior clamping arm and the second interior clamping arm to be expanded or folded relatively; and the clip includes a first clip disposed on the first interior clamping arm and a second clip disposed on the second interior clamping arm, and the first clip and the second clip are respectively expanded or folded relative to the first interior clamping arm and the second interior clamping arm, thereby clamping tissues between the first clip and the first interior clamping arm and between the second clip and the second interior clamping arm; and the elastic bracket includes a first supporting rod, a second supporting rod, a first mounting unit, and a second mounting unit, wherein each of the first end of the first supporting rod and the first end of the second supporting rod is connected to the first mounting unit via a curved rod of a fourth S rod; each of the second end of the first supporting rod and the second end of the second supporting rod is connected to the second mounting unit via a curved rod of a fifth S rod;

the first supporting rod, the second supporting rod, the first mounting unit, and the second mounting unit are integrally formed; the first mounting unit and the second mounting unit of the elastic bracket are fixedly connected to the second connector; the first supporting rod of the elastic bracket bears against a connection of the first interior clamping arm and the first exterior clamping arm; and the second supporting rod of the elastic bracket bears against a connection of the second interior clamping arm and the second exterior clamping arm.

2. The tissue clamping device of claim 1, wherein a first end of the supporting unit is connected to the first connector; and a first end of the first exterior clamping arm and a first end of the second exterior clamping arm are connected to the second connector, respectively.

3. The tissue clamping device of claim 1, wherein the first side of the supporting unit is connected to the first interior clamping arm via a first bending structure; the second side of the supporting unit is connected to the second interior clamping arm via the first bending structure; the first bending structure includes a first S rod or a first thin waist bending structure; the first interior clamping arm is connected to the first exterior clamping arm via a second bending structure; the second interior clamping arm is connected to the second exterior clamping arm via the second bending structure; and the second bending structure includes at least one of a second S rod or a second thin waist bending structure.

4. The tissue clamping device of claim 3, wherein the first S rod or the second S rod at least includes three straight rods and two curved rods, the three straight rods are parallel to each other and arranged in sequence, two ends of each two adjacent straight rods of the three straight rods are connected, and the two ends of each two adjacent straight rods of the three straight rods are located at a same side of the first S rod or the second S rod, and the two ends of each two adjacent straight rods of the three straight rods are connected via one of the two curved rods.

5. The tissue clamping device of claim 1, wherein the supporting unit includes a grid structure, and the grid structure includes a rhombus grid structure, a circular grid structure, a rectangular grid structure, a square grid structure, a triangular grid structure, or a regular polygon grid structure.

6. The tissue clamping device of claim 1, wherein the clamp is integrally formed by cutting and performing a heating and shaping operation on a shape-memory alloy tube.

7. The tissue clamping device of claim 1, wherein the clip includes an agnail clip, and the agnail clip includes a fixing unit, a clipping unit, and an agnail, wherein a first end of the fixing unit is connected to a first end of the clipping unit via a bending unit, wherein the bending unit includes a first S rod; and the agnail is disposed on a second end of the clipping unit.

8. The tissue clamping device of claim 7, wherein the fixing unit, the clipping unit, and the agnail are integrally formed; or the fixing unit and the clipping unit of the agnail clip are integrally formed with the clamp.

9. The tissue clamping device of claim 8, wherein the agnail includes a plurality of agnail bars, and at least one of the plurality of agnail bars is connected to the second end of the clipping unit via a third S rod, and/or the at least one of the plurality of agnail bars includes one or more through-holes.

10. The tissue clamping device of claim 7, the agnail being connected to the second end of the clipping unit via a detachable connection, wherein the second end of the clipping unit includes a slot, the agnail includes a snap ring, and the snap ring is connected to the slot via a snapping connection.

11. The tissue clamping device of claim 7, wherein the fixing unit and the clipping unit are integrally formed by cutting and performing a heating and shaping operation on a shape-memory alloy; and after being performed the heating and shaping operation, the fixing unit and the clipping unit form a certain angle and the bending unit has prefabricated resilience force.

12. The tissue clamping device of claim 7, wherein each of the first interior clamping arm and the second interior clamping arm includes a through-hole which is matched with the agnail.

13. The tissue clamping device of claim 7, wherein each of the first interior clamping arm and the second interior clamping arm includes a snap hole matched with the fixing unit of the agnail clip, and the fixing unit is embedded in the snap hole; each of the first interior clamping arm and the second interior clamping arm includes a fixing slot; the tissue clamping device further includes a fixing ring; and the fixing ring is connected to the fixing slot via a snapping connection to restrict the fixing unit from disengaging from the snap hole.

14. The tissue clamping device of claim 7, wherein the agnail clip includes at least two agnails, the at least two agnails being disposing at different positions of the clipping unit.

15. The tissue clamping device of claim 1, further including a locking mechanism and the locking mechanism including a locking tube and a locking piece, wherein one end of the locking tube is fixedly connected to the second connector, and an exterior wall of the locking tube includes a locking tab; the locking piece is fixedly connected to the supporting unit; and the locking tab restricts a relative expansion between the first interior clamping arm and the second interior clamping arm by restricting a movement of the locking piece.

16. The tissue clamping device of claim 15, wherein the locking mechanism further includes a sleeve, the sleeve sleeving outside the locking tube and being configured to retract the locking tab; the tissue clamping device further includes a brake lever, and the brake lever being fixedly connected to the sleeve and detachably connected to the locking tube; when the brake lever is connected to the locking tube, the sleeve retracts the locking tab, and when the brake lever is disengaged from the locking tube, the sleeve releases an effect on the locking tab and the locking tab is expanded.

17. The tissue clamping device of claim 15, wherein the locking tab includes at least two tabs, and the at least two tabs are disposed on two positions on an exterior wall of the locking tube, and a distance between one of the two positions and the second connector and a distance between the other of the two positions and the second connector are different, and the at least two tabs restrict the clamp from being expanded when the first interior clamping arm and the second interior clamping arm are expanded to different angles.

18. The tissue clamping device of claim 1, wherein each of the first end of the first supporting rod and the first end of the second supporting rod is connected to the first mounting unit via a first connecting unit; each of the second end of the first supporting rod and the second end of the second supporting rod is connected to the second mounting unit via a second connecting unit; and each of the first connecting unit and the second connecting unit includes one or more through-holes.

19. An elastic bracket of a tissue clamping device, comprising a first supporting rod, a second supporting rod, a first mounting unit, and a second mounting unit, wherein a first end of the first supporting rod and a first end of the second supporting rod are connected to the first mounting unit; a second end of the first supporting rod and a second end of the second supporting rod are connected to the second mounting unit; wherein each of the first end of the first supporting rod and the first end of the second supporting rod is connected to the first mounting unit via a curved rod of a fourth S rod; each of the second end of the first supporting rod and the second end of the second supporting rod is connected to the second mounting unit via a curved rod of a fifth S rod: and the first supporting rod, the second supporting rod, the first mounting unit, and the second mounting unit are integrally formed.

* * * * *